US010738092B2

(12) United States Patent
Skerra et al.

(10) Patent No.: US 10,738,092 B2
(45) Date of Patent: *Aug. 11, 2020

(54) MUTEINS OF A1M LIPOCALIN AND METHOD OF PRODUCTION THEREFOR

(71) Applicant: TECHNISCHE UNIVERSITAET MUENCHEN, Munich (DE)

(72) Inventors: Arne Skerra, Freising (DE); Winfried Meining, Zolling (DE); Evelyn Eggenstein, Freising (DE)

(73) Assignee: Technische Universitaet Muenchen, Munich (DE)

( * ) Notice: Subject to any disclaimer, the term of this patent is extended or adjusted under 35 U.S.C. 154(b) by 155 days.

This patent is subject to a terminal disclaimer.

(21) Appl. No.: 15/680,970

(22) Filed: Aug. 18, 2017

(65) Prior Publication Data

US 2018/0066028 A1  Mar. 8, 2018

Related U.S. Application Data

(63) Continuation of application No. 14/375,188, filed as application No. PCT/EP2013/051962 on Jan. 31, 2013, now Pat. No. 9,758,554.

(Continued)

(51) Int. Cl.
| C40B 40/10 | (2006.01) |
| C07K 14/47 | (2006.01) |
| C07K 14/81 | (2006.01) |
| A61K 38/00 | (2006.01) |

(52) U.S. Cl.
CPC .......... *C07K 14/47* (2013.01); *C07K 14/8114* (2013.01); *A61K 38/00* (2013.01);
(Continued)

(58) Field of Classification Search
None
See application file for complete search history.

(56) References Cited

U.S. PATENT DOCUMENTS

| 9,051,382 B2 | 6/2015 | Trentmann et al. |
| 9,221,885 B2 | 12/2015 | Matschiner et al. |

(Continued)

FOREIGN PATENT DOCUMENTS

| EP | 1 790 727 A2 | 5/2007 |
| WO | WO 02/15939 A2 | 2/2002 |

(Continued)

OTHER PUBLICATIONS

European Patent Office Communication pursuant to Article 94(3) EPC, issued in Application No. 13706935.7 dated Feb. 13, 2017.
(Continued)

*Primary Examiner* — Christian C Boesen
(74) *Attorney, Agent, or Firm* — Brian E. Reese; Dana M. Daukss; Choate, Hall & Stewart, LLP

(57) ABSTRACT

The present disclosure relates to a collection of novel muteins derived from human α1m (or a1m) polypeptide or a functional homologue thereof. The disclosure further refers to a α1m mutein capable of specifically binding to one or more targets other than a target to which wild-type α1m binds. The disclosure also relates to a method for producing such collection of muteins and a method for isolating a mutein capable of binding one or more such non-natural targets of wild-type α1m polypeptide. These aspects are made possible due to, e.g, the structural elucidation of α1m disclosed herein by the present inventors, an appreciation of ligand-binding sights thereof and, hence, an understanding of which amino acid positions are most suitable for mutagenesis for re-engineering specificity and affinity for any given target while maintaining the secondary and/or tertiary structure of a1m.

20 Claims, 20 Drawing Sheets

Specification includes a Sequence Listing.

Related U.S. Application Data

(60) Provisional application No. 61/592,843, filed on Jan. 31, 2012.

(52) U.S. Cl.
    CPC ...... *C07K 2319/00* (2013.01); *C07K 2319/02* (2013.01); *C07K 2319/50* (2013.01); *C40B 40/10* (2013.01)

(56) References Cited

U.S. PATENT DOCUMENTS

| | | |
|---|---|---|
| 9,549,968 B2 | 1/2017 | Skerra et al. |
| 9,758,554 B2 | 9/2017 | Skerra et al. |
| 2010/0129846 A1 | 5/2010 | Goldknopf |

FOREIGN PATENT DOCUMENTS

| | | |
|---|---|---|
| WO | WO 02/16600 A2 | 2/2002 |
| WO | WO 2005/019256 A2 | 3/2005 |
| WO | WO 2009/156456 A1 | 12/2009 |

OTHER PUBLICATIONS

Allhorn et al., "Redox properties of the lipocalin $\alpha_1$-microglobulin: Reduction of cytochrome *c*, hemoglobin, and free iron," Free Radical Biology & Medicine, 2005 (Dec. 21, 2004), 38(5):557-567.

Beste et al., "Small antibody-like proteins with prescribed ligand specificities derived from the lipocalin fold," Proc. Natl. Acad. Sci. USA, Mar. 2, 1999, 96(5):1898-1903.

Breustedt et al., "A new crystal form of human tear lipocalin reveals high flexibility in the loop region and induced fit in the ligand cavity," Acta Crystallographica Section D Biological Crystallography, Sep. 16, 2009, 65(10):1118-1125.

Korde et al., "$^{99m}$Tc-labeling of colchicine using [$^{99m}$Tc(CO)$_3$(H$_2$O)d]$^+$ and [$^{99m}$TC≡N]$^{2+}$core for the preparation of potential tumor-targeting agents," Bioorganic & Medicinal Chemistry, Nov. 11, 2005, 14(3):793-799.

Kwasek et al., "Production of recombinant human $\alpha_1$-microglobulin and mutant forms involved in chromophore formation," Protein Expression and Purification, Feb. 24, 2007, 53(1):145-152.

Lindqvist et al., "Bovine $\alpha_1$-microglobulin/bikunin. Isolation and characterization of liver cDNA and urinary $\alpha_1$-microglobulin," Biochimica et Biophysica Acta, 1996, pp. 98-106.

Molecular weight: 1068.24 g/mol

Molecular weight: 916.09 g/mol

FIGURE 10A anti-mouse IgG/AP-conjugate

StrepMAB-Classic periplasmic extract 0.5 µM biotinylated target

5 µg/ml Streptavidin

FIGURE 13

```
          1         10        20        30        40        50        60        70        80        90       100
          .         .         .         .         .         .         .         .         .         .         .
a1m       GPVPTPPDNIQVQENFNISRIYGKWYNLAIGSTSPWLKKIMDRMTVSTLVLGEGATEAEISMTSTRWRKGVCEETSGAYEKTDTDGKFLYHKSKWNITME
Library   .........q........................x.xx............x..........x.xx............x.xx.........x..x.x.
D1A10     .........q........................K.VK............A..........M.Y............K.F.E.........G..h.V.W.
D1A11     .........q........................I.ER............Q..........A.A............E.P.D.........Y..h.Y.H.
D1B1      .........q........................Q.RL............H..........G.P............K.F.K.........K..h.H.K.
D1E1      .........q........................H.KQ............I..........V.E............W.F.R.........I..h.N.M.
D1H3      .........q........................I.TK............D..........M.G............A.WGY........N..h.Y.M.
          ===============A====================#1=========B=====C========#2====D=======E====#3

101       110       120       130       140       150       160       170       180
          .         .         .         .         .         .         .         .         .
a1m       SYVVHTNYDEYAIFLTKKFSRHHGPTITAKLYGRAPQLRETLLQDFRVVAQGVGIPEDSIFTMADRGECVPGEQEPEPILIPR
Library   .x.x......q.....x.xx.............................................................
D1A10     .Y.H......q.....I.M.A.............................................................
D1A11     .K.K......q.....W.N.W.............................................................
D1B1      .R.I......q.....S.I.Y.............................................................
D1E1      .T.M......q.....W.M.E.............................................................
D1H3      .F.M......q.....W.V.Q.............................................................
          ======F======G=====#4====H===
```

FIGURE 15

```
         1         10        20        30        40        50        60        70        80        90       100
         |         |         |         |         |         |         |         |         |         |         |
a1m      GPVPTPPDNIQVQENFNISRIYGKWYNLAIGSTSPWLKKIMDRMTVSTLVLGEGATEAFISMTSTRWRKGVCEETSGAYEKTDTDGKFLYHKSKWNITME
Library  .........q........q........x.xx........x.........x.x.......x.x..............x.x.......x...h.x.x
C1A1     .........q........q....F.WH........Y.............N.E.......L.H.R.............K...K....K...h.E.W.
C1A2     .........q........q....S.-H........D.............A.I.......E.H.Y.............W...W....W...h.E.V.
C1D1     .........q........q....-.FS........D.............V.F.......Y.K.E.............L...L....L...h.Q.I.
         ====A=========#1=======B==========C===#2======D=========E======#3

101       110       120       130       140       150       160       170       180
         |         |         |         |         |         |         |         |         |
a1m      SYVVHTNYDEYAIFLTKKFSRHHGPTITAKLYGRAPQLRETLLQDFRVAQGVGIPEDSIFTMADRGECVPGEQEPEPILIPR
Library  .........q........x.x..x................................................
C1A1     .........q....S.D..q..P.E.M..............................................
C1A2     .........q....I.W..q..H.E.W..............................................
C1D1     .........q....I.E..q..N.V.F..............................................
         ====F==============G======#4=============H
```

MUTEINS OF A1M LIPOCALIN AND METHOD OF PRODUCTION THEREFOR

CROSS REFERENCE TO RELATED APPLICATIONS

This application is a continuation of U.S. application Ser. No. 14/375,188, filed Jul. 29, 2014, which is a National Stage application of PCT/EP2013/051962, filed Jan. 31, 2013, which claims priority from U.S. Provisional Application No. 61/592,843, filed Jan. 31, 2012.

SEQUENCE LISTING

The instant application contains a Sequence Listing which has been submitted electronically in ASCII format and is hereby incorporated by reference in its entirety. Said ASCII copy, created on Jul. 11, 2016, is named 029029-0154_SL.txt and is 97,042 bytes in size.

BACKGROUND

Proteins that selectively bind to selected targets by way of non-covalent interaction play a crucial role as reagents in biotechnology, medicine, bioanalytics as well as in the biological and life sciences in general. Antibodies, i.e. immunoglobulins, are a prominent example of this class of proteins. Despite the manifold needs for such proteins in conjunction with recognition, binding and/or separation of ligands/targets, almost exclusively immunoglobulins are currently used.

Additional proteinaceous binding molecules that have antibody-like functions are certain members of the lipocalin family, which have naturally evolved to endogenously bind ligands. Lipocalins occur in many organisms, including vertebrates, insects, plants and bacteria. Members of the lipocalin protein family (Pervaiz, S., & Brew, K. (1987) FASEB J. 1, 209-214) are typically small, secreted proteins and have a single polypeptide chain. They are characterized by a range of different molecular-recognition properties: their ability to bind various, principally hydrophobic molecules (such as retinoids, fatty acids, cholesterols, prostaglandins, biliverdins, pheromones, tastants, and odorants), their binding to specific cell-surface receptors and their formation of macromolecular complexes. Although they have, in the past, been classified primarily as transport proteins, it is now clear that the lipocalins fulfill a variety of physiological functions. These include roles in retinol transport, olfaction, pheromone signaling, and the synthesis of prostaglandins. The lipocalins have also been implicated in the regulation of the immune response and the mediation of cell homeostasis (reviewed, for example, in Flower, D. R. (1996) Biochem. J. 318, 1-14 and Flower, D. R. et al. (2000) Biochim. Biophys. Acta 1482, 9-24).

$\alpha_1$-Microglobulin ($\alpha_1$m)—also known as protein HC, $\alpha_1$-glycoprotein or $\alpha_1$-microglyco-protein—is a 26 kDa glycoprotein with 184 amino acid residues which is abundant in blood plasma, urine, and connective tissue of humans as well as vertebrate animals (Åkerström, B., Lögdberg, L., Berggärd, T., Osmark, P., and Lindqvist, A. (2000) Biochim Biophys Acta 1482, 172-184). Based on characteristic amino acid sequence motifs, $\alpha_1$m has been assigned a member of the lipocalin family (Pervaiz, S., and Brew, K. (1987) FASEB J 1, 209-214; Pervaiz, S., and Brew, K. (1985) Science 228, 335-337), although this has been done without knowing the three-dimensional structure of this biomolecule. Natural a1m from urine and plasma is heterogeneous in size and charge and has a characteristic yellow-brown color Åkerström, B., and Berggärd, I. (1979) Eur J Biochem 101, 215-223; Berggärd, T., Cohen, A., Persson, P., Lindqvist, A., Cedervall, T., Silow, M., Thogersen, I. B., Jonsson, J. A., Enghild, J. J., and Åkerström, B. (1999) Protein Sci 8, 2611-2620), an attribute that also served to designate this lipocalin (kerström, B., Lögdberg, L., Berggärd, T., Osmark, P., and Lindqvist, A. (2000) Biochim Biophys Acta 1482, 172-184). $\alpha_1$m is glycosylated at three sites: two complex carbohydrates are N-linked to residues Asn17 and Asn96 while Thr5 is O-glycosylated (Ekström, B., Lundblad, A., and Svensson, S. (1981) Eur J Biochem 114, 663-666; Escribano, J., Lopex-Otin, C., Hjerpe, A., Grubb, A., and Mendez, E. (1990) FEBS Lett 266, 167-170). Since its initial identification in humans (Ekström, B., Peterson, P. A., and I., B. (1975) Biochem Biophys Res Commun. 65, 1427-1433), $\alpha_1$m has been associated with various physiological processes including immunosuppression (Åkerström, B., Lögdberg, L., Berggärd, T., Osmark, P., and Lindqvist, A. (2000) Biochim Biophys Acta 1482, 172-184; Lögdberg, L., and Åkerström, B. (1981) Scand J Immunol 13, 383-390), lymphocyte stimulation, and also inhibition of lymphocyte cell proliferation (Wester, L., Michaelsson, E., Holmdahl, R., Olofsson, T., and Åkerström, B. (1998) Scand J Immunol 48, 1-7) as well as neutrophil chemotaxis (Mendez, E., Fernandez-Luna, J. L., Grubb, A., and Leyva-Cobian, F. (1986) Proc Natl Acad Sci USA 83, 1472-1475). Furthermore, several biochemical activities have been ascribed to $\alpha_1$m, in particular in the context of heme and tryptophan metabolism (Olsson, M. G., Olofsson, T., Tapper, H., and Åkerström, B. (2008) Free Radic Res 42, 725-736; Allhorn, M., Berggärd, T., Nordberg, J., Olsson, M. L., and Åkerström, B. (2002) Blood 99, 1894-1901) and with regard to reductase and radical scavenging functions (Allhorn, M., Klapyta, A., and Åkerström, B. (2005) Free Radic Biol Med 38, 557-567; Åkerström, B., Maghzal, G. J., Winterbourn, C. C., and Kettle, A. J. (2007) J Biol Chem 282, 31493-31503). In addition, $\alpha$1m serves as an important biomarker in clinical diagnostics for the monitoring of renal tubular dysfunction, renal toxicity, preeclampsia, and hepatitis E (Bolt, H. M., Lammert, M., Selinski, S., and Bruning, T. (2004) Int Arch Occup Environ Health 77, 186-190; Taneja, S., Sen, S., Gupta, V. K., Aggarwal, R., and Jameel, S. (2009) Proteome Sci 7, 39; Yu, H., Yanagisawa, Y., Forbes, M. A., Cooper, E. H., Crockson, R. A., and MacLennan, I. C. (1983) J Clin Pathol 36, 253-259; Devarajan, P., Krawczeski, C. D., Nguyen, M. T., Kathman, T., Wang, Z., and Parikh, C. R. (2010) Am J Kidney Dis 56, 632-642; Anderson, U. D., Olsson, M. G., Rutardottir, S., Centlow, M., Kristensen, K. H., Isberg, P. E., Thilaganathan, B., Åkerström, B., and Hansson, S. R. (2011) Am J Obstet Gynecol 204, 520 e521-525). Apart from these observations, no dedicated physiological ligand for the central hydrophobic pocket of $\alpha$1m—a characteristic feature of all lipocalin proteins (Flower, D. R. (1996) Biochem J 318, 1-14; Skerra, A. (2000) Biochim Biophys Acta 1482, 337-350)—could be identified so far.

Various PCT publications (e.g., WO 99/16873, WO 00/75308, WO 03/029463, WO 03/029471 and WO 2005/19256) disclose how muteins of various lipocalins (e.g. tear lipocalin and hNGAL lipocalin) can be constructed to exhibit a high affinity and specificity against a target that is different than a natural ligand of a wild type lipocalin. This can be done by mutating certain positions of the lipocalin in a rational manner.

Despite the advances made with certain lipocalins in terms of re-engineering their specificity, there remains a need for the generation of other lipocalin muteins that contain different binding sites and alternative lipocalin scaffolds that can be used for such generation. In view of the various potential applications for ligand- or target-binding proteins in the field of life sciences and biotechnology, the generation of muteins of yet other lipocalins would be desirable to, e.g., widen the spectrum of clinical targets against which lipocalin muteins may bind. Without knowing the secondary and tertiary structure of a lipocalin and hence its potential binding sites, any rational attempt to generate one or more muteins of that lipocalin to bind a target of interest would be futile.

Accordingly, to meet said need, the present disclosure provides, for example, the structural elucidation of the lipocalin scaffold human $\alpha_1$m to create, e.g., a collection (i.e. library) of lipocalin muteins including members (i.e. muteins) that have binding affinity and specificity to at least one target other than a target to which wild-type a1m binds. The present disclosure also provides lipocalin muteins whose pocket or loop region may contain more than one binding site as, e.g., the central pocket (i.e. cavity) of the a1m polypeptide is wider than that in other lipocalins.

SUMMARY

The present disclosure can be characterized by the following Embodiments:

Embodiment 1. A collection of at least 10^2 amino acid sequence members comprised of muteins of human a1m polypeptide or a functional homologue thereof, wherein the amino acid sequence of said members differs from human a1m polypeptide at one or more of the sequence positions which correspond to the sequence positions in the four peptide loops #1, #2, #3 and #4 of human a1m polypeptide, and wherein the members of said collection have at least 60% sequence identity with human a1m polypeptide.

Embodiment 2. The collection of Embodiment 1, wherein at least one of said members can specifically bind to at least one target other than a target to which wild-type a1m binds and has no or no substantial binding affinity for endogenous a1m target(s).

Embodiment 3. The collection of Embodiment 1, wherein at least one of said members can specifically bind to at least one target other than the endogenous target(s) to which wild-type a1m binds and retains substantial binding affinity for one or more endogenous a1m target(s).

Embodiment 4. The collection of Embodiment 1, wherein at least one of said members can specifically bind to two targets other than a target to which wild-type a1m binds and has no or no substantial binding affinity for said endogenous a1m target, wherein said at least one of said members has two binding sites.

Embodiment 5. The collection of Embodiment 1 or 2, wherein a target-binding site of said is within any or all of the four peptide loops #1, #2, #3 and #4 of human a1m polypeptide.

Embodiment 6. The collection of Embodiment 3, wherein two target-binding sites are within any or all of the four peptide loops #1, #2, #3 and #4 of human a1m polypeptide.

Embodiment 7. The collection according to any of Embodiments 1 to 6, wherein the amino acid sequence of said members differs from human a1m polypeptide at one or more of the sequence positions which correspond to the linear polypeptide sequence positions 29-48, 63-80, 89-100, and 115-129 of human a1m polypeptide.

Embodiment 8. The collection according to any of Embodiments 1 to 6, wherein the amino acid sequence of said members differs from human a1m polypeptide at one or more of the sequence positions which correspond to the linear polypeptide sequence positions 32-46, 66-72, 91-98, and 118-126 of human a1m polypeptide.

Embodiment 9. The collection according to any of Embodiments 1 to 6, wherein the amino acid sequence of said members differs from human a1m polypeptide at one or more of the sequence positions which correspond to the linear polypeptide sequence positions 34-37, 62-64, 97-99, 116-118, and 126-130 of human a1m polypeptide.

Embodiment 10. The collection according to any one of Embodiments 7-9, wherein the amino acid sequence of said members further differs from human a1m polypeptide at one or more of the sequence positions which correspond to the linear polypeptide sequence positions 30, 47, 64, 73, 75, 77, 79, 90, 99, 116, and 128 of human a1m polypeptide.

Embodiment 11. The collection according to any one of Embodiments 1 to 10, wherein a nucleic acid molecule coding for each member is operably fused thereto with a gene coding for the coat protein pIII of a filamentous bacteriophage of the M13-family or for a fragment of this coat protein.

Embodiment 12. A collection of nucleic acid molecules, each comprising a nucleotide sequence encoding a member comprised in the collection of amino acid sequence members of any of Embodiments 1 to 10, wherein the amino acid sequence of said members has at least 60% sequence homology with human mature a1m sequence and wherein said members comprise at least one mutated amino acid residues at any sequence position in the four peptide loops #1, #2, #3 and #4.

Embodiment 13. A vector comprising the nucleic acid molecule of Embodiment 12.

Embodiment 14. The vector of Embodiment 12, which is a phagemid vector.

Embodiment 15. A host cell containing a nucleic acid molecule of Embodiment 12 or a vector of Embodiment 13 or 14.

Embodiment 16. A method of producing a mutein of human a1m polypeptide or a functional homologue thereof, which mutein specifically binds a target other than a target to which wild-type a1m binds and has no or no substantial binding affinity for an endogenous a1m target, comprising the steps of: (i) screening the collection of any of Embodiments 1 to 11 with a target other than a target to which wild-type a1m binds under conditions that allow formation of a complex between (a) said target desired to be specifically bound and (b) said collection, (ii) removing muteins of the collection having no or no substantial binding affinity to said target; and (iii) isolating the mutein specifically binding to said target.

Embodiment 17. A mutein derived from human a1m polypeptide or a functional homologue thereof, wherein the mutein comprises at least one mutated amino acid residues at any sequence position in the four peptide loops #1, #2, #3 and #4, wherein said a1m or functional homologue thereof has at least 60% sequence homology with human mature a1m sequence, and wherein the mutein can bind a target other than a target to which wild-type a1m binds and wherein the mutein has no or no substantial binding affinity for endogenous a1m target.

Embodiment 18. A mutein according to Embodiment 17, wherein the mutein comprises at least one mutated amino acid residues at any sequence position corresponding to sequence positions 29-48, 63-80, 89-100, and 115-129 of human mature a1m sequence.

Embodiment 19. A mutein according to Embodiment 17, wherein the mutein comprises at least one mutated amino acid residues at any sequence position corresponding to the linear polypeptide sequence positions 32-46, 66-72, 91-98, and 118-126 of human mature a1m sequence.

Embodiment 20. A mutein according to Embodiment 17, wherein the mutein comprises at least one mutated amino acid residues at any sequence position corresponding to the linear polypeptide sequence positions 34-37, 62-64, 97-99, 116-118 and 126-130 of human mature a1m sequence.

Embodiment 21. A mutein according to any one of Embodiments 18-20, wherein the mutein further comprises at least one mutated amino acid residues at any sequence position corresponding to the linear polypeptide sequence positions 30, 47, 73, 75, 77, 79 and 90 of human mature a1m sequence.

Embodiment 22. The mutein according to any one of Embodiments 17 to 21, wherein said mutein can specifically bind to two targets other than a target to which wild-type a1m binds.

Embodiment 23. The mutein according to Embodiment 22, wherein said mutein has two binding sites.

Embodiment 24. The mutein according to any one of Embodiments 17 to 21, wherein said mutein can specifically bind to Colchicine.

Embodiment 25. The mutein according to any one of Embodiments 17 to 21, wherein said mutein can specifically bind to Lutetium (177Lu) DOTA-TATE.

Embodiment 26. An a1m crystal having space group $P3_221$ and unit-cell parameters a=b=66.72, c=80.26, a=b=90.0, g=120.0.

Embodiment 27. A pharmaceutical composition comprising a mutein of any one of Embodiments 17 to 25 and a pharmaceutically acceptable carrier or excipient.

Embodiment 28. A diagnostic composition comprising a mutein of any one of Embodiments 17 to 25 and optionally means for diagnostic such as a label or marker that is to be coupled, bound or complexed with/to said lipocalin.

Figure 1A:
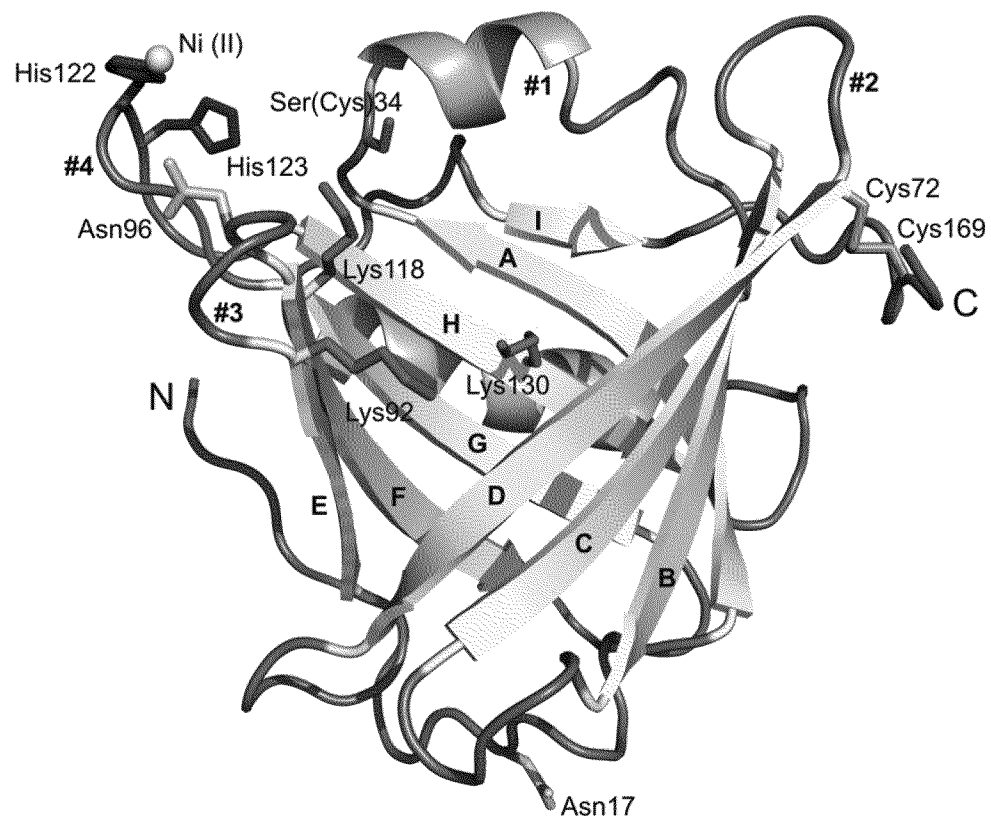
In FIG. 1A, secondary structure elements are shown as a cartoon presentation (yellow, β-strands; pink, α-helices). The following amino acid side chains are highlighted as sticks: the disulfide bridge (Cys72-Cys169), the position of the unpaired Cys34 in the native protein that gives rise to covalent crosslinking to other plasma proteins such as IgA (Ser in the recombinant protein), the four residues assumed to be involved in chromophore binding (Ser/Cys34, Lys92, Lys118, Lys130), two N-glycosylation sites (Asn17 and Asn96), and the pair of His122 and His123 that participate in $Ni^{2+}$ complexation (see below). The four loops which connect neighboring β-strands at the open end of the eight-stranded β-barrel and form the entry to the characteristic ligand pocket are labeled #1 to #4. Strand I is not part of the β-barrel but constitutes an extended segment spanning the distance between the long α-helix that is attached to the side of the β-barrel and the C-terminal disulfide bond.
Figure 1B:
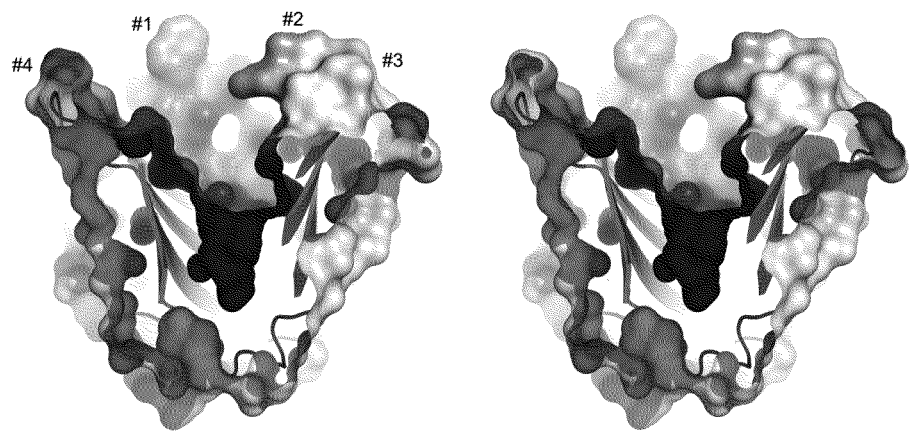
FIG. 1. Crystal structure of human a1m.

The FIG. 1B depicts the stereo view of a section through the electrostatic potential surface of a1m (from −10 kBT/e, red, to +10 kBT/e, blue), illustrating the deep and positively charged ligand pocket.

Figure 1C:
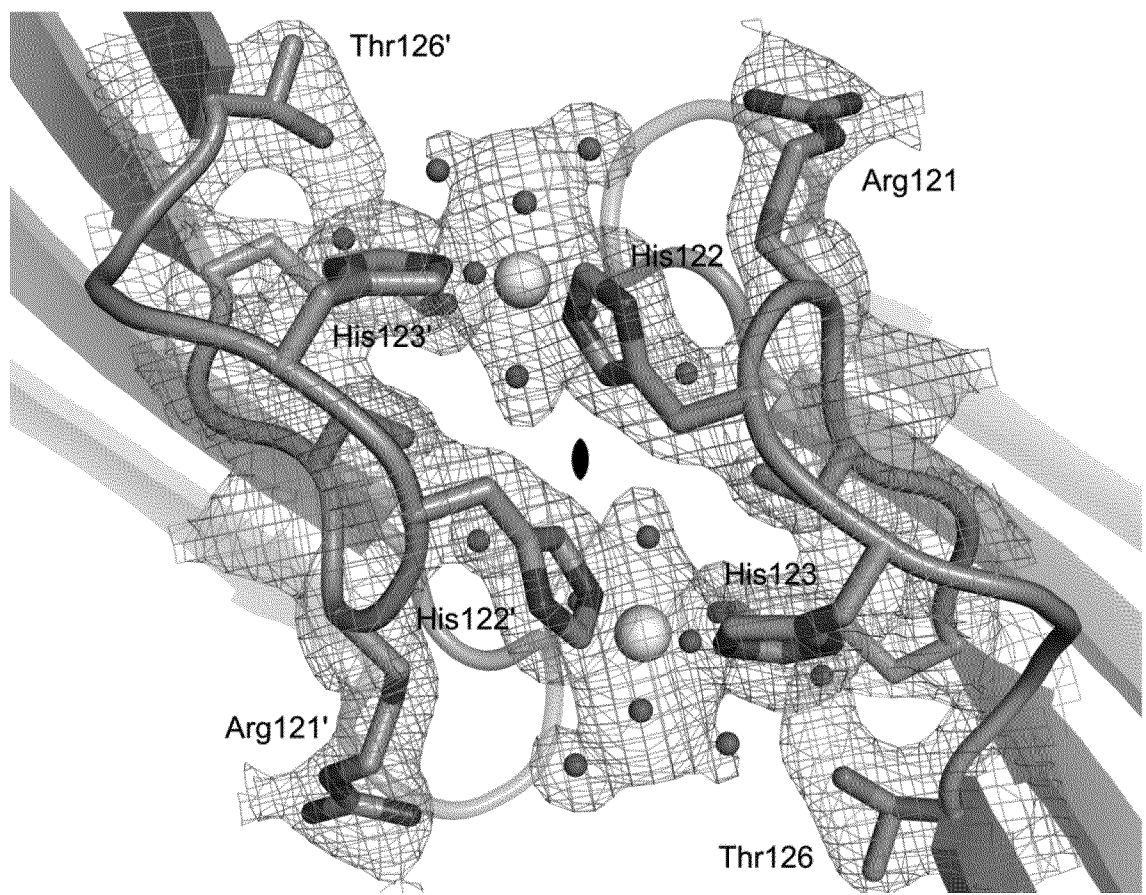

In FIG. 1C, the $Ni^{2+}$ binding site at the interface of two neighboring a1m monomers in the crystal is shown with the 2mFo-DFc electron density contoured at 0.8σ. The crystallographic twofold symmetry axis is indicated at the center. The distance between the two $Ni^{2+}$ ions (cyan) is 7.8 Å, indicating independent complex formation (instead of a binuclear inorganic complex). Water molecules within 3.5 Å distance to the metal ions as well as some crystallographically defined hydrogen-bonded water molecules in the second coordination shell are shown (red).

FIG. 2. A potential heme binding site in the three-dimensional structure of human α1m.

Figure 2A:
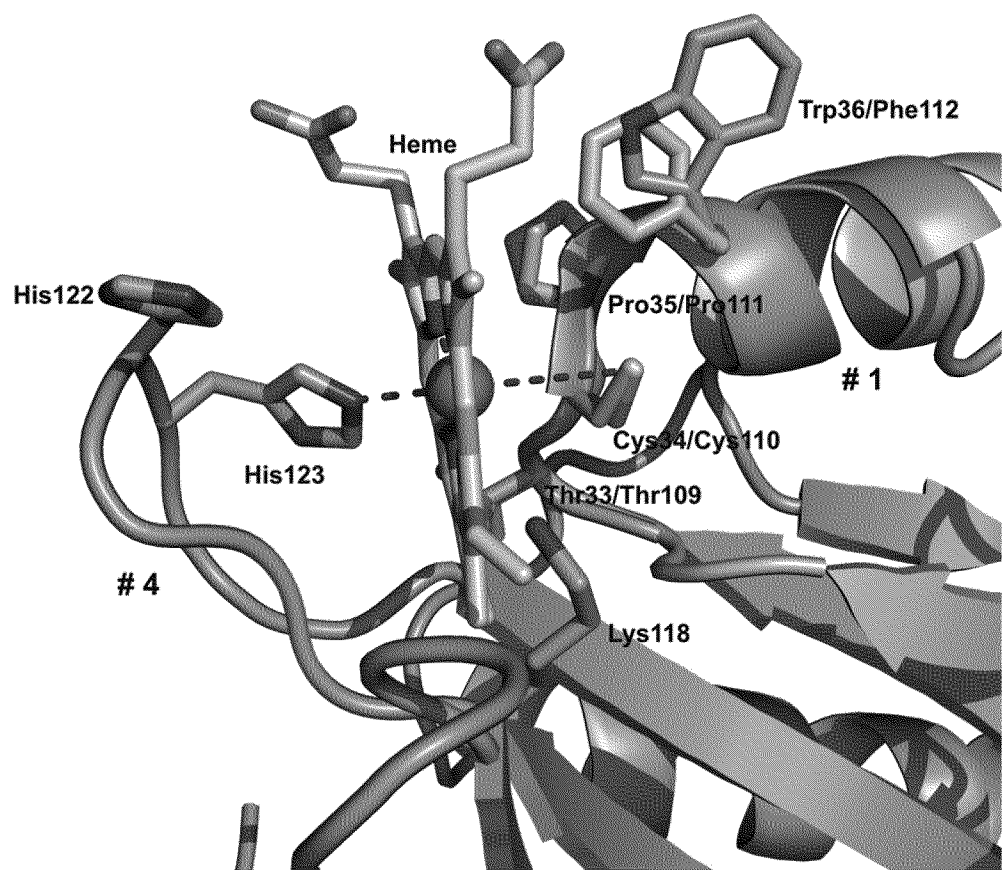

FIG. 2A depicts part of the loop region of a1m (orange) with a superimposed structural segment of microsomal prostaglandin E synthase (PGES, pink; PDB ID: 2PBJ) including its bound heme group—using the Cα positions of the common TCP[F/W] motif. In this model, side chain rotamers of His123 and Cys34 were so chosen that the relative axial position to the central $Fe^{3+}$ ion were optimized. For reasons of clarity, only PGES residues 102-120 are shown.

Figure 2B:
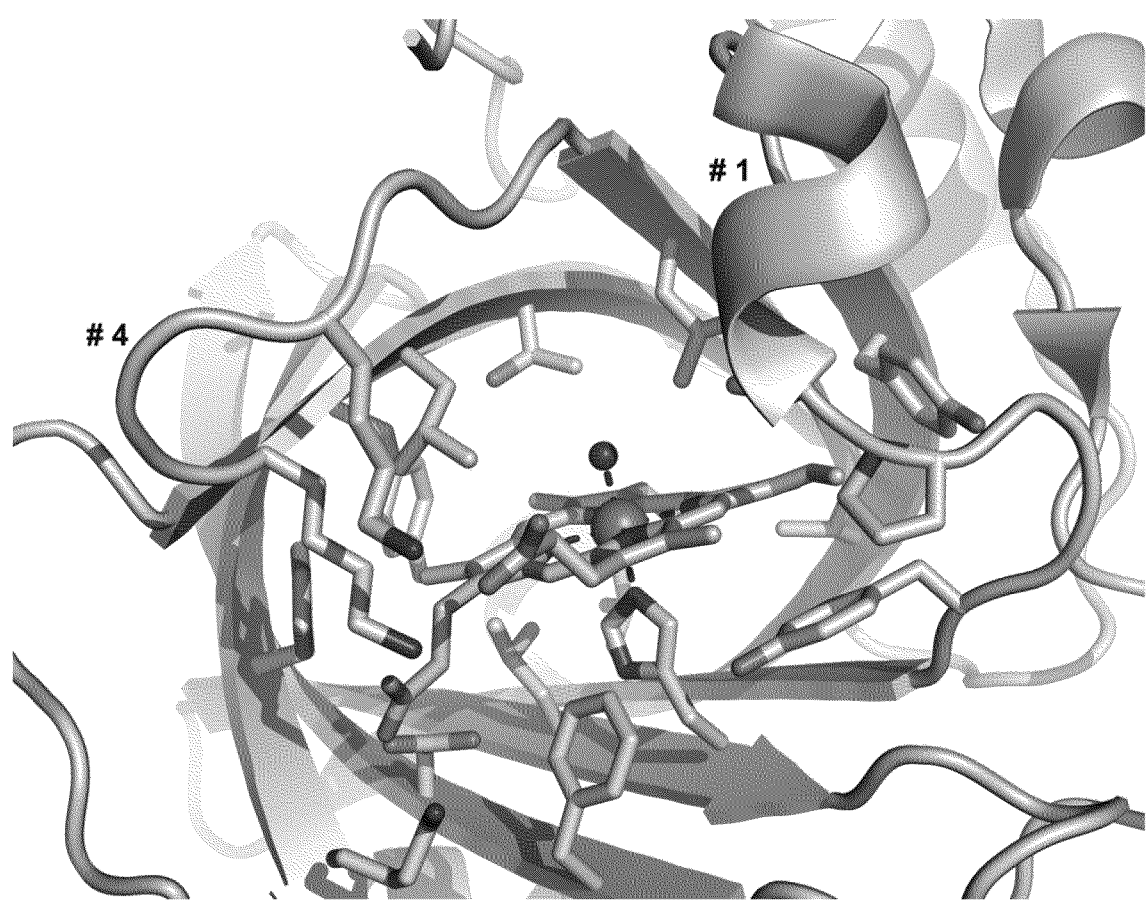

For comparison, in FIG. 2B, nitrophorin 4 from *Rhodnius prolixus* is depicted as complex with its bound heme group within the central cavity and an axial ammonia ligand (PDB ID: 1X8P). Side chains within 4 Å around the heme group are shown as sticks.

FIG. 3. Comparison of human a1m with three structurally most related lipocalins.

Figure 3A:
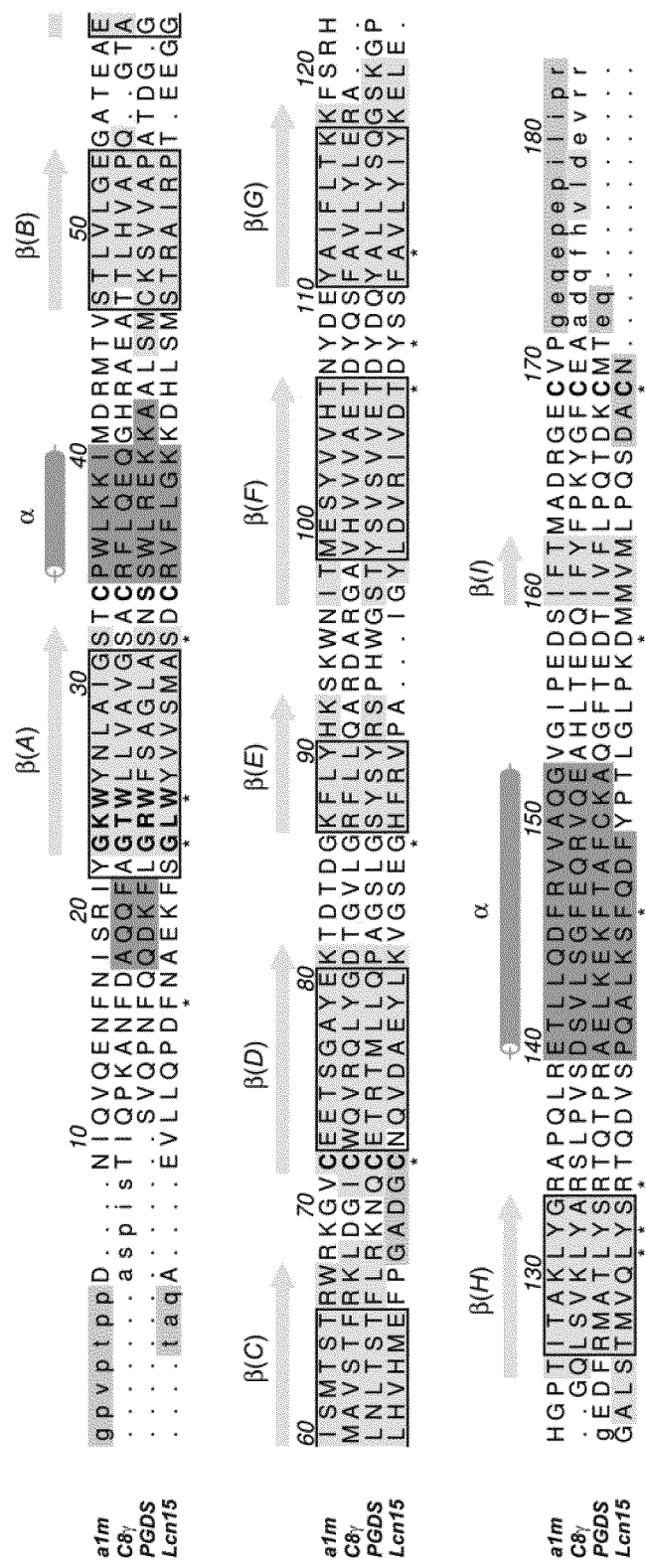

FIG. 3A depicts structure-based sequence alignment of human a1m (SEQ ID NO: 59) denoted as "a1m") in comparison with human complement component C8γ (PDB ID: 2QOS, chain C) (SEQ ID NO: 22, denoted as "C8γ"), human L-prostaglandin D synthase (PDB ID: 3O2Y, chain B) (SEQ ID NO: 23, denoted as "PGDS"), and human lipocalin 15 (PDB ID: 2XST, chain A) (SEQ ID NO: 24, denoted as "Lcn15"). Expression tags were omitted and mutations in the recombinant proteins (a1m: $Cys^{34}Ser$; C8γ: $Cys^{40}Ala$, $Asp^{98}Gly$; PGDS: $Cys^{65}Ala$; Lcn15: $Thr^{17}Ser$, $Ala^{18}Met$) were reverted to reflect their natural amino acid sequences. Residues for which X-ray coordinates were missing are shaded grey. The characteristic Gly-X-Trp motif of the lipocalins, the pair of Cys residues that gives rise to the topologically conserved disulfide bridge, and the single unpaired Cys residue are printed in bold. Insertions relative to a1m are indicated by lowercase letters. α-helices and β-strands were derived from the respective coordinates and are indicated by pink and green color, respectively. 100% conserved residues are labelled with stars. The 58 structurally conserved residues in the β-barrel region of each lipocalin (Skerra, A. (2000) *Biochim Biophys Acta* 1482, 337-350), whose Cα positions were used to align the four structures in panel (b), are boxed.

Figure 3B:
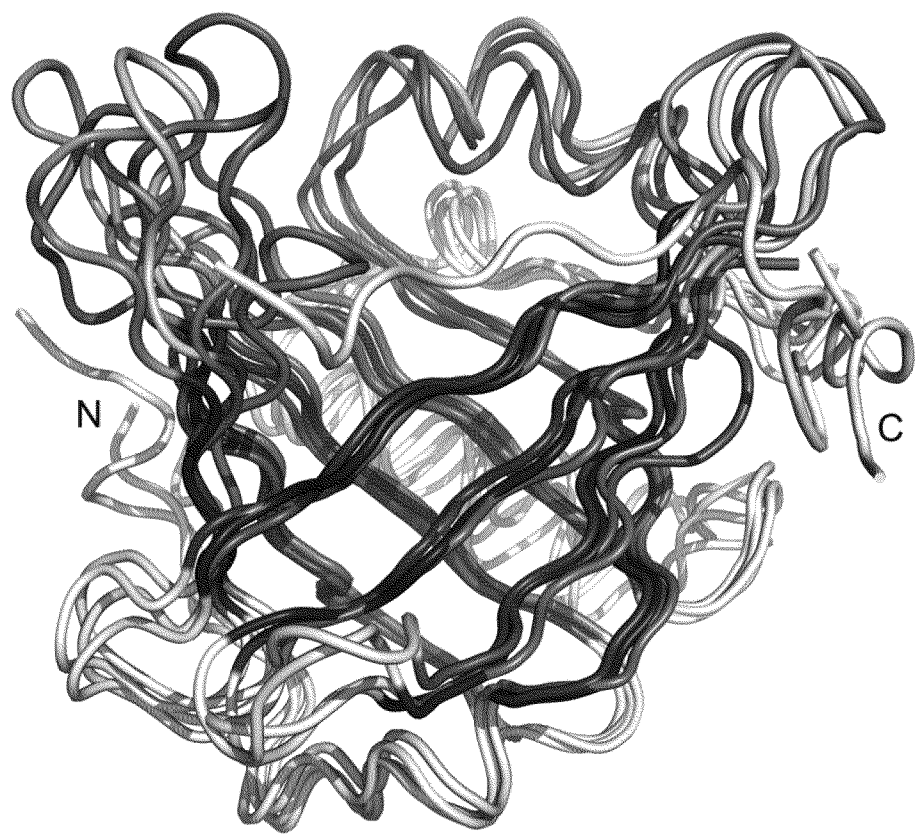

FIG. 3B shows the ribbon representation of the superimposed crystal structures of a1m, C8γ, PGDS, and Lcn15 based on the 58 Cα positions indicated in (a) and here depicted in darker shades of grey. The resulting RMSD values versus a1m are 0.76 Å (C8γ), 1.02 Å (PGDS), and 0.84 Å (Lcn15). Loops are colored individually (orange, a1m; palegreen, C8γ; marineblue, PGDS; pink, Lcn15). Two sequence stretches in the loop region are not resolved in the Lcn15 structure.

Figure 4:
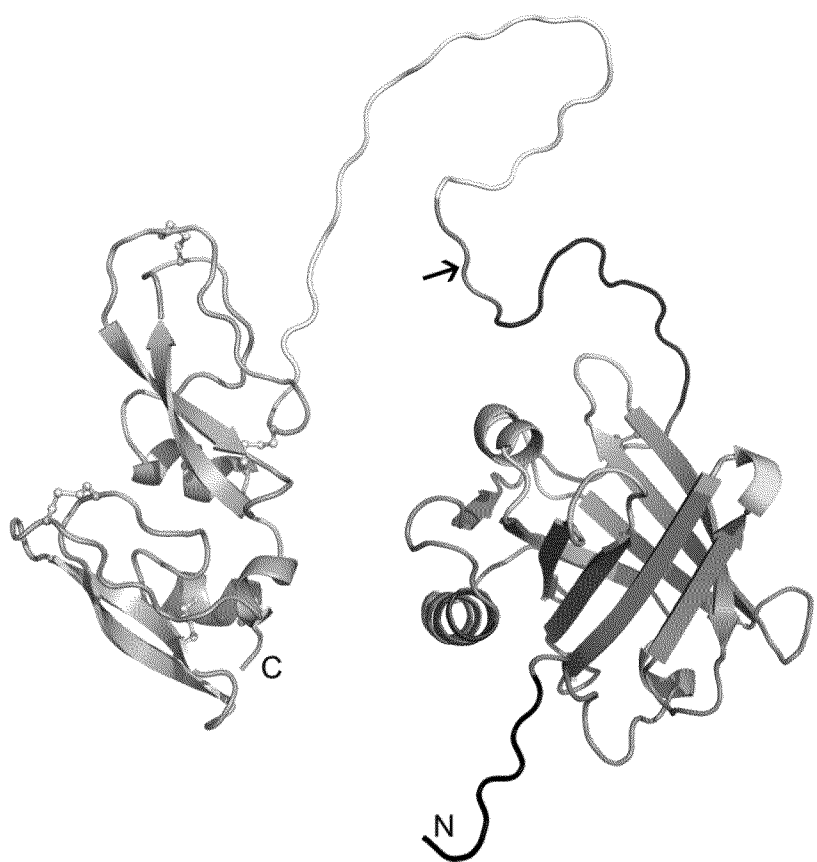

FIG. 4. Model of the a1m/bikunin precursor protein (AMBP).

This structural model is based on the X-ray structure of a1m as described herein (residues 27-190 in AMBP, orange)

and the previously published crystal structure of the serine protease inhibitor bikunin (residues 230-339 in AMBP, pink; PDB ID: 1BIK).

The linker region was modeled in a random conformation; the proteolytic cleavage site therein (residues 202-205) is indicated by an arrow. The N-terminal 19 residue secretory signal peptide, which is processed by signal peptidase, is omitted. The loop region around the ligand pocket of a1m is highlighted (cyan). The two internal repeat regions of bikunin (green) that are presumably involved in the inhibitory interaction with target serine proteases were identified by superposition with the trypsin/trypsin inhibitor complex (PDB ID: 2PTC). Disulfide bridges are shown in a ball-and-stick representation.

Figure 5A:
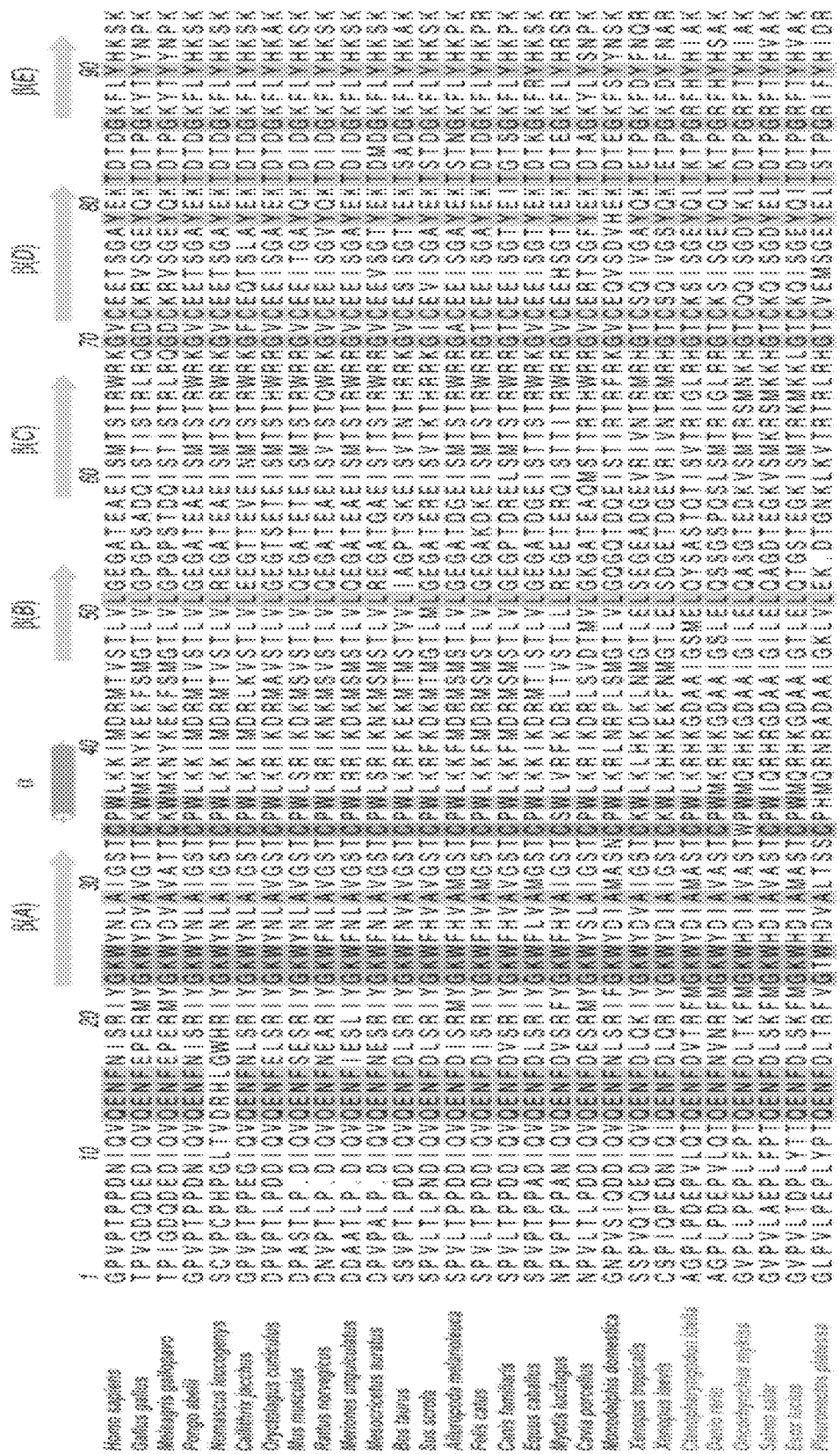
Figure 5B:
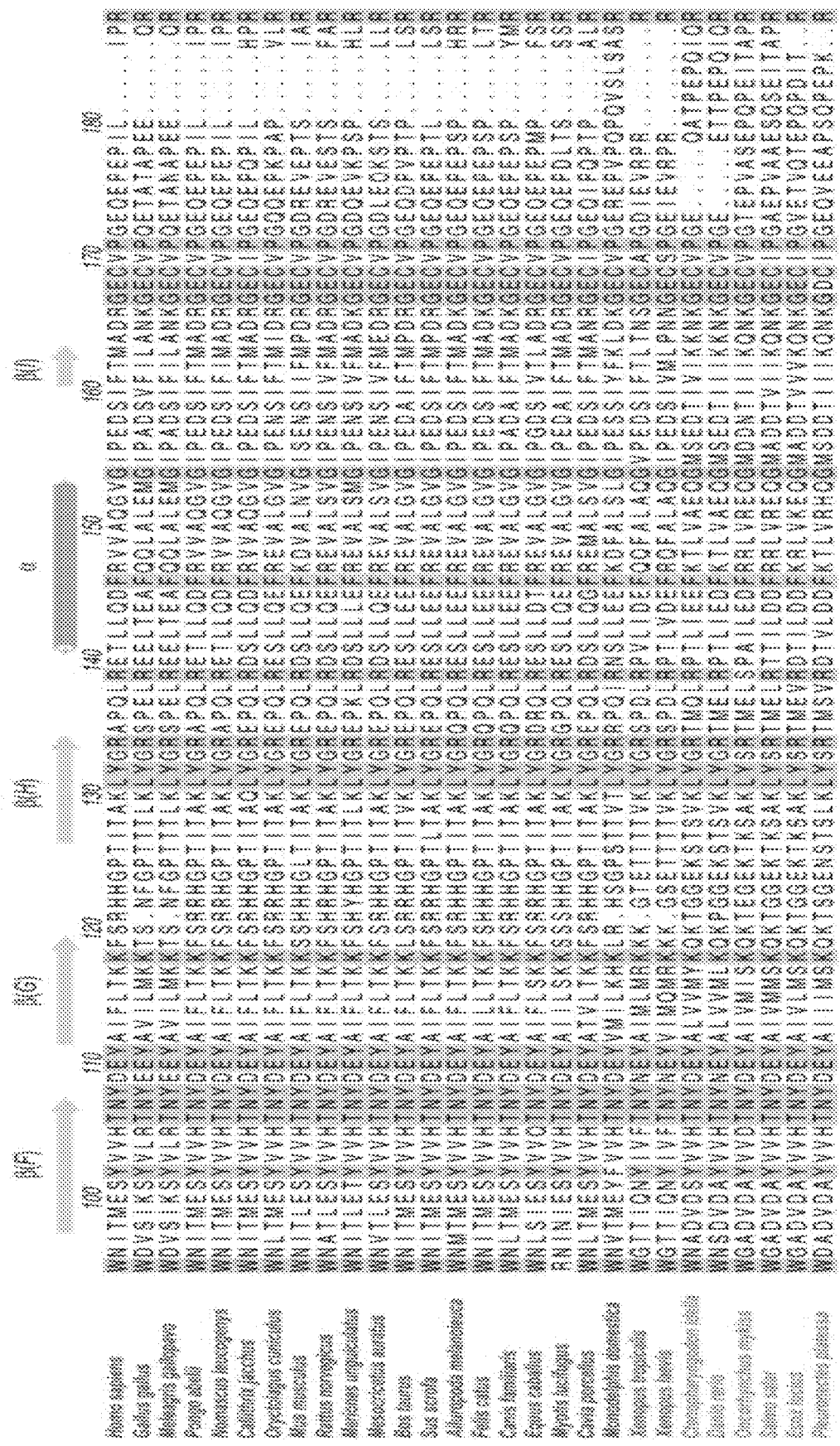

FIGS. 5A-5B. Multiple alignment of 29 orthologous sequences of human AMBP (UniProt ID: P02760) from various vertebrate species calculated by Uniprot BLAST.

Sequences with a score lower than 350 as well as preliminary data were omitted. Only residues 1-184 of the mature human a1m protein (first line), corresponding to positions 20-202 of the translated human AMBP gene, were included. Taxonomic classes are labeled by colors: blue (mammals), red (amphibia), and green (fish). Secondary structure elements of a1m are indicated with pink (α-helices) and green (β-strands) symbols above its sequence. Residues with a degree of conservation of more than 95% are highlighted in gray, except for Gly23-Trp25 (cyan), Cys34 (orange), Cys72 (yellow) and Cys169 (yellow). The trivial names and the corresponding UniProt IDs (in parentheses) are: *Gallus gallus*: chicken (F1NUF8) (SEQ ID NO: 25), *Meleagris gallopavo*: common turkey (G1MR91) (SEQ ID NO: 26), *Pongo abelii*: sumatran orangutan (Q5NVR3) (SEQ ID NO: 27), *Nomascus leucogenys*: northern white-cheeked gibbon (G1S4D1) (SEQ ID NO: 28), *Callitrix jacchus*: white-tufted-ear marmoset (F6R1P3) (SEQ ID NO: 29), *Oryctolagus cuniculus*: rabbit (G1TSY8) (SEQ ID NO: 30), *Mus musculus*: mouse (Q07456) (SEQ ID NO: 31), *Rattus norvegicus*: rat (Q64240) (SEQ ID NO: 32), *Meriones unguiculatus*: mongolian jird (Q62577) (SEQ ID NO: 33), *Mesocricetus auratus*: golden hamster (Q60559) (SEQ ID NO: 34), *Bos taurus*: bovine (P00978) (SEQ ID NO: 35), *Sus scrofa*: pig (P04366) (SEQ ID NO: 36), *Ailuropoda melanoleuca*: giant panda (G1M2K1) (SEQ ID NO: 37), *Felis catus*: cat (E1CJT2) (SEQ ID NO: 38), *Canis familiaris*: dog (E2R796) (SEQ ID NO: 39), *Equus caballus*: horse (F6UZH0) (SEQ ID NO: 40), *Myotis lucifugus*: little brown bat (G1PCS2) (SEQ ID NO: 41), *Cavia porcellus*: guinea pig (O70160) (SEQ ID NO: 42), *Monodelphis domestica*: gray short-tailed gray opossum (F7D6H6) (SEQ ID NO: 43), *Xenopus tropicalis*: western clawed frog (Q6P2V8) (SEQ ID NO: 44), *Xenopus laevis*: african clawed frog (P70004) (SEQ ID NO: 45), *Ctenopharyngodon idella*: Grass carp (A8VZJ0) (SEQ ID NO: 46), *Danio rerio*: zebrafish (A7E2Q2) (SEQ ID NO: 47), *Oncorhynchus mykiss*: rainbow trout (Q5F4T3) (SEQ ID NO: 48), *Salmo salar*: atlantic salmon (B5XD04) (SEQ ID NO: 49), *Esox lucius*: northern pike (C1BWU5) (SEQ ID NO: 50), *Pleuronectes platessa*: european plaice (P36992) (SEQ ID NO: 51). *Homo sapiens*: human is shown in SEQ ID NO: 1.

Figure 6:
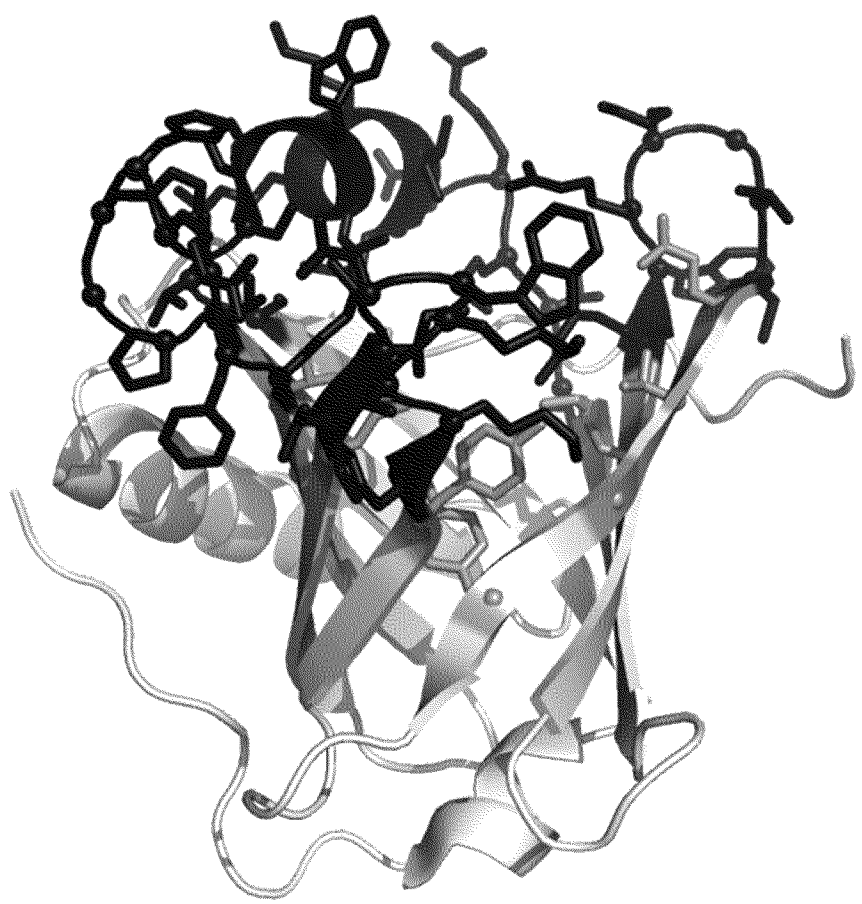

FIG. 6. A graphical illustration of the residues in a1m highlighted to be considered for randomization.

a) Residues depicted in dark gray: a set of residues that corresponds to the generic set of four structurally variable loops at the entrance to the lipocalin ligand pocket (according to Skerra, BBA 2000);

b) Residues depicted in light gray: an additional set of "second layer" residues whose side chains protrude into the ligand pocket underneath the exposed loops.

FIG. 7. A model of a1m binding to Lu-DOTA-Bn conjugated to Biotin via a PEG4 linker.

Figure 7A:
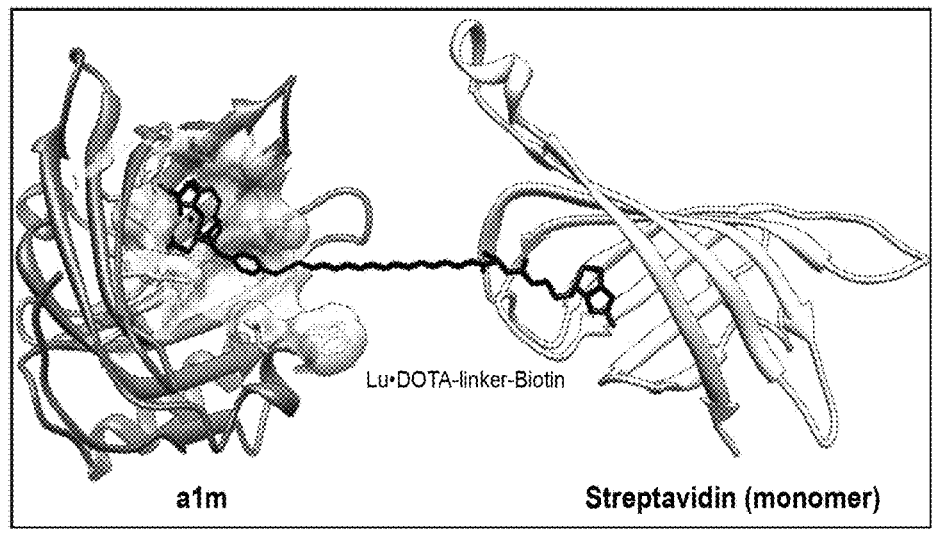

FIG. 7A Illustration of simultaneous binding of Lu-DOTA-Bn-Linker-Biotin (black) by a1m (PDB code 3QKG) and a Streptavidin monomer (PDB code 3RY2), that occurs during phage display selection. Linker length was a critical parameter to prevent sterical hindrance of a1m and Streptavidin during simultaneous binding of the target.

Figure 7B:
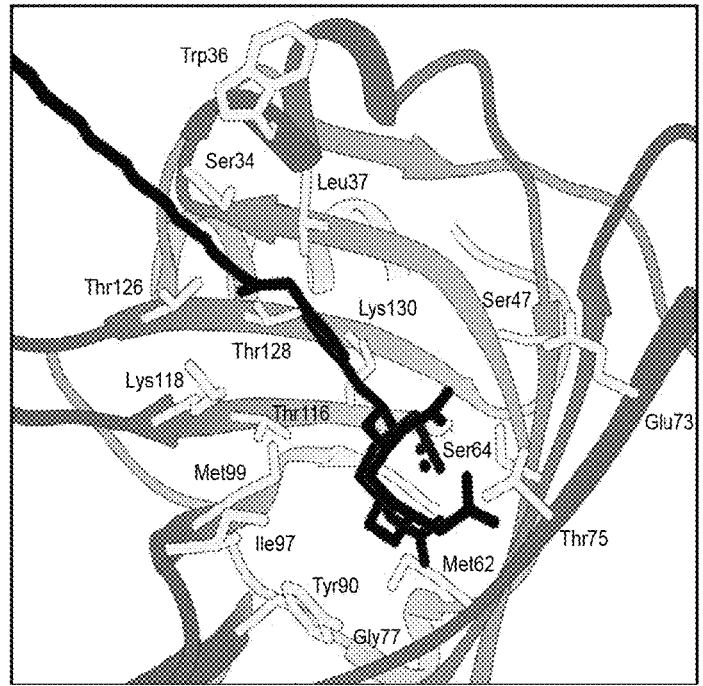

FIG. 7B View into the cavity of a1m with a model of bound Lu-DOTA-Bn. The most prominent position of Lu-DOTA-Bn in the cavity revealed from docking experiments using the UCSF Chimera tool Chil2 was used for the construction of the a1m library. Amino acid positions chosen for random mutagenesis are indicated as sticks.

Figure 8A:
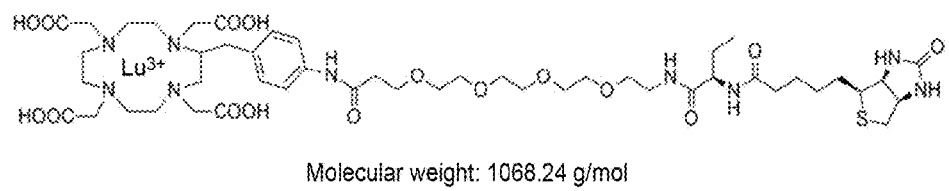
Figure 8B:
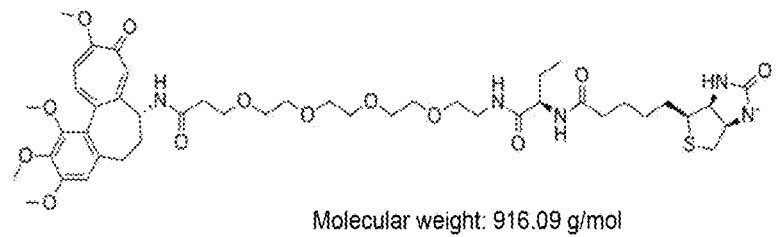

FIGS. 8A-8B. Representative non-nature ligands can be bound by a1m muteins FIGS. 8A-8B show targets of Lu-DOTA-Bn-dPEG4-Biotin and Colchicine-dPEG4-Biotin that were used for selection of a1m muteins against the respective target.

FIG. 9. Biochemical characteristics of a1m muteins containing amino acid substitution due to insertion of first BstXI restriction site for library cloning in comparison to wild-type human a1m.

Figure 9C:
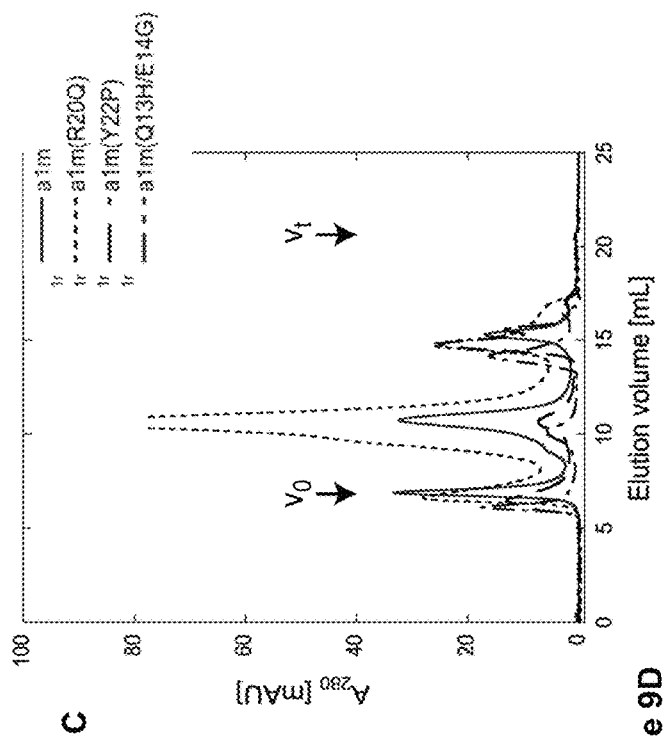
Figure 9D:
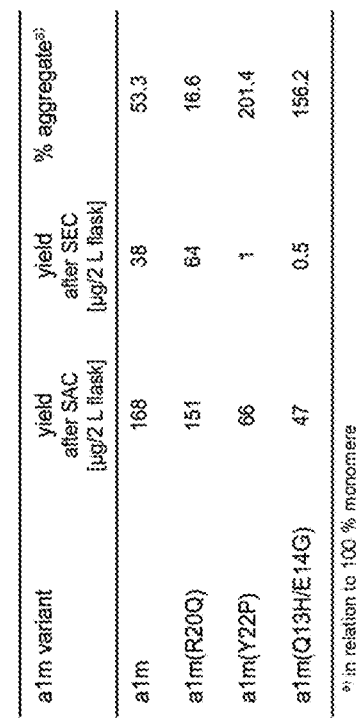
Figure 9A:
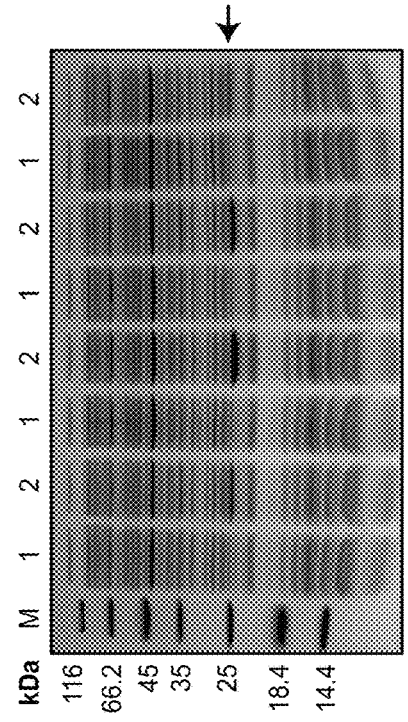

FIG. 9A Coomassie-stained 15% SDS-PAGE analysis of whole cell extracts (1) before and (2) after induction of protein production for a1m and muteins derived therefrom under reducing conditions. TG1/F− cells transformed with the expression plasmid pa1m2 containing the indicated amino acid substitution were grown in LB-Amp medium until an OD550 of 0.5 was reached. The periplasmic protein production was with addition of 0.2 μg/ml aTc (anhydrotetracycline) for 3 h, followed by periplasmic protein extraction. M represents the molecular weight marker with the corresponding band sizes in kDa displayed on the left of the gel. Bands of an estimated molecular weight of 22 kDa corresponding to a1m muteins are marked by an error.

Figure 9B:
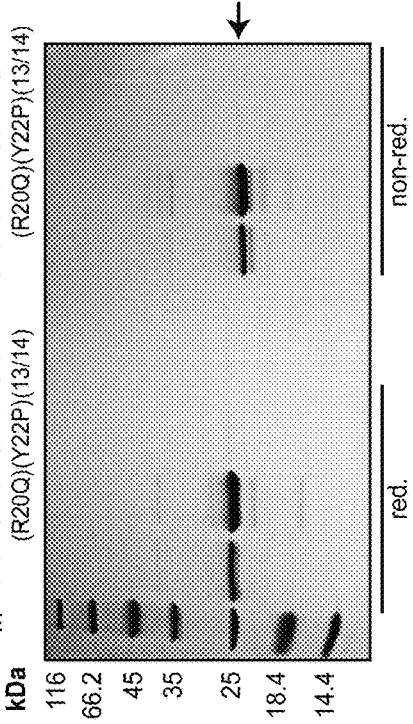

FIG. 9B Size exclusion chromatography (SEC) profiles of a1m and muteins derived therefrom. Proteins were subjected to Streptavidin-affinity chromatography (SAC) prior to SEC using PBS as running buffer and an analytical grade Superdex 75 HR 10/30 column. Peak intensities differed depending on the expression yield of the particular mutein.

FIG. 9C Coomassie-stained 15% SDS-PAGE analysis of soluble, monodisperse a1m and muteins derived therefrom under reducing and non-reducing conditions after SEC.

FIG. 9D Comparison of protein yields after SAC and SEC of a1m and muteins derived therefrom determined by measurement of absorbance at 280 nm. Portion of aggregated protein after SEC was calculated in relation to 100% monomer. R20Q mutation increased expression level and monomer: aggregate ratio compared to wild-type human a1m.

FIG. 10. PCR assembly strategy for the simultaneous random mutagenesis

FIG. 10A illustrates the polymerase chain reaction (PCR) assembly strategy for the simultaneous random mutagenesis of the 17 amino acid positions 34, 36, 37, 47, 62, 64, 73, 75, 77, 90, 97, 99, 116, 118, 126, 128, and 130 (underlined and numbered) in the amino acid sequence of a1m. Whenever possible, codons optimized for *E. coli* expression were used throughout for the non-mutated amino acid positions within the BstXI cassette since a1m gene was cloned from human AMBP gene (Swiss-Prot ID: AMBP_HUMAN; UniProt ID: P02760, corresponding to the human mature a1m sequence (without the valine residue at position 203 of AMBP)

(Meining & Skerra (2012) *Biochem J*. 445, 175-182). The 17 positions were divided into four sequence subsets. For randomization of the amino acids in each subset an oligodeoxynucleotide was synthesized (SEQ ID NO: 2, SEQ ID NO: 3, SEQ ID NO: 4 and SEQ ID NO: 5) wherein a mixture of 19 different triplets i.e. all amino acids except cysteine (AAA, AAC, ACT, ATC, ATG, CAG, CAT, CCG, CGT, CTG, GAA, GAC, GCT, GGT, GTT, TAC, TCT, TGC, TGG, TTC) were employed at the mutated codons. Each trimer indicated by XXX encodes for a different amino acid except Cys. Four additional oligodeoxynucleotides (SEQ ID NO: 6, SEQ ID NO: 7, SEQ ID NO: 8 and SEQ ID NO: 9) with fixed nucleotide sequences corresponding to the noncoding strand (written below the DNA double strand sequence in 3'-5' direction) and filling the gaps between the aforementioned oligodeoxynucleotides were also used in the assembly reaction. Two flanking oligodeoxynucleotides (SEQ ID NO: 10 and SEQ ID NO: 11), which were added in excess and carried biotin groups at their 5'-end, served as primers for the PCR amplification of the assembled, entirely synthetic gene fragment. The two flanking primers each encompassed a BstXI restriction site, giving rise to mutually non-compatible overhangs upon enzyme digest. This special arrangement of restriction sites enabled a particularly efficient ligation and cloning of the synthetic gene. Substitution of the amino acid Arg20 to Gln with respect to the original a1m sequence was necessary to introduce the first BstXI restriction site, while the insertion of the second one was possible without altering the amino acid sequence. Additionally, amino acid Trp95 was replaced by His for removal of a solvent-exposed, hydrophobic residue, and His122 was substituted by Gln preventing complexion of metal-ion with the neighbouring His123. Furthermore, the unpaired residue Cys34 was replaced by Ser in order to prevent unwanted disulfide formation. After one pot PCR the resulting gene fragment was inserted into a vector providing the missing parts of the a1m structural gene. FIG. 10A discloses SEQ ID NOS 10, 2, 62, 64, 3, 60, 6, 4, 5, 61, 7, 8, 9 and 11, respectively, in order of appearance.

Figure 10B:
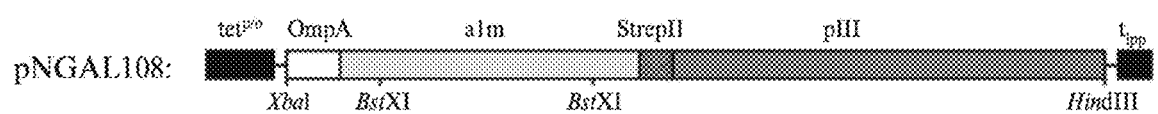

FIG. 10B Design of the vector pNGAL108 for phage display selection of a1m muteins. This plasmid is based on the generic *E. coli* expression vector pASK75, which harbors for the tetracycline promoter/operator for tightly regulated transcriptional control. The tet$^{o/o}$ is chemically inducible with anhydrotetracycline. The a1m expression cassette encompasses an N-terminal OmpA signal peptide for periplasmic secretion, the mature part of the engineered lipocalin, the Strep-tag II for affinity purification, followed by the gene III minor coat protein of filamentous bacteriophage M13 for phage display selection.

Figure 11A:
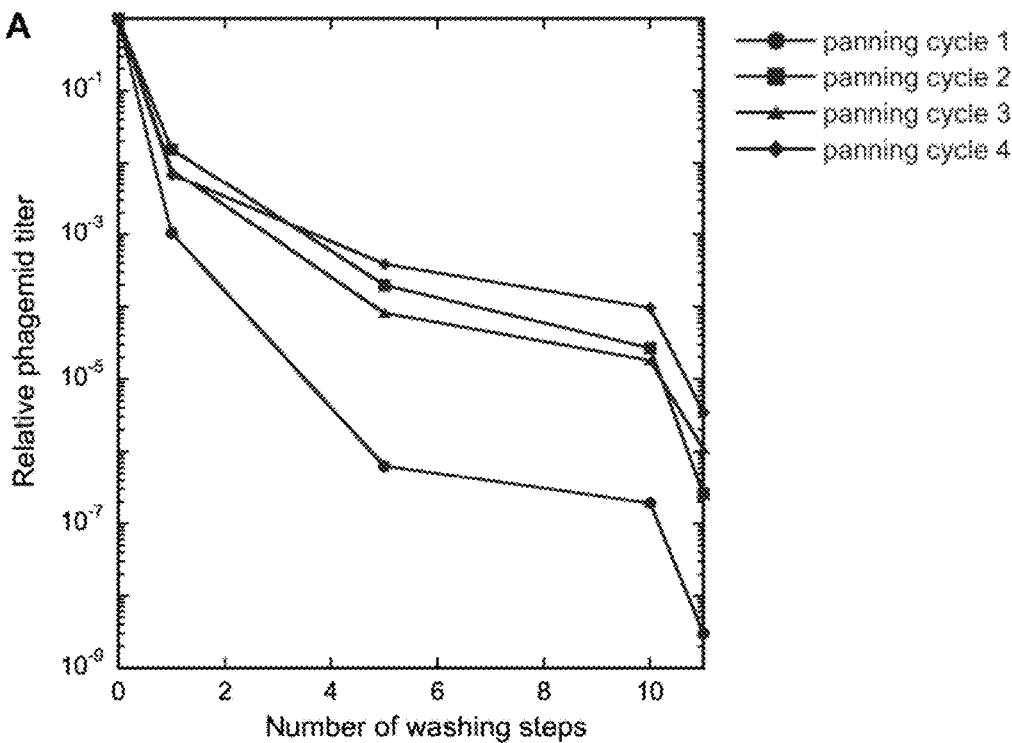
Figure 11B:
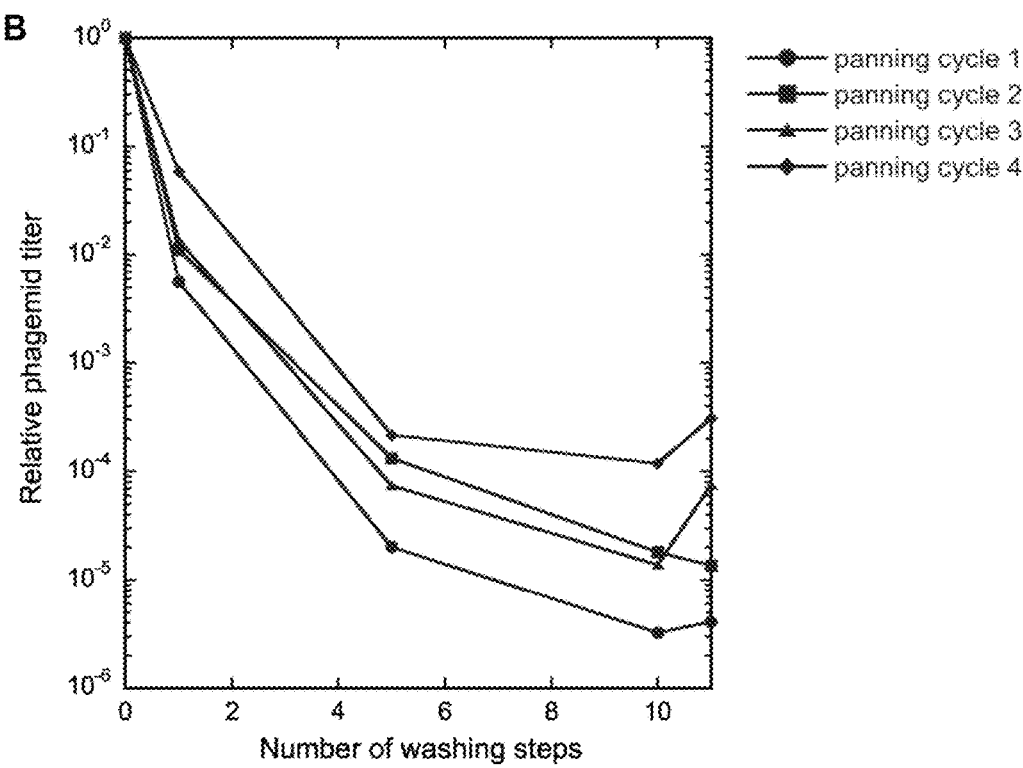

FIG. 11. An overlay of elution profiles revealed from phage display selection after cycles 1-4 of a1m muteins specific for Lu-DOTA-Bn (FIG. 11A) or Colchicine (FIG. 11B) starting from a synthetic combinatorial library with 17 randomized positions.

Following an on-bead panning strategy, 100 nM of the biotinylated target was adsorbed onto Streptavidin- or NeutrAvidin-coated magnetic particles prior to the incubation with about $10^{13}$ phagemids for 2 h in panning cycle 1 and for 1 h in panning cycles 2-4, respectively. After 10 washing steps with PBS/0.1T containing 0.1 mM D-Desthiobiotin, specifically bound phagemids were eluted under competitive condition using 100 µM of unbiotinylated target. The phagemid titer of certain wash fractions and the elution fraction were determined and plotted semi-logarithmically as fractional amount of totally applied phagemids of each panning cycle (relative phagemid titer). The eluted phagemids were then amplified and subjected to the next panning cycle.

FIG. 12. Results of the screening ELISA for identification of Lu-DOTA-Bn-specific a1m muteins after the fourth panning cycle.

Figure 12A:
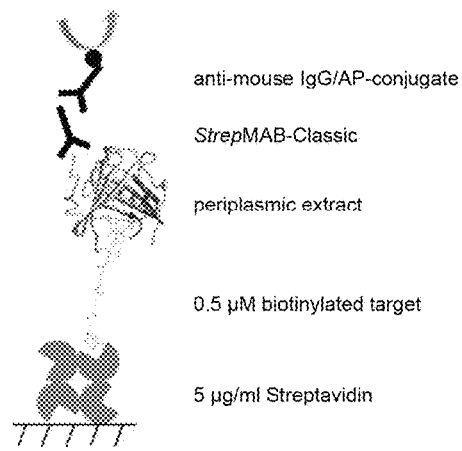

FIG. 12A shows the experimental set-up for the ELISA. The BstXI cassette of the enriched phagemid pool was subcloned into the expression plasmid pa1m2, which encodes a fusion of the OmpA signal peptide for the periplasmic production in *E. coli* and the a1m coding region with the C-terminal Strep-tag II. Small-scale expression of randomly picked, single clones of a1m was performed in TG1/F⁻ overnight at 20° C., followed by release of recombinant protein from the bacterial periplasm using BBS (borate buffered saline) buffer supplemented with 1 mg/ml lysozyme. The periplasmic extract was then applied to a 96-well Maxisorp plate, which was coated with 5 µg/ml Streptavidin and incubated with 0.5 µM biotinylated Lu-DOTA-Bn. Target-bound muteins were detected using the murine anti Strep-tag-II monoclonal antibody Strep-MAB-Classic, which in turn was bound by an anti-mouse IgG (Fc-specific)/alkaline phosphatase-conjugate. Signal development upon addition of p-nitrophenyl phosphate was followed by measuring the absorption at 405 nm in a Spectra-Max 250 reader for up to 1.5 h.

Figure 12B:
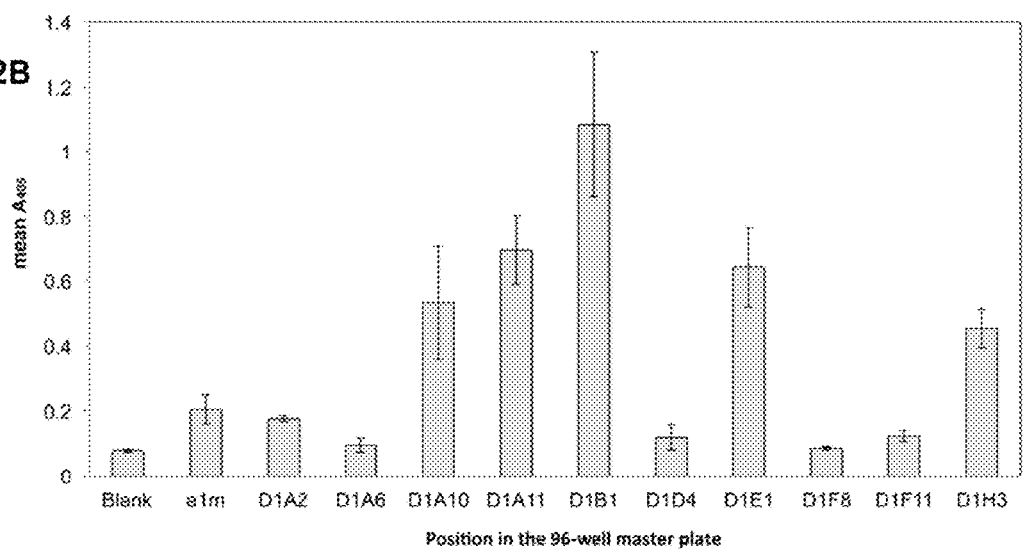

FIG. 12B Histogram representing the measured absorptions at 405 nm for certain a1m muteins. For explicit numbering of the analyzed clones, the prefix D1 was used to indicate them as Lu-DOTA-Bn-specific Anticalins, followed by the position in the 96-well master plate.

Figure 12C:
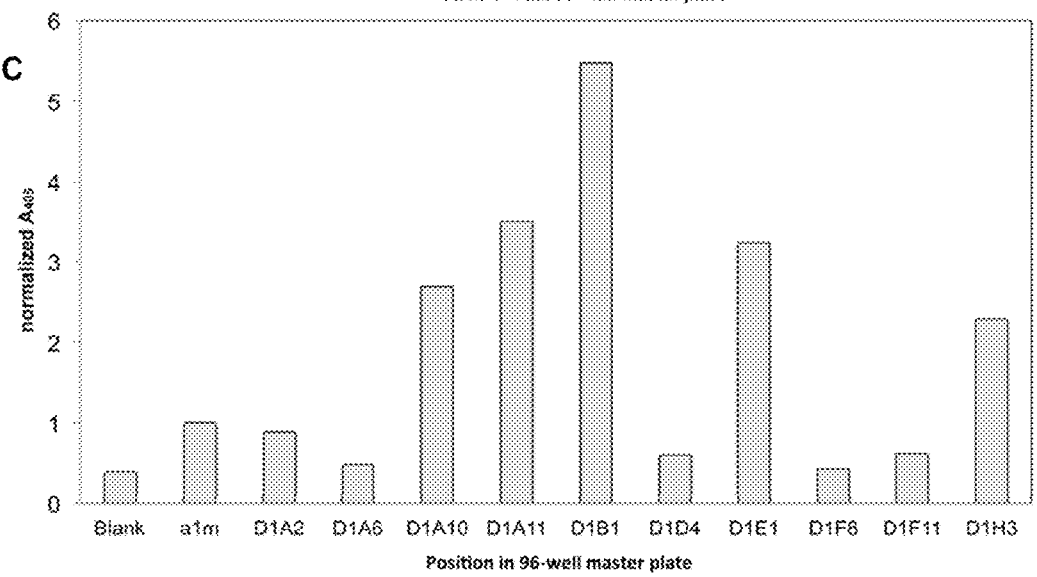

FIG. 12C Histogram representing the measured absorptions at 405 nm for certain a1m muteins, which were normalized for the a1m signal. For explicit numbering of the analyzed clones, the prefix D1 was used to indicate them as Lu-DOTA-Bn-specific muteins, followed by the position in the 96-well master plate.

FIG. 13. illustrates an amino acid sequence alignment of the Lu-DOTA-Bn-specific a1m muteins D1A10 (SEQ ID NO: 12), D1A11 (SEQ ID NO: 13), D1B1 (SEQ ID NO: 14, D1E1 (SEQ ID NO: 15), and D1H3 (SEQ ID NO: 16) with wild-type human a1m. Randomized positions are marked by an x. Lower case letters indicate conserved amino acid substitutions to introduce a pair of unique BstXI restrictions site (R20Q), to remove a tryptophane residue from the proteins surface (W95H) and to prevent metal complexation through by two histidine residues (H122Q). The eight structurally conserved β-strands (A-H) and the four structurally variable loops (#1-4) are labeled. Dots represent amino acids identical to the wild-type human a1m sequence (SEQ ID NO: 1). FIG. 13 discloses the "Library" sequence as SEQ ID NO: 65.

FIG. 14. Results of the screening ELISA for identification of Colchicine-specific a1m muteins after the fourth panning cycle.

Figure 14A:
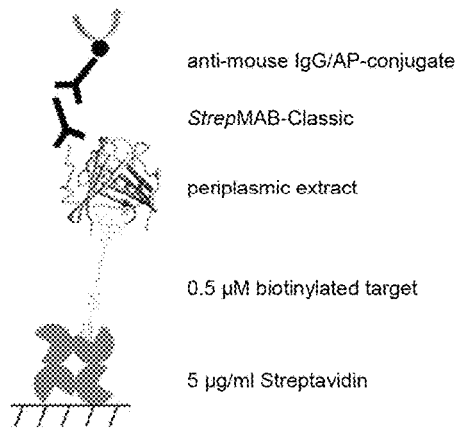

FIG. 14A shows the experimental set-up for the ELISA. The BstXI cassette of the enriched phagemid pool was subcloned into the expression plasmid pa1m2, which encodes a fusion of the OmpA signal peptide for the periplasmic production in *E. coli* and the a1m coding region with the C-terminal Strep-tag II. Small-scale expression of randomly picked, single clones of a1m was performed in TG1/F⁻ overnight at 20° C., followed by release of recombinant protein from the bacterial periplasm using BBS (borate buffered saline) buffer supplemented with 1 mg/ml lysozyme. The periplasmic extract was then applied to a 96-well Maxisorp plate, which was coated with 5 µg/ml Streptavidin and incubated with 0.5 µM biotinylated Lu-DOTA-Bn. Target-bound muteins were detected using the murine anti Strep-tag-II monoclonal antibody Strep-MAB-Classic, which in turn was bound by an anti-mouse IgG (Fc-specific)/alkaline phosphatase-conjugate. Signal development upon addition of p-nitrophenyl phosphate was followed by measuring the absorption at 405 nm in a Spectra-Max 250 reader for up to 1.5 h.

Figure 14B:
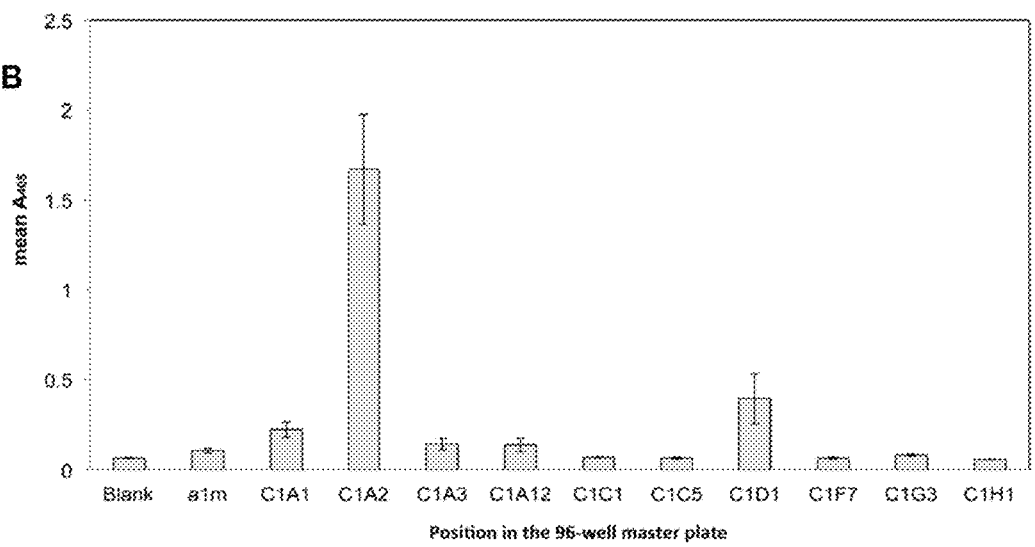

FIG. 14B Histogram representing the measured absorptions at 405 nm for certain a1m muteins. For explicit numbering of the analyzed clones, the prefix C1 was used to indicate them as Colchicine-specific Anticalins, followed by the position in the 96-well master plate.

Figure 14C:
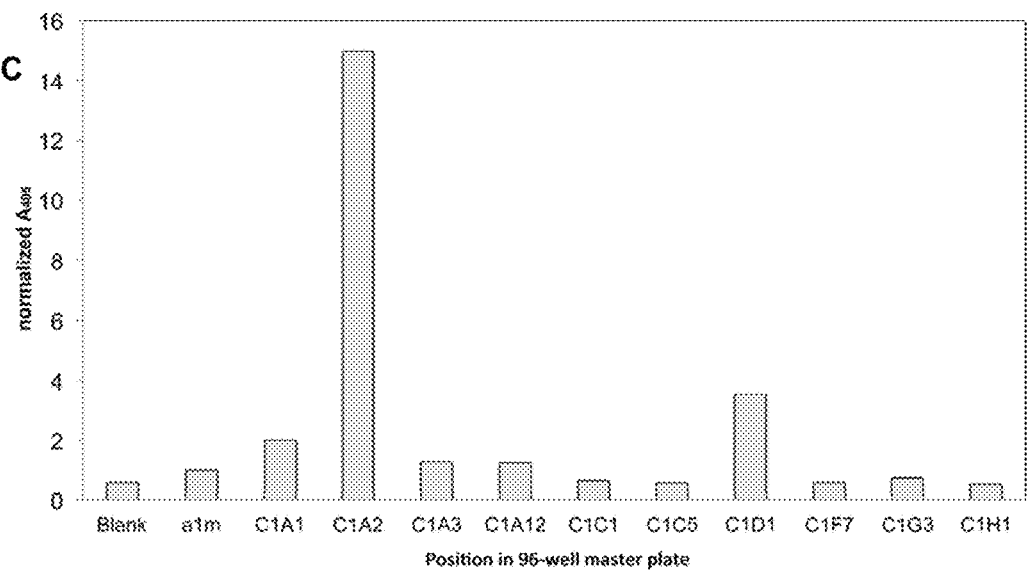

FIG. 14C Histogram representing the measured absorptions at 405 nm for certain a1m muteins, which were normalized for the a1m signal. For explicit numbering of the analyzed clones, the prefix C1 was used to indicate them as Colchicine-specific muteins, followed by the position in the 96-well master plate.

FIG. 15. illustrates an amino acid sequence alignment of the Colchicine-specific a1m muteins C1A1 (SEQ ID NO: 17), C1A2 (SEQ ID NO: 18) and C1D1 (SEQ ID NO: 19) with wild-type human a1m. Randomized positions are marked by an x. Lower case letters indicate conserved amino acid substitutions to introduce a pair of unique BstXI restrictions site (R20Q), to remove a tryptophane residue from the proteins surface (W95H) and to prevent metal complexation through by two histidine residues (H122Q). The eight structurally conserved β-strands (A-H) and the four structurally variable loops (#1-4) are labeled. Dots represent amino acids identical to the wild-type human a1m sequence (SEQ ID NO: 1). FIG. 15 discloses the "Library" sequence as SEQ ID NO: 66.

DETAILED DESCRIPTION

The present inventors have elucidated the secondary and tertiary structure of human a1m lipocalin and potential target-binding sites thereof. Accordingly, the present disclosure provides a collection of amino acid sequence members comprised of muteins of a1m polypeptide or a functional homologue thereof wherein the amino acid sequence of said members differs from the a1m polypeptide at one or more of the sequence positions of the wild type a1m polypeptide. These differences may correspond to the sequence positions in the four peptide loops #1, #2, #3 and #4 of human a1m polypeptide. The collection of amino acid sequence members can range in size from at least 10^2, at least 10^3, at least 10^4, at least 10^5, at least 10^6, at least 10^7, at least 10^8, at least 10^9, at least 10^10 and at least 10^11.

The members of this collection have at least 60% sequence identity with human a1m. This includes all proteins that have a sequence homology or identity of more than 60%, 70%, 80%, 85%, 90% or 95% in relation to the human mature a1m sequence (amino acid residues 20-203 of the translated human AMBP gene (Swiss-Prot ID: AMBP_HUMAN, UniProt ID: P02760; SEQ ID NO: 1).

In a preferred embodiment, at least one of said members can specifically bind to a target other than a target to which wild-type a1m binds and has no or no substantial binding affinity for an endogenous a1m target. For example, an endogenous target of a1m can be retinoic acid or retinol. Preferably, the a1m lipocalin muteins disclosed herein do not specifically bind retinoic acid or retinol in an assay as described in Breustedt, D. A., Schönfeld, D. L & Skerra, A. (2006) Comparative ligand-binding analysis of ten human lipocalins (Biochim. Biophys. Acta 1764, 161-173). In a more preferred embodiment, at least one of said members can specifically bind to two targets other than a target to which wild-type a1m binds (e.g. Colchicine and Lutetium (177Lu) DOTA-TATE ((177)Lu-DOTA)); in this sense, a member contains two binding sites. As used herein, a "target" is defined as any molecule to which an a1m mutein polypeptide of the disclosure is capable of specifically binding, including all types of proteinaceous and non-proteinacious molecules such as haptens or other small molecules. As used herein, a polypeptide of the disclosure "specifically binds" a target if it is able to discriminate between that target and one or more reference targets, since binding specificity is not an absolute, but a relative property. "Specific binding" can be determined, for example, in accordance with Western blots, ELISA, RIA-, ECL-, IRMA-tests, FACS, IHC and peptide scans. The polypeptide of the disclosure can bind to the target with an affinity in the micromolar or, in more preferred embodiments, in the nanomolar range. Binding constants of less than 100 µM, 50 µM, 500 nM, 250 nM, 100 nM and 50 nM are also envisioned in the current disclosure.

"Wild-type a1m", when used herein, means the human mature a1m sequence (amino acid residues 20-203 of the translated human AMBP gene (Swiss-Prot ID: AMBP_HUMAN, UniProt ID: P02760; SEQ ID NO: 1). The wild-type a1m does preferably not contain a mutation in any one of the loops #1, #2, #3 and #4 as described herein. Whereas a "mutein of a1m" or "mutein a1m" or the like terms does contain at least one mutation in any one of the loops #1, #2, #3 and #4 as described herein in comparison to wild-type a1m. Loop #1 comprises preferably amino acids 29-48, loop #2 comprises preferably amino acids 63-80, loop #3 comprises preferably amino acids 89-100 and loop #4 comprises preferably amino acids 115-129 of human mature a1m sequence. More preferably loop #1 comprises amino acids 32-46 of mature a1m. More preferably loop #2 comprises amino acids 66-72 of mature a1m. More preferably loop #3 comprises amino acids 91-98 of human mature a1m sequence. More preferably loop #4 comprises amino acids 118-126 of mature human mature a1m sequence.

The present disclosure also teaches a method of producing (i.e. isolating) a mutein of human a1m polypeptide or a functional homologue thereof, which specifically binds a target other than a target to which wild-type a1m binds, comprising the steps of: (i) screening the members of the collection with a target other than a target to which wild-type a1m binds in order to allow formation of a complex between said target and at least one of said members, (ii) removing muteins having no or no substantial binding affinity for the target; and (iii) isolating the mutein specifically binding to the target.

The disclosed crystal structure of human a1m polypeptide (see Example 1) serves as basis for the finding that a1m and a functional homologue thereof can provide suitable scaffolds for the generation of polypeptides having binding activity to a given target of interest. The amino acid positions which are subjected to mutagenesis are distributed across four sequence segments corresponding to four loops in the three-dimensional structure of a1m. The number of the segments (loops) defined above which are used for mutagenesis can vary. It is not necessary to mutate more than one of these four loops, for example, in a concerted mutagenesis, but it is also possible to subject only one, two or three of the loops to generate a mutein having detectable affinity to a given target of interest.

In one embodiment of the disclosed method, human a1m polypeptide may be subjected to mutagenesis at one of the sequence positions which correspond to the linear polypeptide sequence positions 29-48, 63-80, 89-100, and 115-129 of human a1m polypeptide. In a preferred embodiment of the disclosed method, human a1m polypeptide is subjected to mutagenesis at one of the sequence positions which correspond to the sequence positions 32-46, 66-72, 91-98, and 118-126 of human a1m polypeptide. In a more preferred embodiment of the disclosed method, human a1m polypeptide is subjected to mutagenesis at one of the sequence positions which correspond to the linear polypeptide sequence positions 34-37, 62-64, 97-99, 116-118, and 126-130 of human a1m polypeptide.

In a still further embodiment of the disclosed method, the human a1m polypeptide is subject to further mutagenesis at one of the sequence positions which correspond to the linear polypeptide sequence positions 30, 47, 73, 75, 77, 79 and 90 of human a1m polypeptide.

Accordingly, in one embodiment the disclosure provides an a1m mutein that may contain a mutation at any one of the sequence positions which correspond to the linear polypeptide sequence positions 29-48, 63-80, 89-100, and 115-129 of human a1m polypeptide. In a preferred embodiment, an a1m mutein of the disclosure contains a mutation at any one of the sequence positions which correspond to the linear polypeptide sequence positions 32-46, 66-72, 91-98, and 118-126 of human a1m polypeptide. In a further embodiment, an a1m mutein of the disclosure contains a mutation at one or more of the sequence positions which correspond to the linear polypeptide sequence positions 34-37, 62-64, 97-99, 116-118, and 126-130 of human a1m polypeptide. In a still further embodiment, the a1m mutein further contains a mutation at one of the sequence positions which correspond to the linear polypeptide sequence positions 30, 47, 73, 75, 77, 79 and 90 of human a1m polypeptide.

As provided in the current disclosure, an a1m mutein is preferably a polypeptide in which one or more amino acids within one, two, three, or all four loops are changed in comparison to a wild-type (or reference) a1m of the present disclosure (e.g. human a1m polypeptide). Said one or more amino acids include 1, 2, 3, 4, 5, 6, 7, 8, 9, 10, 11, 12, 13, 14, 15, 16, 17, 18, 19, 20 or more amino acids that can be changed in loop #1, loop #2, loop #3 and/or loop #4.

However, it is also envisaged that, within loop #1 1, 2, 3, 4, 5, 6, 7, 8, 9, 10, 11, 12, 13, 14 or 15 amino acids; within loop #2 1, 2, 3, 4, 5, 6 or 7 amino acids; within loop #3 1, 2, 3, 4, 5, 6, 7 or 8 amino acids; and/or within loop #4 1, 2, 3, 4, 5, 6, 7, 8 or 9 amino acids can be replaced.

Preferably, it is also envisaged that within loop #1 1, 2, 3, 4, 5, 6, 7, 8, 9, 10, 11, 12, 13, 14, 15, 16, 17, 18, 19 or 20 amino acids; within loop #2 1, 2, 3, 4, 5, 6, 7, 8, 9, 10, 11, 12, 13, 14, 15, 16, 17 or 18 amino acids; within loop #3 1, 2, 3, 4, 5, 6, 7, 8, 9; 10, 11 or 12 amino acids; and/or within loop #4 1, 2, 3, 4, 5, 6, 7, 8, 9, 10, 11, 12, 13, 14 or 15 amino acids can be replaced.

"Replacement", when used herein, means that an amino acid different from that present at the corresponding position in the wild type a1m lipocalin is present in an a1m lipocalin mutein of the present disclosure.

The term "position", when used in the present disclosure, means the position of either an amino acid within an amino acid sequence depicted herein or the position of a nucleotide within a nucleic acid sequence depicted herein. The term "corresponding" as used herein also includes that a position is not only determined by the number of the preceding nucleotides/amino acids. Accordingly, the position of a given amino acid in accordance with the disclosure which may be substituted may vary due to deletion or addition of amino acids elsewhere in a (mutant or wild-type) lipocalin. Similarly, the position of a given nucleotide in accordance with the present disclosure which may be substituted may vary due to deletions or additional nucleotides elsewhere in a mutein or wild type a1m 5'-untranslated region (UTR) including the promoter and/or any other regulatory sequences or gene (including exons and introns).

Thus, under a "corresponding position" in accordance with the present disclosure it is preferably to be understood that nucleotides/amino acids may differ in the indicated number but may still have similar neighbour ring nucleotides/amino acids. Said nucleotides/amino acids which may be exchanged, deleted or added are also comprised by the term "corresponding position". When used herein "at a position corresponding to a position" a position in a "query" (or reference) amino acid (or nucleotide) sequence is meant that corresponds to a position in a "subject" amino acid (or nucleotide) sequence. A preferred query (or reference) sequence is shown in SEQ ID NO: 1.

Specifically, in order to determine whether a nucleotide residue or amino acid residue of the amino acid sequence of an a1m different from an a1m mutein of the disclosure corresponds to a certain position in the nucleotide sequence or the amino acid sequence of an a1m mutein as described, a skilled artisan can use means and methods well-known in the art, e.g., alignments, either manually or by using computer programs such as BLAST 2.0 (Altschul et al. (1990), J. Mol. Biol. 215:403-10), which stands for Basic Local Alignment Search Tool, or ClustalW (Thompson et al. (1994), Nucleic Acids Res. 22(22):4673-80) or any other suitable program which is suitable to generate sequence alignments. Accordingly, wild-type a1m (SEQ ID NO: 1) can serve as "subject sequence", while the amino acid sequence of an a1m different from a1m as described herein serves as "query sequence".

Given the above, a skilled artisan is thus readily in a position to determine which amino acid position mutated in a1m as described herein corresponds to an amino acid of an a1m scaffold other than a1m. Specifically, a skilled artisan can align the amino acid sequence of a mutein as described herein, in particular an a1m mutein of the disclosure with the amino acid sequence of a different a1m to determine which amino acid(s) of said mutein correspond(s) to the respective amino acid(s) of the amino acid sequence of said different lipocalin.

When used herein, a "mutein," a "mutated" entity (whether protein or nucleic acid) or "mutant" refers to the exchange, deletion, or insertion of one or more nucleotides or amino acids, respectively, within the a1m of the present disclosure compared to the wild-type (naturally occurring) nucleic acid or protein "reference" scaffold of a1m, for example, shown in SEQ ID NO: 1.

Accordingly, an a1m mutein of the present disclosure may include the wild type (natural) amino acid sequence of the "parental" protein scaffold (human a1m) outside the mutated one or more amino acid sequence positions within one, two, three or four loop(s); alternatively, an a1m mutein may also contain amino acid mutations outside the sequence positions subjected to mutagenesis that do not interfere with the binding activity and the folding of the mutein. Such mutations can be accomplished on a DNA level using established standard methods. In a preferred embodiment, possible alterations of the amino acid sequence are insertions or deletions as well as amino acid substitutions. Such substitutions may be conservative, i.e. an amino acid residue is replaced with a chemically similar amino acid residue. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan. One the other hand, it is also possible to introduce non-conservative alterations in the amino acid sequence. In addition, instead of replacing single amino acid residues, it is also possible to either insert or delete one or more continuous amino acids of the primary structure of a parental protein scaffold, where these deletions or insertion result in a stable folded/functional mutein, which can be readily tested by the skilled artisan.

Moreover, the skilled artisan will appreciate methods useful to prepare protein muteins contemplated by the present disclosure but whose protein or nucleic acid sequences are not explicitly disclosed herein. As an overview, such modifications of the amino acid sequence can include, e.g., directed mutagenesis of single amino acid positions in order to simplify sub-cloning of a mutated lipocalin gene or its parts by incorporating cleavage sites for certain restriction enzymes. In addition, these mutations can also be incorporated to further improve the affinity of a lipocalin mutein for a given target. Furthermore, mutations can be introduced to modulate certain characteristics of the mutein such as to improve folding stability, serum stability, protein resistance or water solubility or to reduce aggregation tendency, if necessary. For example, naturally occurring cysteine residues may be mutated to other amino acids to prevent disulphide bridge formation.

When used herein, "a1m", in which one or more amino acid replacements, in particular at one or more position in one, two, three or all four loops, are made in accordance with the teaching of the present disclosure, encompasses any other a1m known in the art or which can be identified by using wide-type human a1m (SEQ ID NO: 1) as reference sequence, for example, in a BLAST search or using a nucleic acid molecule encoding Blc as probe in, for example, a hybridization experiment.

Preferred a1m scaffolds other than wide-type human a1m, in which one or more amino acid replacements, in particular at one or more position in one, two, three or all four loops, can be made in accordance with the teaching of the present disclosure, can, for example, be retrieved from the sequences shown in FIG. 5 (i.e. from a1m orthologues). Thus, an "a1m", when used herein, may be an orthologue of wide-type human a1m shown in SEQ ID NO: 1.

The present disclosure also provides a crystal structure of a1m. In a particular embodiment, the present disclosure includes the crystal structure depicted in FIG. 1. The present disclosure also includes an a1m crystal being characterized by the data shown in Table 1. Preferably, the a1m crystal has space group $P3_221$ and unit-cell parameters a=b=66.72, c=80.26, a=b=90.0, g=120.0.

TABLE 1

Data collection and refinement statistics

Data collection

| | |
|---|---|
| Space group | $P3_221$ |
| Unit-cell parameters (Å, °) | a = b = 66.72, c = 80.26, a = b = 90.0, g = 120.0 |
| Resolution (Å) | 46.89-2.17 |
| Total reflections | 114328 |
| Unique reflections | 11272 |
| Completeness (%) | 96.7 (80.0)[a] |
| <I/s(I)> | 20.2 (1.1)[a] |

TABLE 1-continued

Data collection and refinement statistics

| | |
|---|---|
| Redundancy | 10.4 (7.3)[a] |
| Mosaicity (°) | 0.306 |
| $R_{merge}$ (%) | 7.3 (169)[a] |
| Refinement[b] | |
| $R/R_{free}$ (%) | 21.3/26.0 |
| Protein residues | 164 |
| Ligand molecules | $Ni^{2+}$, glycerol |
| Solvent molecules | 47 |
| R.m.s. deviations from ideality: | |
| Bond lengths (Å) | 0.017 |
| Bond lengths (Å) | 0.017 |
| Bond angles (°) | 1.703 |
| Average B values (Å$^2$): | |
| Protein | 71.8 |
| Solvent | 74.7 |
| Ramachandran plot outliers[c]: | |
| Most favoured region | 130 |
| Additionally allowed region | 13 |
| Generously allowed region | 1 |
| Disallowed region | 2 |

[a]Values in parentheses are for the highest resolution shell (2.29-2.17 Å).
[b]For the last refinement cycle only data to 2.3 Å resolution were used.
[c]Values by PROCHECK (Laskowski et al. (1993), J. Appl. Cryst. 26, 283-291).

The term "mutagenesis" as used herein means that the amino acid naturally occurring at a sequence position of a1m can be substituted by at least one amino acid that is not present at this specific position in the respective natural polypeptide sequence. The term "mutagenesis" also includes modifying the length of sequence segments by deletion or insertion of one or more amino acids. Thus, it is within the scope of the disclosure that, for example, one amino acid at a chosen sequence position is replaced by a stretch of three random mutations, leading to an insertion of two amino acid residues compared to the length of (the respective segment) of the wild-type protein. Such an insertion of deletion may be introduced independently from each other in any of the peptide segments that can be subjected to mutagenesis in the disclosure. The term "random mutagenesis" means that no predetermined single amino acid (mutation) is present at a certain sequence position but that at least two amino acids can be incorporated into a selected sequence position during mutagenesis with a certain probability.

The term "collection" or "library" as used herein means that at least two muteins that differ from each other in their amino acid sequences are present. The upper limit of muteins generated by mutagenesis is usually restricted by the experimental conditions and is generally between $10^7$ and $10^{12}$.

Such experimental conditions can, for example, be achieved by incorporating codons with a degenerate base composition in the structural gene at those positions which are to be mutated. For example, use of the codon NNK or NNS (wherein N=adenine, guanine or cytosine or thymine; K=guanine or thymine; S=adenine or cytosine) allows incorporation of all 20 amino acids plus the amber stop codon during mutagenesis, whereas the codon VVS limits the number of possibly incorporated amino acids to 12 since it excludes the amino acids Cys, Ile, Leu, Met, Phe, Trp, Tyr, Val from being incorporated into the selected position of the polypeptide sequence; use of the codon NMS, for example, restricts the number of possible amino acids to 11 at a selected sequence position since it excludes the amino acids Arg, Cys, Gly, Ile, Leu, Met, Phe, Trp, Val from being incorporated at a selected sequence position. In a preferred embodiment of the method of the disclosure, a random mutagenesis is carried out, in which at least 4, preferably 6, more preferably 8 to 12 amino acids are allowed to be incorporated into a selected sequence position of a1m. In a particularly preferred embodiment, at least one sequence position is subjected to complete randomization, i.e. all 20 amino acids are allowed to be incorporated at this position during mutagenesis. From the above, it is also possible that the amino acid naturally present at a certain sequence position of a1m may also be present in the mutein after having subjecting this position to mutagenesis. It is also possible to use as described by Wang, L., et al., *Science,* 292:498-500, 2001 or Wang, L., Schultz, P. G., *Chem. Comm.,* 1:1-11, 2002 "artificial" codons such as UAG which are usually recognized as stop codons in order to insert other unusual amino acids, for example O-methyl-L-tyrosine or p-aminophenylalanine.

The term "$\alpha_1$-Microglobulin" ("$\alpha$1m" or "a1m") as used herein is not limited to the mature human $\alpha_1$-Microglobulin (20-203 of the human AMBP gene (Swiss-Prot ID: AMBP_HUMAN, UniProt ID: P02760; SEQ ID NO: 1), but includes all polypeptides having the structurally conserved lipocalin fold and a sequence homology or identity with respect to the amino acid sequence of the human a1m (e.g. 20-202 of the human AMBP gene, as comprised in the recombinant protein described in Example 1). This includes all proteins that have a sequence homology or identity of more than 60%, 70%, 80%, 85%, 90% or 95% in relation to the human a1m (20-202 of the human AMBP gene (Swiss-Prot ID: AMBP_HUMAN, UniProt ID: P02760); SEQ ID NO: 1). Preferably, such homologous sequences do not have a mutation or replacement in loops #1. #2, #3 and #4 as described herein.

The term "lipocalin fold" is used in its regular meaning as used, e.g., in Flower, D. R. (1996) or Skerra, A. (2000), supra, to describe the typical three-dimensional lipocalin structure with a conformationally conserved $\beta$-barrel as a central motif made of a cylindrically closed $\beta$-sheet of eight antiparallel strands, wherein the open end of the barrel the $\beta$-strands are connected by four loops in a pairwise manner so that the binding pocket is formed (see also FIG. 1). A representative lipocalin fold is the human a1m fold.

The definition of the "peptide loops" or "loops" as used in the present disclosure is in accordance with the regular meaning of the human a1m fold, as also illustrated in Example 1 and FIG. 1.

The term "homology" as used herein has its usual meaning and includes identical amino acids as well as amino acids which are regarded to be conservative substitutions (for example, exchange of a glutamate residue by a aspartate residue) at equivalent positions in the linear amino acid sequence of two proteins that are compared with each other, while the term "sequence identity" refers to the number of amino acids that are identical between two amino acid sequences at a particular amino acid position. Percent identity is determined by dividing the number of identical residues by the total number of residues and multiplying the product by 100. The term "reference sequence" and "wild type sequence" (of a1m) is used interchangeably herein.

The percentage of homology can be determined herein using the program BLASTP, version blastp 2.2.5 (Nov. 16, 2002; cf. Altschul, S. F. et al. (1997) *Nucleic Acids Res.* 25, 3389-3402). The percentage of homology is based on the alignment of the entire polypeptide sequences (cutoff value set to $10^{-3}$) including the propeptide sequences, using the human a1m as reference in a pairwise comparison. It is calculated as the percentage of numbers of "positives" (homologues amino acids) indicated as result in the BLASTP program output divided by the total number of amino acids selected by the program for the alignment. It is noted in this connection that this total number of selected amino acids can differ from the length of the a1m (184 amino acids including the propeptide) as it is seen in the following.

The skilled artisan has in his disposal published sequence alignments or alignments methods. A sequence alignment can, for example, be carried out as explained in WO 99/16873, using a published alignment such as the one in FIG. 1 of Redl, B. (2000) *Biochim. Biophys. Acta,* 1482, 241-248. If the three-dimensional structure of the lipocalins is available structural superpositions can also be used for the determination of those sequence positions that are to be subjected to mutagenesis in the present disclosure. Other methods of structural analysis such as multidimensional nuclear magnetic resonance spectroscopy can also be employed for this purpose.

The homologue of a1m can also be a mutein protein of a1m itself, in which amino acid substitutions are introduced at positions other than the positions selected in the present disclosure. For example, such a mutein can be a protein in which positions at the solvent exposed surface of the $\beta$-barrel are mutated compared to the wild type sequence of the tear lipocalin in order to increase the solubility or the stability of the protein.

No or no substantial binding affinity means, under the used conditions, no complex is formed between the target and the collection of muteins which are contacted with the target. It is clear to the person skilled in the art that complex formation is dependent on many factors such as concentration of the binding partners, concentration of compounds acting as competitors, ion strength of the buffers etc. The selection and enrichment is generally carried out under conditions which will allow isolation and enrichment of muteins having an affinity constant of at least $10^5$ $M^{-1}$ to the target. However, the washing and elution steps can be carried out under varying stringency. For example, if muteins having an affinity constant of at least $10^6$ $M^{-1}$ are to be isolated, washing and elution can be performed under increased stringency, i.e. more stringent conditions. A selection with respect to the kinetic characteristics is also possible. The selection can, for instance, be performed under conditions which favor complex formation of the target with muteins that show a slow dissociation from the target (receptor), or in other words a low $k_{off}$ rate.

In a preferred embodiment of the disclosure, a nucleic acid coding for the collection of muteins of the respective protein selected from a1m is used. In one embodiment, the nucleic acid results from mutagenesis and is operably fused with a gene coding for a polypeptide display moiety, such as the coat protein pIII of a filamentous bacteriophage of the M13-family or for a fragment thereof, in order to select at least one mutein for the binding of the given target. The fusion of a polypeptide display moiety may be at the 5' or 3' end of the lipocalin mutein and preferably is at the 3' end.

The nucleic acid that results from mutagenesis can be accomplished by, e.g., PCR techniques. In a preferred embodiment of the method of the disclosure, the generation of the nucleic acid coding for the mutated segments of the respective protein comprises the following two steps. First, two nucleic acid fragments, each of which codes for a part of the mutated protein are generated by PCR such that these fragments are partially overlapping. Second, these fragments are employed with two flanking primers in order to obtain the nucleic acid comprising the complete mutated structural gene. Due to the overlap, the full-length PCR product can be amplified in the course of this reaction, without that the addition of any additional nucleic acid is required. The two fragments, for example, can be obtained with a pair or pairs of suitable primers in two separate amplification reactions.

In another preferred embodiment of the disclosure, a nucleic acid molecules (e.g. DNA and RNA) comprising the nucleotide sequences coding one or more muteins as described herein are used. In this regard, it should be note that since the degeneracy of the genetic code permits substitutions of certain codons by other codons specifying the same amino acid, the disclosure is not limited to a specific nucleic acid molecule encoding a disclosed mutein or fusion protein but includes all nucleic acid molecules comprising nucleotide sequences encoding a functional mutein or fusion protein.

A nucleic acid molecule disclosed here may be "operably linked" to a regulatory sequence (or regulatory sequences) to allow expression of this nucleic acid molecule.

A nucleic acid molecule, such as DNA, is referred to as "capable of expressing a nucleic acid molecule" or capable "to allow expression of a nucleotide sequence" if it comprises sequence elements which contain information regarding to transcriptional and/or translational regulation, and such sequences are "operably linked" to the nucleotide sequence encoding the polypeptide. An operable linkage is a linkage in which the regulatory sequence elements and the sequence to be expressed are connected in a way that enables gene expression. The precise nature of the regulatory regions necessary for gene expression may vary among species, but in general these regions comprise a promoter which, in prokaryotes, contains both the promoter per se, i.e. DNA elements directing the initiation of transcription, as well as DNA elements which, when transcribed into RNA, will signal the initiation of translation. Such promoter regions normally include 5' non-coding sequences involved in initiation of transcription and translation, such as the −35/−10 boxes and the Shine-Dalgarno element in prokaryotes or the TATA box, CAAT sequences, and 5'-capping elements in eukaryotes. These regions can also include enhancer or repressor elements as well as translated signal and leader sequences for targeting the native polypeptide to a specific compartment of a host cell.

In addition, the 3' non-coding sequences may contain regulatory elements involved in transcriptional termination, polyadenylation or the like. If, however, these termination sequences are not satisfactory functional in a particular host cell, then they may be substituted with signals functional in that cell.

Therefore, a nucleic acid molecule of the disclosure can include a regulatory sequence, preferably a promoter sequence. In another preferred embodiment, a nucleic acid molecule of the disclosure comprises a promoter sequence and a transcriptional termination sequence. Suitable prokaryotic promoters are, for example, the tet promoter, the lacUV5 promoter or the T7 promoter. Examples of promoters useful for expression in eukaryotic cells are the SV40 promoter or the CMV promoter.

The nucleic acid molecules of the disclosure can also be comprised in a vector or any other cloning vehicles, such as plasmids, phagemids, phage, baculovirus, cosmids or artificial chromosomes. In a preferred embodiment, the nucleic acid molecule is comprised in a phasmid. A phasmid vector denotes a vector encoding the intergenic region of a temperent phage, such as M13 or f1, or a functional part thereof fused to the cDNA of interest. After superinfection of the bacterial host cells with such an phagemid vector and an appropriate helper phage (e.g. M13K07, VCS-M13 or R408) intact phage particles are produced, thereby enabling physical coupling of the encoded heterologous cDNA to its corresponding polypeptide displayed on the phage surface (reviewed, e.g., in Kay, B. K. et al. (1996) *Phage Display of Peptides and Proteins—A Laboratory Manual*, 1st Ed., Academic Press, New York N.Y.; Lowman, H. B. (1997) *Annu. Rev. Biophys. Biomol. Struct.* 26, 401-424 or Rodi, D. J. & Makowski, L. (1999) *Curr. Opin. Biotechnol.* 10, 87-93).

Such cloning vehicles can include, aside from the regulatory sequences described above and a nucleic acid sequence encoding a lipocalin mutein of the disclosure, replication and control sequences derived from a species compatible with the host cell that is used for expression as well as selection markers conferring a selectable phenotype on transformed or transfected cells. Large numbers of suitable cloning vectors are known in the art, and are commercially available.

The DNA molecule encoding lipocalin muteins of the disclosure, and in particular a cloning vector containing the coding sequence of such a lipocalin mutein can be transformed into a host cell capable of expressing the gene. Transformation can be performed using standard techniques (Sambrook, J. et al. (1989), supra). Thus, the disclosure is also directed to a host cell containing a nucleic acid molecule as disclosed herein.

The transformed host cells are cultured under conditions suitable for expression of the nucleotide sequence encoding a fusion protein of the disclosure. Suitable host cells can be prokaryotic, such as *Escherichia coli* (*E. coli*) or *Bacillus subtilis*, or eukaryotic, such as *Saccharomyces cerevisiae*, *Pichia pastoris*, SF9 or High5 insect cells, immortalized mammalian cell lines (e.g. HeLa cells or CHO cells) or primary mammalian cells.

The coding sequence for a1m, used as scaffold in the disclosure, can serve as a starting point for mutagenesis of the peptide segments selected by the person skilled in the art. The coding sequence of a1m has been described by Breustedt, D. A., Schönfeld, D. L., and Skerra, A. (2006) *Biochim Biophys Acta* 1764, 161-173. For the mutagenesis of the amino acids in the four peptide loops, the person skilled in the art has at his disposal the various known methods for site-directed mutagenesis or for mutagenesis by means of the polymerase chain reaction. The mutagenesis method can, for example, be characterized in that mixtures of synthetic oligodeoxynucleotides, which bear a degenerate base composition at the desired positions, can be used for introduction of the mutations. The use of nucleotide building blocks with reduced base pair specificity, as for example inosine, is also an option for the introduction of mutations into the chosen sequence segment or amino acid positions. The procedure for mutagenesis of target-binding sites is simplified as compared to antibodies, since for a1m only four instead of six sequence segments—corresponding to the four above mentioned peptide loops—have to be manipulated for this purpose. A further possibility is the so-called triplet-mutagenesis. This method uses mixtures of different nucleotide triplets each of which codes for one amino acid for the incorporation into the coding sequence.

One of the various applicable methods for the introduction of mutations in the region of the four selected peptide loops of a1m disclosed here is based on the use of four oligodeoxynucleotides, each of which is partially derived from one of the four corresponding sequence segments to be mutated. In the production of these oligodeoxynucleotides, the person skilled in the art can employ mixtures of nucleic acid building blocks for the synthesis of those nucleotide triplets which correspond to the amino acid positions to be mutated, so that codons or anticodons randomly arise for all amino acids or, according to the genetic code and to the composition of this mixture, for a selection of the desired amino acids at this position.

For example, the first oligodeoxynucleotide corresponds in its sequence—apart from the mutated positions—at least partially to the coding strand for the peptide loop, which is located in the polypeptide sequence of a1m at the most N-terminal position. Accordingly, the second oligodeoxynucleotide corresponds at least partially to the non-coding strand for the second sequence segment following in the polypeptide sequence. The third oligodeoxynucleotide corresponds in turn at least partially to the coding strand for the corresponding third sequence segment. Finally, the fourth oligodeoxynucleotide corresponds at least partially to the non-coding strand for the fourth sequence segment. A polymerase chain reaction can be performed with the respective first and second oligodeoxynucleotide and separately if needed, with the respective third and fourth oligodeoxynucleotide by using the nucleic acid which encodes the scaffold protein and/or its complementary strand as a template.

The amplification products of both of these reactions can be combined by various known methods into a nucleic acid which comprises the sequence from the first to the fourth sequence segments and which bears the mutations at the selected amino acid positions. To this end, said amplification products can, for example, be subjected to a new polymerase chain reaction using flanking oligodeoxynucleotides as primers as well as one or more mediator nucleic acid molecules which contribute the sequence between the second and the third sequence segment. In the choice of the number of the oligodeoxynucleotides used for the mutagenesis and their arrangement within the gene sequence of protein used, the person skilled in the art has furthermore numerous alternatives at his disposal.

The nucleic acid molecules which code for the sequence region encompassing the four peptide loops of a1m and which contain mutations at the selected positions mentioned above can, for example, be connected by ligation with the missing 5'- and 3'-sequences of a nucleic acid coding for a1m and/or the vector disclosed below, and can be cloned in a known host organism. A multitude of procedures are at the skilled person's disposal for the ligation and the cloning. For example, in the course of an amplification, synthetic nucleic acid molecules with restriction endonuclease recognition sequences, which are also present at the corresponding positions in the nucleic acid sequence for a1m, can be attached at both ends of the nucleic acid to be cloned so that a ligation is made possible following hydrolysis with the corresponding restriction enzyme. The missing 5'- and 3'-sequences of a nucleic acid coding for a1m can also be attached to the nucleic acid molecule comprising the mutated sequence positions via PCR.

Longer sequence segments within the gene coding for the protein selected for mutagenesis can also be subjected to random mutagenesis via known methods, for example, by use of the polymerase chain reaction under conditions of increased error rate, by chemical mutagenesis or by using bacterial mutator strains (Low et al., J. Mol. Biol. 260 (1996), 359-368). Such methods can also be used for the further optimization of the target affinity or target specificity of a mutein which has already been produced. Mutations which possibly occur outside the segments of the sequence positions 32-46, 66-72, 91-98, and 118-126 of a1m, for instance, can often be tolerated or can even prove advantageous, for example if they contribute to an improved folding efficiency or folding stability of the mutein.

After having brought the coding nucleic acid sequences that were subjected to mutagenesis to expression, the clones carrying the genetic information for the collection of respective muteins which bind a given target can be selected from the library obtained. Known expression strategies and selection strategies can be employed for the selection of these clones. Methods of this kind have been described in the context of the production or the engineering of recombinant antibody fragments, such as the "phage display" technique (Hoess, Curr. Opin. Struct. Biol. 3 (1993), 572-579; Wells and Lowman, Curr. Opin. Struct. Biol. 2 (1992), 597-604) or "colony screening" methods (Skerra et al., Anal. Biochem. 196 (1991), 151-155) or "ribosome display" (Roberts, Curr. Opin. Chem. Biol. 3 (1999) 268-273).

An embodiment of the "phage display" technique (Hoess, supra; Wells and Lowman, supra; Kay et al., Phage Display of Peptides and Proteins—A Laboratory Manual (1996), Academic Press) is given here as an example of a selection method according to the disclosure for muteins with the desired binding characteristics. For the exemplary selection method, phasmids are produced which effect the expression of the mutated a1m structural gene as a fusion protein with a signal sequence at the N-terminus, preferably the OmpA-signal sequence, and with the coat protein pIII of the phage M13 (Model and Russel, in "The Bacteriophages", Vol. 2 (1988), Plenum Press, New York, 375-456) or fragments of this coat protein, which are incorporated into the phage coat, at the C-terminus. The C-terminal fragment ΔpIII of the phage coat protein, which contains only amino acids 217 to 406 of the natural coat protein pIII, is preferably used to produce the fusion proteins. Especially preferred is a C-terminal fragment from pIII in which the cysteine residue at position 201 is missing or is replaced by another amino acid. The various other possible embodiments of the "phage display" technique are at disposal of person skilled in the art.

The fusion protein can contain other components, for example, an affinity tag or an epitope sequence for an antibody which allows the immobilization or the later purification of the fusion protein or its parts. Furthermore, a stop codon can be located between the region coding for a1m or its mutein and the gene segment for the coat protein or its fragment, which stop codon, preferably an amber stop codon, is at least partially translated into an amino acid during translation in a suitable suppressor strain.

Phasmids here denote plasmids which carry the intergenetic region of a filamentous bacterial phage, such as for example M13 or f1 (Beck and Zink, Gene 16 (1981), 35-58) or a functional part thereof, so that during superinfection of the bacterial cells with a helper phage, for example M13K07, VCS-M13 or R408, one strand of the circular phasmid DNA is packaged with coat proteins and is exported into the medium as so-called phagemid. On the one hand this phagemid has the a1m mutein encoded by the respective phasmid built into its surface as a fusion with the coat protein pIII or its fragment, wherein the signal sequence of the fusion protein is normally cleaved off. On the other hand it carries one or more copies of the native coat protein pIII from the helper phage and is thus capable of infecting a recipient generally a bacterial strain carrying an F- or F'-plasmid. In this way a physical coupling is ensured between the packaged nucleic acid carrying the genetic information for the respective a1m mutein, and the encoded protein which is at least partially presented in functional form on the surface of the phagemid.

A vector can, for example, be used in the construction of the phasmid with the sequences coding for the a1m muteins. The nucleic acid coding for the peptide loops can, for example, be inserted into the vector via both of the BstXI-restriction sites. Recombinant phasmids are incorporated by transformation into the *E. coli* strain, for example XL1-blue (Bullock et al., BioTechniques 5 (1987), 376-379) or TG1. In this way, clones are made which can produce many different a1m muteins as fusion proteins.

The disclosed library, i.e. the collection of the a1m muteins obtained by the taught methods, is subsequently superinfected in liquid culture according to known methods with an M13-helper phage. After this infection the incubation temperature of the culture can be reduced for production of the phagemids. Preferred incubation temperatures are those in which the optimal folding of the a1m mutein as a component of the fusion protein with the phage coat protein or its fragment is expected. During or after the infection phase the expression of the gene for the fusion protein with the a1m mutein can be induced in the bacterial cells, for example by addition of anhydrotetracycline. The induction conditions are so chosen that a substantial fraction of the phagemids produced presents at least one a1m mutein. The phagemids are isolated after a culture incubation phase of for example 6 to 8 hours. Various methods are known for isolation of the phagemids, such as for example precipitation with polyethylene glycol.

The isolated phasmids can be subjected to a selection by incubation with the desired target, wherein the target is present in a form allowing at least a temporary immobilization of those phagemids carrying muteins with the desired binding activity as fusion proteins in their coat. Among the various embodiments known to the person skilled in the art, the target can for example be conjugated with a carrier protein such as serum albumin and be bound via this carrier protein to a protein binding surface, for example polystyrene. Microtiter plates suitable for ELISA techniques or so-called "immuno-sticks" can preferably be used for this immobilization of the target. Alternatively, conjugates of the target can also be implemented with other binding groups such as for example biotin. The target can then be immobilized on surfaces which selectively bind this group, such as for example microtiter plates or paramagnetic particles coated with streptavidin or avidin.

Residual protein or phagemid-binding sites present on the surfaces which are charged with targets can be saturated with blocking solutions known for ELISA-methods. The phagemids are for example subsequently brought in contact in a physiological buffer with the target immobilized on the surface. Unbound phagemids are removed by multiple washings. The phagemid particles remaining on the surface are subsequently eluted. For elution, the free target can be added as a solution. But the phagemids can also be eluted by addition of proteases or, for example, in the presence of acids, bases, detergents or chaotropic salts, or under moderately denaturing conditions. A preferred method is the elution using buffers of pH 2.2, wherein the eluate is subsequently neutralized.

Afterwards, *E. coli* cells are infected with the eluted phagemids using generally known methods. The nucleic acids can also be extracted from the eluted phagemids and be incorporated into the cells in another manner. Starting from the *E. coli* clones obtained in this way, phagemids are in turn generated by superinfection with M13-helper phages according to the method described above and the phagemids propagated in this way are once again subjected to a selection on the surface with the immobilized target. Multiple selection cycles are often necessary in order to obtain the phagemids with the muteins of the disclosure in enriched form. The number of selection cycles is preferably chosen such that in the subsequent functional analysis at least 0.1% of the clones studied produce muteins with detectable affinity for the given target. Depending on the size, i.e. the complexity of the library employed, 2 to 8 cycles are typically required to this end.

For the functional analysis of the selected muteins, an *E. coli* strain can be infected with the phagemids obtained from the selection cycles and the corresponding double stranded phasmid DNA is isolated. Starting from this phasmid DNA or also from the single-stranded DNA extracted from the phagemids, the nucleic acid sequences of the selected muteins of the disclosure can be determined by the methods common for this purpose and the amino acid sequence can be derived therefrom. The mutated region or the sequence of the entire a1m mutein can be subcloned in another expression vector and expressed in a suitable host organism. The vector mentioned above can, for example, be used as the expression vector and the expression can be performed in *E. coli* strains, for example, *E. coli*-TG1. The muteins of a1m produced by genetic engineering can be purified by various proteinchemical methods. The a1m muteins so produced (for example with said vector) carry the affinity peptide Strep-Tag II (Schmidt et al., supra) at their C-terminus and, therefore, can preferably be purified by streptavidin affinity chromatography.

The selection can also be carried out by means of other methods, for example using "ribosome display" or "yeast (surface) display", among many other methods. Many corresponding embodiments are known to the person skilled in the art or are described in the literature. A combination of methods can also be applied. For example, clones selected or at least enriched by "phage display" can additionally be subjected to a "colony screening". This procedure has the advantage that individual clones can directly be isolated with respect to the production of an a1m mutein with detectable binding affinity for a non-natural target.

In addition to the use of *E. coli* as host organism in the "phage display" technique or the "colony screening" method, other bacterial strains, for example yeast or also insect cells or mammalian cells, can for example be used for this purpose. In addition to the selection of an a1m mutein from a primary library produced starting from a coding nucleic acid sequence for a mutein, comparable methods can also be applied in order to optimize a mutein with respect to the affinity or specificity for the desired target by repeated, optionally limited mutagenesis of its coding nucleic acid sequence.

It is additionally possible to subject the muteins produced as taught to a further, optionally partial random mutagenesis in order to select variants of even higher affinity from the new library thus obtained. A corresponding procedures have already been described for the case of digoxigenin binding muteins of the bilin-binding protein for the purpose of an "affinity maturation" (DE 199 26 068, WO 00/75308; Schlehuber et al., supra) and can also be applied to a mutein disclosed here in a corresponding manner by the person skilled in the art.

The present disclosure also relates to a lipocalin mutein derived from a polypeptide of a1m or a functional homologue thereof, wherein the mutein comprises at least one mutated amino acid residues at any sequence position in the four peptide loops #1, #2, #3 and #4 (dark gray areas of FIG.

6), wherein said a1m or functional homologue thereof has at least 60% sequence homology with human a1m, and wherein the mutein binds a given target with detectable affinity. This includes all proteins that have a sequence homology or identity of more than 60%, 70%, 80%, 85%, 90% or 95% in relation to the human a1m (20-203 of the human AMBP gene (Swiss-Prot ID: AMBP_HUMAN, UniProt ID: P02760; SEQ ID NO: 1).

The muteins of the disclosure can have the natural amino acid sequence of a1m outside the mutated segments, i.e. the regions of the amino acid positions 20 to 30, 48 to 63, 80 to 89, 100 to 115 and 129 to 165 of a1m. On the other hand, the muteins disclosed here can also contain amino acid mutations outside the positions subjected to mutagenesis compared to the wild-type a1m protein as long as those mutations do not interfere with the binding activity and the folding of the mutein. This includes that, for example, mutations, substitutions, deletions, insertion of amino acid residues as well as N- and/or C-terminal additions can be introduced into the natural amino acid sequence of a1m.

Such modifications of the amino acid sequence of the selected protein within or without the selected binding region include directed mutagenesis of single amino acid positions, for example, in order to simplify the subcloning of the mutated lipocalin gene or its parts by incorporating cleavage sites for certain restriction enzymes. For example, mutations can be introduced into the a1m gene in order to simplify the cloning of the mutated gene segment via two new BstXI restriction sites at these positions. Furthermore, mutations can be introduced within or without the four peptide loops in order to improve certain characteristics of the mutein of the protein chosen as scaffold, for example its folding stability or folding efficiency or its resistance to proteases.

In a preferred embodiment, for instance, Cys34 of a1m is exchanged to Ser or Ala, whereby its covalent crosslinking with other proteins such as immunoglobulin A (which might occur in in vivo applications of a mutein) can be prevented and its monomeric structure can be stabilized. Similarly, Cys residues which may occur as a result of the mutagenesis are not always crucial for the binding of the given target and may be substituted by Ala or other amino acids in order to prevent covalent bond formation or oxidation of the thiol group.

In a preferred embodiment, Cys34 can be substituted and/or the mutein carries one or more of the amino acid substitution compared to a1m. In this respect, it should be noted that the present disclosure is also directed to a (recombinant) a1m having the natural amino acid sequences in which only Cys34 has been substituted for any other suitable amino acid. This a1m polypeptide can be produced using the methods described here for the production of the other muteins of the disclosures, for example by use of the vector disclosed below.

The disclosure also provides a monomeric lipocalin mutein that, due to the potential to engineer two binding sites into the binding pocket of the mutein, can have binding specificity for two given ligands. For various applications it could also be advantageous to have more than one binding site per molecule available.

The one or more muteins of the disclosure may bind the desired target with a detectable affinity, i.e. with an affinity constant of preferably at least $10^5$ $M^{-1}$. Affinities lower than this are generally no longer measurable with common methods such as ELISA and are therefore of secondary importance for practical applications. Especially preferred are muteins which bind the desired target with an affinity of at least $10^6$ $M^{-1}$, corresponding to a dissociation constant for the complex of 1 µM. The binding affinity of a mutein to the desired target can be measured by the person skilled in the art by a multitude of methods, for example by fluorescence titration, by competition ELISA or by the technique of surface plasmon resonance.

The target which is bound by the mutein can be any chemical moiety that, for example, can also be recognized and bound by an antibody (immunoglobulin). Accordingly, the target can be a chemical compound in free or conjugated form which exhibits features of an immunological hapten, a hormone such as steroid hormones or any biopolymer or fragment thereof, for example, a peptide, a protein or protein domain, a peptide, an oligodeoxynucleotide, a nucleic acid, oligo- and polysaccharides or another macromolecule or conjugates thereof. In a preferred embodiment of the disclosure, the target is a protein. The protein can be provided either in free or conjugated form or as a fusion protein for the selection of muteins. In a further preferred embodiment of the disclosure, the target is a hapten.

A1m itself shows binding activity for some endogenous chemical compounds. For example, free heme (e.g. from hemolysis) is known to have severe destructive effects on proteins and DNA and can damage vital organs including the central nervous system (Kumar, S., and Bandyopadhyay, U. (2005) *Toxicol Lett* 157, 175-188). Recently, a1m has been shown to counteract the toxic effect of heme and also of other oxidants, notably hydrogen peroxide and hydroxyl radicals, and to exert reductase activity (Olsson, M. G., Olofsson, T., Tapper, H., and Åkerström, B. (2008) *Free Radic Res* 42, 725-736; Allhorn, M., Berggärd, T., Nordberg, J., Olsson, M. L., and Åkerström, B. (2002) *Blood* 99, 1894-1901; Allhorn, M., Klapyta, A., and Åkerström, B. (2005) *Free Radic Biol Med* 38, 557-567; Larsson, J., Allhorn, M., and Kerstrom, B. (2004) *Arch Biochem Biophys* 432, 196-204; Allhorn, M., Lundqvist, K., Schmidtchen, A., and Åkerström, B. (2003) *J Invest Dermatol* 121, 640-646). The identification of a potential heme binding site by the disclosure provides a structural explanation for these physiological activities of a1m. The putative association of the heme group with Cys34 and the close contacts with Lys92, Lys118 and Lys130 are in agreement with experimental observations that mutation or chemical blocking of these residues inhibits or at least decreases the reduces activity (Allhorn, M., Klapyta, A., and Åkerström, B. (2005) *Free Radic Biol Med* 38, 557-567). Furthermore, a1m can act as a scavenger of free heme itself and thereby help to remove it from sensitive tissues and to finally excrete it via the kidney.

It is clear to the skilled person that complex formation is dependent on many factors such as concentration of the binding partners, the presence of competitors, ionic strength of the buffer system etc. Selection and enrichment is generally performed under conditions allowing the isolation of lipocalin muteins having an affinity constant of at least $10^5$ $M^{-1}$ to the target. However, the washing and elution steps can be carried out under varying stringency. A selection with respect to the kinetic characteristics is possible as well. For example, the selection can be performed under conditions, which favor complex formation of the target with muteins that show a slow dissociation from the target, or in other words a low $k_{off}$ rate.

An a1m mutein of the disclosure may be used for complex formation with a non-natural target. The target may be any chemical compound in free or conjugated form which exhibits features of an immunological hapten, a hormone such as steroid hormones or any biopolymer or fragment thereof, for example, a protein or protein domain, a peptide, an oligodeoxynucleotide, a nucleic acid, an oligo- or polysaccharide or conjugates thereof. In a preferred embodiment of the disclosure the target is a protein. The protein can be any globular soluble protein or a receptor protein, for example, a trans-membrane protein involved in cell signaling, a component of the immune systems such as an MHC molecule or cell surface receptor that is indicative of a specific disease. The mutein may also be able to bind only fragments of a protein. For example, a mutein can bind to a domain of a cell surface receptor, when it is part of the receptor anchored in the cell membrane as well as to the same domain in solution, if this domain can be produced as a soluble protein as well. However the disclosure is by no means limited to muteins that only bind such macromolecular targets. But it is also possible to obtain muteins of tear lipocalin by means of mutagenesis which show specific binding affinity to ligands of low(er) molecular weight such as biotin, fluorescein or digoxigenin.

For some applications, it is useful to employ the muteins of the disclosure in a labeled form. Accordingly, the disclosure is also directed to lipocalin muteins which are conjugated to a label selected from the group consisting of enzyme labels, radioactive labels, colored labels, fluorescent labels, chromogenic labels, luminescent labels, haptens, digoxigenin, biotin, metal complexes, metals, and colloidal gold. The mutein may also be conjugated to an organic molecule. The term "organic molecule" as used herein preferably denotes an organic molecule comprising at least two carbon atoms, but preferably not more than seven rotatable carbon bonds, having a molecular weight in the range between 100 and 2000 Dalton, preferably 1000 Dalton, and optionally including one or two metal atoms.

In general, it is possible to label the lipocalin mutein with any appropriate chemical substance or enzyme, which directly or indirectly generates a detectable compound or signal in a chemical, physical or enzymatic reaction. An example for a physical reaction is the emission of fluorescence upon irradiation or the emission of X-rays when using a radioactive label. Alkaline phosphatase, horseradish peroxidase and β-galactosidase are examples of enzyme labels which catalyze the formation of chromogenic reaction products. In general, all labels commonly used for antibodies (except those exclusively used with the sugar moiety in the Fc part of immunoglobulins) can also be used for conjugation to the muteins of the present disclosure. Such conjugates can be produced by methods well known in the art.

Affinity tags such as the Strep-tag or Strep-tag II (Schmidt, T. G. M. et al. (1996) *J. Mol. Biol.* 255, 753-766), the myc-tag, the FLAG-tag, the His$_6$-tag (SEQ ID NO: 52) or the HA-tag or proteins such as glutathione-S-transferase also allow easy detection and/or purification of recombinant proteins are further examples of preferred fusion partners. Finally, proteins with chromogenic or fluorescent properties such as the green fluorescent protein (GFP) or the yellow fluorescent protein (YFP) are suitable fusion partners for a lipocalin mutein of the disclosure as well.

The present disclosure also relates to nucleic acid molecules (DNA and RNA) comprising nucleotide sequences coding for one or more muteins as described herein. Since the degeneracy of the genetic code permits substitutions of certain codons by other codons specifying the same amino acid, the disclosure is not limited to a specific nucleic acid molecule encoding a fusion protein of the disclosure but includes all nucleic acid molecules comprising nucleotide sequences encoding a functional fusion protein.

In addition, in one embodiment of the disclosure, the ligand that can be bound by a mutein derived from human a1m polypeptide or a functional homologue may be Colchicine, Lutetium (177Lu) DOTA-TATE ((177)Lu-DOTA) or fragments thereof. These ligands are derived from the plant *Colchicum autumnale* and a rare earth bound to the chelating ligand DOTA, respectively. But other targets may also be of mouse, rat, porcine, equine, canine, feline or bovine or cynomolgus origin, to name only a few illustrative examples. Targets may be so-called small molecule targets, peptides, proteins, cellular moieties, to name only a few illustrative examples.

Therefore, one aspect of the present disclosure is directed to a mutein derived from human a1m polypeptide or a functional homologue thereof that contains a mutation at any one of the sequence positions which correspond to the linear polypeptide sequence positions 32-46, 66-72, 91-98, and 118-126 of human a1m polypeptide, and binds to Colchicine. In some further embodiments, the a1m mutein contains a mutation at one or more of the sequence positions which correspond to the linear polypeptide sequence positions 34-37, 62-64, 97-99, 116-118, and 126-130 of human a1m polypeptide. In a still further embodiment, the a1m mutein further contains a mutation at one of the sequence positions which correspond to the linear polypeptide sequence positions 30, 47, 73, 75, 77, 79 and 90 of human a1m polypeptide. Examples of a1m lipocalin muteins that bind Colchicine are shown in SEQ ID NOs: 17, 18 and 19. The present application also encompasses lipocalin muteins that bind Colchicine and have a sequence homology or identity of 60% or more, such as 70%, 80%, 85% or 90%, in relation to the a1m lipocalin mutein shown in SEQ ID NO: 17, 18, or 19, respectively. In some preferred embodiments, such lipocalin muteins have at least one loop that is identical to a loop of as the a1m lipocalin mutein shown in SEQ ID NO: 17, 18, or 19, respectively.

Moreover, yet another aspect of the present disclosure is directed to a mutein derived from human a1m polypeptide or a functional homologue thereof that contains a mutation at any one of the sequence positions which correspond to the linear polypeptide sequence positions 32-46, 66-72, 91-98, and 118-126 of human a1m polypeptide, and binds to (177)Lu-DOTA. In some further embodiments, the a1m mutein contains a mutation at one or more of the sequence positions which correspond to the linear polypeptide sequence positions 34-37, 62-64, 97-99, 116-118, and 126-130 of human a1m polypeptide. In a still further embodiment, the a1m mutein further contains a mutation at one of the sequence positions which correspond to the linear polypeptide sequence positions 30, 47, 73, 75, 77, 79 and 90 of human a1m polypeptide. Examples of a1m lipocalin muteins that bind (177)Lu-DOTA are shown in SEQ ID NOs: 12, 13, 14, 15 and 16. The present application also encompasses lipocalin muteins that bind (177)Lu-DOTA and have a sequence homology or identity of 60% or more, such as 70%, 80%, 85% or 90%, in relation to any one of the a1m lipocalin muteins shown in SEQ ID NO: 12, 13, 14, 15 and 16. In some preferred embodiments, such lipocalin muteins have at least one loop that is identical to a loop of the a1m lipocalin mutein shown in SEQ ID NO: 12, 13, 14, 15, or 16, respectively.

Colchicine is an alkaloid derived from *Colchicum autumnale* possessing anti-inflammatory and antimitotic characteristics. Colchicine inhibits microtubule polymerization by binding to tubulin, one of the main constituents of microtubules. Availability of tubulin is essential to mitosis, and therefore colchicine effectively functions as a mitotic poison. The inhibiting function of colchicine has been of great use in the study of cellular genetics. Apart from inhibiting mitosis, colchicine also inhibits neutrophil motility and activity, leading to a net anti-inflammatory effect. Colchicine is used for the treatment and prevention of gout as well as liver and primary biliary cirrhosis (Chen Y-J. et al, (2008), Int. J. Phar. 350, 230-239). It has a narrow therapeutic index and the potential for severe or fatal toxicity. Acute colchicine poisoning can be caused intentionally, unintentionally because of non-optimal treatment or by mix up of *Colchicum autumnale* with the nontoxic eatable wood garlic. In any case acute colchicine poisoning is associated with a high mortality rate (Baud F. J., (1995), The New Engl. J. of Med., 642-643). An a1m mutein against colchicine could act as antidote to treat colchicine poisoning.

Lutetium (Lu) is an element of the lanthanide series and thus belongs to the rare earths, whereas DOTA is a chelating ligand binding transition metals and rare earths with high stability under physiological conditions (Corneillie, T. M. et al (2003), J. Am. Chem. Soc. 125, 3436-3437). The radioactive form 177-Lu in complex with DOTA to form 177-Lu-DOTA is a suitable tracer for radiotherapy of tumors and imaging as it emits both beta particles suitable for radiotherapy and gamma rays suitable for imaging (Garske, U. et al (2012), Theranostics. 2, 459-471). An a1m mutein binding to 117-Lu-DOTA combined with another mutein binding to e.g. a target expressed on tumors can be used to direct the radionucletide 177-Lu to the tumor for therapy as well as for imaging.

As used herein, the singular forms "a", "an", and "the", include plural references unless the context clearly indicates otherwise. Thus, for example, reference to "a lipocalin mutein" includes one or more lipocalin muteins.

Unless otherwise indicated, the term "at least" preceding a series of elements is to be understood to refer to every element in the series. Those skilled in the art will recognize, or be able to ascertain using no more than routine experimentation, many equivalents to the specific embodiments of the disclosure described herein. Such equivalents are intended to be encompassed by the present disclosure.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "having".

When used herein "consisting of" excludes any element, step, or ingredient not specified in the claim element. When used herein, "consisting essentially of" does not exclude materials or steps that do not materially affect the basic and novel characteristics of the claim.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or" as used herein.

Several references and documents are cited throughout the text of this specification. Each of the documents cited herein (including all patents, patent applications, scientific publications, SWISS-PROT Data Bank Accession Numbers, Swiss-Prot IDs, UniProt IDs, etc.), whether supra or infra, are hereby incorporated by reference in their entirety. Nothing herein is to be construed as an admission that the disclosure is not entitled to antedate such disclosure by virtue of prior disclosure.

The following non-limiting Examples and Figures further illustrate various aspects of the present disclosure.

EXAMPLES

Example 1

Structural Analysis of Human a1m

To provide insight into the suitability and properties of human a1m for generation of lipocalin muteins having binding affinity to a given target, the present disclosure teaches the three-dimensional structure of the unglycosylated human a1m. For crystal preparation and X-ray structural analysis the DNA sequence encoding amino acids 20-202 of the human AMBP gene (Swiss-Prot ID: AMBP_HUMAN, UniProt ID: P02760) was expressed with an N-terminal OmpA signal peptide and a C-terminal Strep-tag II from the plasmid pASK75-a1m2-strep as previously described (Breustedt, D. A., Schönfeld, D. L & Skerra, A. (2006) Comparative ligand-binding analysis of ten human lipocalins. Biochim. Biophys. Acta 1764, 161-173.), while Cys34 was replaced by Ser in order to prevent undesired disulfide bond formation.

The fold of a1m is characterized by a central eight-stranded calyx-like β-barrel, which is open to the solvent at one end, as well as a short α-helical stretch between strands A and B (loop #1, at the open end) and a C-terminal long α-helix following strand H which tightly packs against the β-strands G, H and A on the outside of the β-barrel (FIG. 1). Thus, a1m shows the typical structural features of a kernel lipocalin (Flower, D. R. (1996) *Biochem J* 318, 1-14; Skerra, A. (2000) *Biochim Biophys Acta* 1482, 337-350) wherein four structurally variable loops (designated as #1, #2, #3 and #4), which connect pairs of neighboring β-strands at the open end of the calyx, form the entrance to a large cavity.

Loop #1 and the β-strands B, C, and D, with crystallographic B-factors of 64-131 $Å^2$, appear considerably more flexible than the β-strands E, F, G, H, and A (B-factors: 38-65 $Å^2$) and also the loop #4. Regions of highest structural flexibility comprise the short α-helix within loop #1 as well as its connection to β-strand B (Pro35-Met44), loop #2 between β-strands C and D (Trp67-Cys72) and the loop connecting β-strands B and C (Glu53-Glu59) at the closed bottom of the β-barrel. As a consequence, side chains of residues in these regions were partly difficult to model.

Residues Cys72 and Cys169 form a disulfide bridge that links the structurally defined C-terminal residues of a1m to the transition region between loop #2 and β-strand D and represents a conserved structural feature within the lipocalin family (Skerra, A. (2000) *Biochim Biophys Acta* 1482, 337-350). Residues Cys34, Lys92, Lys118 and Lys130 were previously found to be involved in the association with chromophores (Berggård, T., Cohen, A., Persson, P., Lindqvist, A., Cedervall, T., Silow, M., Thogersen, I. B., Jonsson, J. A., Enghild, J. J., and Åkerström, B. (1999) *Protein Sci* 8, 2611-2620; Kwasek, A., Osmark, P., Allhorn, M., Lindqvist, A., Åkerström, B., and Wasylewski, Z. (2007)

Protein Expr Purif 53, 145-152). In this study, the single unpaired Cys34 had been mutated to Ser and was thus not available for chromophore binding. This residue is positioned in the transition region between strand A and loop #1 and is therefore freely accessible to the solvent, thus in principle allowing linkage to IgA or other binding partners in human plasma. The two N-glycosylation sites at Asn17 and Asn96 (Ekström, B., Lundblad, A., and Svensson, S. (1981) Eur J Biochem 114, 663-666; Escribano, J., Lopex-Otin, C., Hjerpe, A., Grubb, A., and Mendez, E. (1990) FEBS Lett 266, 167-170; Amoresano, A., Minchiotti, L., Cosulich, M. E., Campagnoli, M., Pucci, P., Andolfo, A., Gianazza, E., and Galliano, M. (2000) Eur J Biochem 267, 2105-2112) are also accessible to solvent and should sterically allow sugar attachment.

Lys118 and Lys92 are located at the upper rim of the central cavity while Lys130 is positioned half way down towards its bottom. Lys118 and Lys130 are within a 9 Å distance from Ser(Cys)34 and point into the binding site, thus enabling a ligand to interact with all three side chains. Their spatial relationship with Lys92, which is 13 Å away from Lys118, is less obvious. Notably, two other residues, Met62 and Met99, which both point into the cavity, could be involved in chromophore binding, as well. However, neither of them is absolutely conserved among orthologous a1m species (cf. FIG. 5). Nevertheless, except for a few crystallographic water molecules around the side chains of Lys92, Lys118, and Lys130, there was no indication for additional electron density close to any of these residues and, hence, the ligand pocket in the crystallized protein appears rather empty.

The central cavity of a1m is about 13 Å deep with an approximate diameter of around 13 Å at its top and 7 Å at its bottom (FIG. 1b). With these dimensions, the calyx is wider than in most other lipocalins. The electrostatic potential map exhibits a distinct positive pattern inside the pocket as well as in the region of the four loops at its opening while negative charge prevails at the outer surface of this lipocalin, in particular around the closed end of the ⊐-barrel (cf. FIG. 1b). Eight basic residues (Arg43, Arg66, Arg68, Lys69, Lys92, Lys94, Lys118, Lys130), notably without acidic counterpart, line the upper part of the pocket, whereas the lower cavity is shaped by hydrophobic side chains. There, several aromatic residues (Tyr79, Phe88, Phe114, Tyr132) are available for π-stacking and provide interactions for ligand binding. The pronounced positive potential inside the calyx together with the hydrophobic environment towards its bottom indicate a preference for negatively charged ligands with a hydrophobic moiety.

The corresponding structure-based multiple sequence alignment of a1m with the sequences of the three lipocalins (human complement component C8γ (Lovelace, L. L., Chiswell, B., Slade, D. J., Sodetz, J. M., and Lebioda, L. (2008) Mol Immunol 45, 750-756) (PDB ID: 2QOS, chain C), human L-prostaglandin D synthase (PGDS, unpublished; PDB ID: 3O2Y, chain B; for the closely related mouse ortholog, PDB ID: 2CZU, see Kumasaka, T., Aritake, K., Ago, H., Irikura, D., Tsurumura, T., Yamamoto, M., Miyano, M., Urade, Y., and Hayaishi, O. (2009) J Biol Chem 284, 22344-22352), and human lipocalin 15 (Lcn15, unpublished, PDB ID: 2XST) reveals that relative positions and lengths of the secondary structure elements largely coincide, whereas there are only minor sequence gaps between strands B/C, E/F and G/H, corresponding to the loop segments (FIG. 3a). Notably, as a typical feature of the lipocalins, despite high similarity in their fold the mutual sequence similarity is very low: of 184 residues in total, a1m shares only 40 (22%) identical residues with C8γ, 41 (22%) residues with PGDS, and merely 30 (16%) residues with Lcn15. Among those, 15 residues are common to all four lipocalin sequences (cf. FIG. 3a), including positions within the previously described structurally conserved regions (SCRs) and, in particular, the characteristic lipocalin signature Gly[23]-Xaa-Trp[25] (Flower, D. R. (1996) Biochem J 318, 1-14). Structural superposition of the four lipocalins indicates that the β-barrel core structure is highly conserved, whereas the loops #1, #2, #3 and #4 considerably vary in conformation (FIG. 3b).

A Cys residue equivalent to Cys34 of a1m is also present in the natural sequences of Lcn15 (UniProt ID: Q6UWW0) and C8γ (UniProt ID: P07360). Other human plasma lipocalins carry a similar free thiol group, which seems to generally provide for intermolecular cross-linking, at different positions. Lcn2/NGAL (UniProt ID: P80188), for example, carries such a Cys residue at position 87, which is equivalent to Asp83 in a1m. PGDS (UniProt ID: P41222), on the other hand, exhibits a catalytically active Cys residue inside the cavity at position 65, which would be equivalent to Ser47 in a1m.

In order to compare the sequence variation among closely related orthologous a1m species from several vertebrates, a BLAST search of residues 20-202 of the translated human AMBP gene against the UniProtKB sequence database was performed and 28 unique sequences with a score of higher than 350 were aligned (FIG. 5). In this alignment 36 residues of 183 in total are conserved to at least 95%. Six blocks of residues with elevated levels of conservation can be discerned: four blocks (Gln13-Phe16, Gly23-Trp25, Thr106-Tyr111 and Leu13-Arg134) are located around the calyx bottom, one block (Gly167-Pro171) harbors Cys169 involved in the lipocalin-typical disulfide bridge with the fully conserved residue Cys72, and one block (Thr33-Trp36) encompasses three residues of the putative heme binding site.

Notably, none of the residues that were previously postulated to be responsible for chromophore binding (Cys34, Lys92, Lys118, and Lys130) is conserved among the paralogous lipocalins mentioned above, while (except for Lys92) the same residues are highly conserved among orthologous a1m sequences. Also, the four-residue heme-binding sequence TCPW is highly conserved among the orthologs but diverse in other lipocalins (cf. FIG. 3a). His123, which is involved in the $Ni^{2+}$ binding site, is absolutely conserved only among a1m from mammals while the corresponding sequences from amphibia mostly exhibit Gly or Ser at this position. The first N-glycosylation site, Asn17, is not conserved whereas the second one at Asn96 is only conserved among mammals.

Example 2

A Nickel Binding Site at the Interface Between Two Crystallographic Neighbor Monomers At the tip of loop #4, the symmetry-related side chains His122 and His123' from two neighboring protein molecules in the crystal lattice coordinate a metal ion, together with four water molecules. The electron density of the metal has a pronounced peak height of 12.6 σ, and based on the presence of a high $NiCl_2$ concentration in the crystallization solution and on the apparent coordination geometry (Rulisek, L., and Vondrasek, J. (1998) Journal of inorganic biochemistry 71, 115-127) it was assigned as a $Ni^{2+}$ ion. Due to the local crystallographic C2 symmetry, there is a second equivalently bound $Ni^{2+}$ ion at a close distance of 7.8 Å, coordinated by His122' and His123 (FIG. 1c).

The ligand environment of the metal ion shows almost perfect octahedral geometry. The distances of His-N to the $Ni^{2+}$-ion are 1.9 Å and 2.3 Å, respectively, and the distances of waters are in the range of 2.2-2.3 Å, except for one water molecule (W4) that appears more tightly bound at 1.7 Å. The observed distances correspond well to the average distances of 2.18 Å for Ni—N and 2.28 Å for Ni—$OH_2$ that were deduced from medium resolution structures of proteins carrying $Ni^{2+}$-binding sites (Zheng, H., Chruszcz, M., Lasota, P., Lebioda, L., and Minor, W. (2008) *J Inorg Biochem* 102, 1765-1776) and also to the corresponding average values from the MESPEUS database (Ni—N: 2.19 Å) and (Ni—$OH_2$: 2.31 Å) (Hsin, K., Sheng, Y., Harding, M. M., Taylor, P., and Walkinshaw, M. D. (2008) *Journal of Applied Crystallography* 41, 963-968). Three further water molecules at a distance of 2.4-2.6 Å to the $Ni^{2+}$-coordinating waters, one of them shared between the two metal centers, are part of a second hydration shell. Lys118-NZ, Lys118-O, Ser120-OG, Arg121-N, and Thr126-OG1 are all in hydrogen bonding distances to at least one of these water molecules. The double $Ni^{2+}$-binding site explains the clearly supportive effect of $NiCl_2$ during crystallization of $\alpha_1m$.

The nickel binding site arises between two adjacent crystallographic monomers as part of an interface with a total contact surface of 690 Å$^2$. The complex significance score (CSS) of this interface as calculated by PISA is low with a value of 0.154. The protein dimer interface is further stabilized by π-stacking between Trp36 and Arg121' of the adjacent monomer as well as minor interactions between residues 66-69, 73-75, 90-99, and 118-123. As there is no biochemical evidence for a condition under which $\alpha_1m$ would preferentially form a dimer in solution, this interface is most likely a crystal packing artifact. The unglycosylated $\alpha_1m$ monomer is the predominant form at salt concentrations of 100-200 mM NaCl, and the presence of 1 mM $NiSO_4$ (or 1 mM EDTA) did not indicate metal-dependent protein dimerization during size exclusion chromatography.

Example 3

Human α1m Contains a Potential Binding Site that May Allow for the Interaction with a Ligand (Endogenous Target)

Human $\alpha_1m$ is known to bind retinoic acid and retinol, two endogenous physiological compounds, with dissociation constants around 1 μM (Breustedt, D. A., Schönfeld, D. L & Skerra, A. (2006) Comparative ligand-binding analysis of ten human lipocalins. Biochim. Biophys. Acta 1764, 161-173.). In addition, there are multiple indications from biochemical experiments for the ability of $\alpha_1m$ to bind and interact with heme (Allhorn, M., Berggärd, T., Nordberg, J., Olsson, M. L., and Åkerström, B. (2002) *Blood* 99, 1894-1901; Larsson, J., Allhorn, M., and Kerstrom, B. (2004) *Arch Biochem Biophys* 432, 196-204; Allhorn, M., Lundqvist, K., Schmidtchen, A., and Åkerström, B. (2003) *J Invest Dermatol* 121, 640-646), yet so far without a structural basis. Surprisingly for the first time, the present disclose teaches $\alpha_1m$ crystal structure for the presence of a typical heme binding site.

In a recent study, the CXXCH, FXXGXXCXG (SEQ ID NO: 53) and CP sequence signatures were identified as common heme binding motifs in proteins (Li, T., Bonkovsky, H. L., and Guo, J. T. (2011) *BMC Struct Biol* 11, 13). Indeed, the solvent accessible Cys34-Pro35 dipeptide that occurs in loop #1 appears as a possible site of interaction with heme. Proteins with known 3D structures in which CP dipeptides are involved in heme binding are the enzymes CYP121 from *M. tuberculosis* (Leys, D., Mowat, C. G., McLean, K. J., Richmond, A., Chapman, S. K., Walkinshaw, M. D., and Munro, A. W. (2003) *J Biol Chem* 278, 5141-5147) (PDB ID: 1N40) and prostacyclin 12 synthase (PGIS) from zebrafish (Li, Y. C., Chiang, C. W., Yeh, H. C., Hsu, P. Y., Whitby, F. G., Wang, L. H., and Chan, N. L. (2008) *J Biol Chem* 283, 2917-2926) (PDB ID: 3B98), both belonging to the cytochrome P450 family, as well as the human nuclear receptor REV-ERBbeta (Pardee, K. I., Xu, X., Reinking, J., Schuetz, A., Dong, A., Liu, S., Zhang, R., Tiefenbach, J., Lajoie, G., Plotnikov, A. N., Botchkarev, A., Krause, H. M., and Edwards, A. (2009) *PLoS Biol* 7, e43) (PDB ID: 3CQV), chloroperoxidase (CPO) from *C. fumago* (Kuhnel, K., Blankenfeldt, W., Terner, J., and Schlichting, I. (2006) *J Biol Chem* 281, 23990-23998) (PDB ID: 2CIW) and the microsomal prostaglandin E synthase (PGES) from *M. fascicularis* (Yamada, T., and Takusagawa, F. (2007) *Biochemistry* 46, 8414-8424) (PDB ID: 2PBJ).

Inspection of the region Thr33-Ser(Cys)34-Pro35-Trp36 in the crystal structure of $\alpha_1m$, which lies opposite to His123 in loop #4, reveals a striking similarity with the portion Thr109-Cys110-Pro111-Phe112 (SEQ ID NO: 54) of the heme binding site in PGES (FIG. 2). Indeed, superposition of the Cα-atoms of the TS(C)PW tetrapeptide in recombinant $\alpha_1m$ with the ones of the TCPF motif (SEQ ID NO: 54) in PGES results in an extraordinarily close match with an RMSD of 0.18 Å. Although the sequences of the corresponding motifs are less similar in the other enzymes mentioned above, superposition with the tetrapeptides Leu420-Cys421-Pro422-Gly423 (SEQ ID NO: 55) in PGIS (RMSD: 0.23 Å), Phe344-Cys345-Pro346-Gly347 (SEQ ID NO: 56) in CYP121 (RMSD: 0.12 Å), Val383-Cys384-Pro385-Met386 (SEQ ID NO: 57) in REV-ERBbeta (RMSD: 0.17 Å), and Pro28-Cys29-Pro30-Ala31 (SEQ ID NO: 58) in CPO (RMSD: 0.17 Å) indicates a conserved conformation.

In PGES, the axial $Fe^{3+}$ ligand position is occupied by the sulfhydryl group of the cosubstrate glutathione (GSH) while the Cys110-SH group from the enzyme's active site is positioned on the same side of the heme group at a distance of 5.3 Å to the metal center. In contrast to PGES, the corresponding Cys residues in the enzymes CYP121, PGIS, CPO and REV-ERBbeta act as axial ligands of the iron ion. If the heme group were bound to $\alpha_1m$ in a similar orientation with respect to the CP motif as it appears in PGES, His123 in loop #4 would be able to act as the opposite axial ligand to the central heme iron (FIG. 2a).

The close resemblance with PGES suggests that the putative heme binding site of $\alpha_1m$ may even allow for the interaction with an additional binding partner, for example GSH, next to the heme group. The cleft between loop #3 and loop #4 in $\alpha_1m$ seems sufficiently large and flexible to accommodate both a heme group and another ligand or substrate, which could dive further into the deeper part of the lipocalin pocket. The overall positive potential of the cavity should assist in the stabilization of the negatively charged heme group and both Lys118 and His122 would be able to form salt bridges with its propionate substituents. The almost absolutely conserved residues Trp36 and Trp95 among $\alpha_1m$ orthologs (cf. FIG. 5) are both accessible to solvent in the apo-protein and, indeed, can promote association with lipophilic ligands such as heme by involving aromatic interactions.

TCP[FW] motifs with similar geometry can be found in a number of other proteins not associated with heme. Most of these are either DNA binding proteins (PDB IDs: 2AIK, 1GPC, 3C25, 1KB6, 3BVQ, 2ATQ) or enzymes involved in redox processes utilizing GSH as (co)substrate (PDB IDs: 2HZF, 1KTE, 3GN3, 1ZH9, 2PBJ). In all cases where this motif has been structurally characterized it was shown that GSH can act as ligand. The superposition of the redox enzyme TCP[FW] motifs with the corresponding tetrapeptide in $\alpha_1$m results in RMSD values between 0.08 Å (2HZF) and 0.26 Å, while the TCP[FW] motifs of DNA binding proteins, with the exception of 2ATQ, align with higher RMSD values between 0.14 Å and 0.35 Å. The remarkably close conformational match of the TCP[FW] motif among those proteins suggests that it constitutes a general structural feature associated with GSH interaction. These findings imply that a1m might not only be able to bind heme but also to accept GSH as a co-substrate or ligand.

Example 4

Model of the $\alpha_1$m/Bikunin Precursor as an Example of a Natural Bifunctional Fusion Protein $\alpha_1$m shares a common biological source with the Kunitz-type serine proteinase inhibitor bikunin as both originate from the so-called $\alpha_1$m/bikunin precursor protein (AMBP). Bikunin (Pugia, M. J., Valdes, R., Jr., and Jortani, S. A. (2007) *Adv Clin Chem* 44, 223-245) is also known as urinary trypsin inhibitor or inter-α-trypsin inhibitor light chain, which further encompasses the mast cell protease inhibitor trypstatin (Itoh, H., Ide, H., Ishikawa, N., and Nawa, Y. (1994) *J Biol Chem* 269, 3818-3822). AMBP (UniProt ID: P02760) is expressed mainly in human hepatocytes from the AMBP gene with a 19 residue leader sequence and, probably after signal peptide processing, becomes posttranslationally cleaved by a furin-like protease into the two mature proteins, which are then separately glycosylated and finally excreted into the plasma (Åkerström, B., Lögdberg, L., Berggärd, T., Osmark, P., and Lindqvist, A. (2000) *Biochim Biophys Acta* 1482, 172-184; Tyagi, S., Salier, J. P., and Lal, S. K. (2002) *Arch Biochem Biophys* 399, 66-72). The $\alpha_1$m/bikunin precursor (AMBP) was modeled by combining the structure of $\alpha_1$m solved here with the previously published X-ray structure of bikunin (Xu, Y., Carr, P. D., Guss, J. M., and Ollis, D. L. (1998) *J Mol Biol* 276, 955-966) (FIG. 4), thus revealing a natural example of a truly bifunctional fusion protein.

Example 5

Primary Residues to be Considered for Randomization

As illustrated in FIG. 6, residues depicted in dark gray: 32-46, 66-72, 91-98, 118-126, and residues depicted in light gray: 30, 47, 64, 73, 75, 77, 79, 90, 99, 116, 128, are primary residues to be considered for randomization in order to subsequently select (a) mutein(s) derived from a1m or a functional homologue thereof that can bind a target other than an endogenous or natural target to which the wild-type a1m binds and wherein the mutein may have no or no substantial binding affinity for such endogenous or natural a1m target. Note that the reliable assignment of these residues became only possible after our structural elucidation of $\alpha_1$m.

Example 6

Preparation of Biotinylated Lu-DOTA-Bn p-$NH_2$-Bn-DOTA (44.5 μmol; Macrocyclics Inc., Dallas, Tex., USA), 18-Biotinamino-17-oxo-4,7,10,13-tetraoxa-16-azaicosan-1-oic acid succinimidyl ester (44.5 μmol; Iris Biotech GmbH, Marktredwitz, Germany), and triethylamine (26 μl, 2.8 mmol) were dissolved in 2 ml of dry N,N-dimethylformamide. The reaction mixture was stirred for 16 h at room temperature. The solvent was removed at vacuum. The remaining solid was dissolved in water/acetonitrile 1:1 and purified by reversed-phase HPLC (column: Merck Purospher Star RP-8e 250×10 mm; gradient 20-30% acetonitrile in water+0.1% (w/v) trifluoroacetic acid, tR=11.4 min). The DOTA-biotin conjugate was obtained as a colourless solid (isolated: 29.5 mg, 20.9 μmol, 47%, salt of trifluoroacetate) and subjected to ESI-MS analysis: calculated [M+H]+=1068.5282, [M+2H]2+=534.7677, [M−H]=1066.5136; found [M+H]+=1068.5388, [M+2H]2+=534.7754, [M−H]−=1066.5332

Example 7

Preparation of Biotinylated Colchicine

Deacetylation of colchicine was carried out in three steps following the publication of Bagnato et al. (Bagnato et al. (2004) *J. Org. Chem.* 69, 8987-8996). Colchicine (0.50 mmol), 4-(dimethylamino)pyridine (0.50 mmol), and triethylamine (141 μl, 1.0 mmol) were dissolved in 5 ml of dry acetonitrile. After addition of di-tert-butyl dicarbonate (1.25 mmol), the mixture was stirred under reflux. After 1 h additional di-tert-butyl dicarbonate (1.25 mmol) was added and refluxing was continued for another 2 h. After cooling to room temperature 25 ml of dichloromethane were added and the solution was washed three times with 25 ml of saturated aqueous citric acid. The combined aqueous solutions were extracted once with 25 ml of dichloromethane. The organic layers were combined and washed once with 25 ml of a saturated solution of sodium chloride, dried with sodium sulfate, and evaporated to dryness. The resulting brownish solid was used without further purification.

The crude N-Boc-colchicine from the previous step was dissolved in 5 ml of methanol and treated with 4 ml of a 0.5 M solution of sodium methoxide in methanol. The reaction was stirred for 90 min at room temperature, after which the reaction was quenched by the addition of 120 mg (2.24 mmol) of ammonium chloride. The solvent was removed under reduced pressure. The crude product was purified by silica chromatography, using ethyl acetate/acetone 4:1 as eluent. The desired product was obtained as a pale yellow solid (166 mg, 0.38 mmol, 75% over 2 steps). Analytical data were in agreement with published data.

N-Boc-N-deacetylcolchicine (0.34 mmol) was dissolved in 4 ml of dichloromethane. 400 μl of trifluoroacetic acid were added and the mixture was stirred for 3 h at room temperature. The solvent was removed under reduced pressure. After purification by silica chromatography (dichloromethane/methanol 9:1), the product was obtained as a yellow solid (142 mg, 0.30 mmol, 9%, salt of trifluoroacetate). Analytical data were in agreement with published data.

N-deacetylcolchicine (61 μmol of the trifluoroacetate), 18-Biotinamino-17-oxo-4,7,10,13-tetraoxa-16-azaicosan-1-oic acid succinimidyl ester (55 μmol) and triethylamine (14 μl, 100 μmol) were dissolved in 2 ml of dry dichloromethane. The reaction mixture was stirred for 24 h at room temperature. The solvent was removed under reduced pressure and the crude product was purified by silica chromatography (dichloromethane/methanol 9:1 to 7:1). The desired colchicine-biotin conjugate was obtained as a slightly yellowish solid (42 mg, 46 μmol, 84%) and subsequently applied to ESI-mass spectrometry: calculated $[M+H]^+=916.4373$, $[M-H]^-=914.4226$; measured $[M+H]^+=916.4358$, $[M-H]^-=914.4219$.

Example 8

Construction of a Mutant a1m Phage Display Library

Polymerase chain reaction (PCR) assembly of the a1m BstXI cassette as illustrated in FIG. 7 was essentially performed according to a published strategy (Gebauer, Skerra (2012) *Methods Enzymol* 503, 157-188) in a one pot amplification reaction with oligodeoxynucleotides (SEQ ID NO: 2-11). Oligodeoxynucleotides were designed such that the primers with SEQ ID NO: 2-5 corresponded to the coding strand and carried one of 19 different trimers at the amino acid positions 34, 36, 37, 47, 62, 64, 73, 75, 77, 90, 97, 99, 116, 118, 126, 128, and 130 respectively, while primers with SEQ ID NO: 5-8 corresponded to the non-coding strand. The two flanking primers with SEQ ID NO: 10 and SEQ ID NO: 11 were used in excess and served for the amplification of the assembled randomized gene fragment. In total, 15 PCR cycles using Taq DNA polymerase (Fermentas, St. Leon-Roth, Germany) were performed.

Oligodeoxynucleotides SEQ ID NO: 2-9 were synthesized using a Expedite Nucleic Acid Synthesize System (AME Bioscience, Bedfordshire, UK) and further purified by urea PAGE. Reaction tubes, solutions and nucleoside phosphoramidites were purchased from Sigma-Aldrich (SAFC Proligo Reagents, Steinheim, Germany), whereas trimer phosphoramidites were purchased from Glen Research (Sterling, Va., USA). The two flanking primers with SEQ ID NO: 10 and SEQ ID NO: 11 were purchased in HPLC grade from Thermo Fisher Scientific (Ulm, Germany). The resulting DNA library was cut with BstXI (New England Biolabs, Schwalbach, Germany) and cloned on the phagemid vector phNGAL108 (SEQ ID NO:20), which is based on the generic expression vector pASK75 (Skerra (1994) *Gene* 151, 131-135), codes for a fusion protein composed of the OmpA signal peptide, the synthetic a1m gene, the Strep-tag II followed by an amber codon, and the full length gene III coat protein of the filamentous bacteriophage M13 (Vogt and Skerra (2004) *Chem Bio Chem* 5, 191-199). After electroporation of *E. coli* XL1-Blue (Bullock et al. (1987) *Biotechniques* 5, 376-378) with the ligation mixture of 3 μg digested PCR product and 30 μg digested plasmid DNA, $7.9 \times 10^9$ transformants were obtained.

After electroporation cells which were transformed with the phasmid vectors on the basis of phNGAL108, coding for the library of the lipocalin muteins as phage pIII fusion proteins were plated onto LB-Amp plates (Ø 15 cm) and incubated overnight at 37° C. Then, cells were scratched off the plates, diluted in 2YT medium to an OD550 of 0.1 with the corresponding antibiotic added and cultured at 37° C. and 160 rpm until an OD550 of 0.6 was reached. After infection with VCS-M13 helper phage (Agilent Technologies, La Jolla, USA) at a multiplicity of infection of approximately 10 the culture was shaken for additional 30 min at 37° C., 100 rpm. Then, kanamycin (70 μg/ml) was added to the culture, while lowering the incubator temperature to 26° C. and increasing the shaker speed to 140 rpm. After 10 min gene expression was induced via addition of anhydrotetracycline (ACROS Organics, Geel, Belgium) at 25 μg/l (125 μl of a 200 μg/ml stock solution in dimethylformamide, DMF per liter of culture). Incubation continued for another 7 h at 26° C., 140 rpm.

Cells from the complete culture were sedimented by centrifugation (30 min, 12,100 g, 4° C.). The supernatant containing the phagemid particles was sterile-filtered (0.45 μm), mixed with ¼ volume 20% (w/v) PEG 8000, 15% (w/v) NaCl, and incubated on ice for at least 2 h. After centrifugation (60 min, 18,000 g, 4° C.), the supernatant was discarded and the sediment was recentrifugated (10 min, 18,000 g, 4° C.) to completely remove residual PEG solution. The precipitated phagemid particles from 1 liter of culture were dissolved in 40 ml of cold, sterile BBS/E (200 mM Na-borate, 160 mM NaCl, 1 mM EDTA pH 8.0) containing 50 mM benzamidine (Sigma). The solution was incubated on ice for 30 min. After centrifugation of undissolved components (10 min, 40,000 g, 4° C.) each supernatant was transferred to a new reaction vessel.

Addition of ¼ volume 20% w/v PEG 8000, 15% (w/v) NaCl and incubation for 60 min on ice served to reprecipitate the phagemid particles until the phagemids were aliquoted and frozen at −80° C. for storage. For the first selection cycle phagemids were thawed and centrifuged (20 min, 18,500 g, 4° C.), the supernatant was removed, and the precipitated phagemid particles were dissolved and combined in a total of 400 μl PBS containing 50 mM benzamidine. After incubation for 30 min. on ice, the solution was centrifuged (5 min, 18,500 g, 4° C.) in order to remove residual aggregates, and the supernatant was used directly for the phage display selection.

Example 9

Selection of a1m Muteins with Affinity to Lu-DOTA-Bn by Phage Display

For each panning cycle about $10^{13}$ recombinant phagemids in PBS (4 mM $KH_2PO_4$, 16 mM $Na_2HPO_4$, 115 mM NaCl, pH 7.4) were blocked with 2% (w/v) BSA in PBS/0.1T (PBS containing 0.1% (v/v) Tween 20 [polyoxyethylene sorbitan monolaurate; Sigma]) for 1 h in a total volume of 400 μl. 50 μl of a Streptavidin-coated magnetic particle suspension (Streptavidin Magnetic Particles; Roche Diagnostics, Mannheim, Germany) and NeutrAvidin-coated magnetic particles suspension (Sera-Mag Speed Beads NeutrAvidin microparticles; Thermo Scientific, Fremont, Calif., USA), respectively were separately washed twice with PBS/0.1T and blocked with 2% (w/v) BSA in PBS/0.1T for 1 h. Streptavidin-coated and NeutrAvidin-coated particles were applied alternately during the selection process to prevent enrichment of bead-specific phagemids.

The blocked Streptavidin/NeutrAvidin magnetic particles were then incubated with 100 nM biotinylated Lu-DOTA-Bn in PBS/0.1T supplemented with 2% BSA for 30 min under rotation, followed by blocking of free biotin-binding sites via the addition of 0.1 mM D-Desthiobiotin (IBA, Göttingen, Germany) for 30 min. After three washing steps with 500 μl PBS/0.1T the blocked, target-loaded particles were incubated with 400 μl of the blocked phagemids under rotation for initially 2 h in the first selection cycle. In the subsequent cycles, the incubation time was lowered to 1 h. Then, 0.1 mM D-Desthiobiotin was added to the mixture of phagemids and target for 20 min, before the magnetic particles were pulled down with a single tube magnetic stand for 2 min. The supernatant containing unbound phagemids was discarded. The target/phagemid complexes bound to magnetic particles were washed 10 times with 500 µl PBS/0.1T containing 0.1 mM D-Desthiobiotin, and then bound phagemids were eluted under conditions of competition by adding 400 ⊐l 100 µM non-biotinylated Lu-DOTA-Bn-NH$_2$ and rotation for 90 min. In total, four selection cycles were performed.

For amplification of eluted phagemids an exponentially growing culture of *E. coli* XL-1 Blue was infected for 30 min at 37° C. and 140 rpm. After centrifugation (5 min, 4000 rpm, 4° C.) the bacterial pellet was resuspended in 0.9 ml 2×YT medium (16 g/l Bacto Tryptone, 10 g/l Bacto Yeast Extract, 5 g/l NaCl, pH 7.5), plated onto LB-Amp plates (10 g/l Bacto Tryptone, 5 g/l Bacto Yeast Extract, 5 g/l NaCl, 15 g/l Bacto Agar, 100 mg/l ampicillin, pH 7.5), and incubated for 14-16 h at 32° C. Cells were then scraped off the plates and employed for rescue and re-amplification of the recombinant phagemids.

Screening of the enriched phagemid pools was performed by a screening ELISA (as illustrated in the description of FIG. 12) after the fourth panning cycle.

Example 10

Selection of a1m Muteins with Affinity to Colchicine by Phage Display

Phage display for the selection of a1m muteins specific for biotinylated Colchicine from Example 6 was performed as described in Example 6 for the Lu-DOTA-Bn target.

Example 11

Identification of a1m Muteins Specific for Lu-DOTA-Bn Via Screening ELISA

After four cycles of phagemid selection with Lu-DOTA-Bn as described in Example 9, the enriched pool of a1m muteins was sub-cloned on the expression plasmid pa1m2 (SEQ ID NO: 21), which encodes a fusion of the OmpA signal peptide for the periplasmic production in *E. coli* and the a1m coding region with the C-terminal Strep-tag II (Schmidt and Skerra (2007) *Nat. Protoc.* 2, 1528-1535) and used for transformation of the *E. coli* supE strain TG1/F$^-$ (a derivative of *E. coli* K12 TG1 (Kim et al. (2009) *J. Am. Chem. Soc.* 131, 3565-3576), and subjected to a screening ELISA.

For this purpose, single randomly picked colonies from the enriched pool and wild-type a1m-expressing cells as negative control were grown in 96-well plates (Multiple Well Plate 96 round bottom with lid; Sarstedt, Nuembrecht, Germany) in 100 µl TB-Amp medium (12 g/l Bacto Tryptone, 24 g/l Bacto Yeast Extract, 55 mM glycerol, 17 mM KH$_2$PO$_4$, 72 mM K$_2$HPO$_4$, 100 mg/l ampicillin) at 37° C., 300 rpm and 70% air humidity overnight (Minitron shaker, Infors AG, Bottmingen, Swiss). Next day, 5 µl of the overnight culture was used to inoculate a deep-well plate containing 700 µl TB-Amp medium. Initially, cells were grown at 37° C., 300 rpm and 70% air humidity for 2 h, followed by 1.5 h incubation at 22° C. and 300 rpm until exponential phase was reached. Periplasmic expression of a1m muteins was induced with 100 µl 0.2 µg/ml anhydrotetracycline (aTc; Acros, Geel, Belgium) dissolved in water-free dimethylformamide (DMF; Sigma-Aldrich, Steinheim, Germany) for 13-17 h at 20° C. and 300 rpm. Periplasmic protein extraction was performed with 200 µl BBS buffer (800 mM Na-borate, 640 mM NaCl, 8 mM EDTA, pH 8.0) including 1 mg/ml lysozyme (AppliChem, Darmstadt, Germany) by incubation for 1 h at 4° C. and agitation at 900 rpm (Microplate Shaker, VWR International GmbH, Darmstadt, Germany). After blocking with 200 µl 10% (w/v) BSA in PBS/0.5T for 1 h at 4° C. and 900 rpm the plates were centrifuged for 30 min at 4° C. and 5000 g. The supernatant was used for ELISA.

For capturing of biotinylated target, a 96-well MaxiSorp polystyrene microtiter plate (C96, Nunc, Langenselbold, Germany) was coated with 5 µg/ml Streptavidin in PBS over night at 4° C. and blocked with 3% (w/v) BSA in TBS/0.1T (20 mM Tris, 2.5 mM KCl, 137 mM NaCl, pH 7.4 containing 0.1% Tween) at room temperature for 1 h. After 5 washing steps with TBS/0.1T, 0.5 µM biotinylated Lu-DOTA-Bn from Example 6 was applied for 1 h, followed by the addition 20 µl D-Desthiobiotin in a concentration of 5 µM to prevent binding of a1m muteins to streptavidin via their Strep-tag II. After the wells were washed, the cell extract from above was incubated for 1.5 h at room temperature. Bound a1m muteins were detected via the Strep-tag II using a 1:1000 dilution of Strep-MAB-Classic (IBA, Göttingen, Germany) in TBS/0.1T for 1 h. This primary, mouse-derived antibody was then detected using an anti-mouse IgG (Fc-specific)/AP conjugate (Sigma) in a dilution of 1:2000 in TBS/0.1T as secondary antibody for 1 h. Final washing steps using TBS/0.1T and TBS were followed by signal development in the presence of 100 µl 0.5 mg/ml p-nitrophenyl phosphate (AppliChem, Darmstadt, Germany) in 100 mM Tris/HCl, pH 8.8, 100 mM NaCl, 5 mM MgCl$_2$ for up to 1.5 h. Absorption at 405 nm was measured in a SpectraMax 250 reader (Molecular Devices, Sunnyvale, USA).

Example 12

Identification of a1m Muteins Specific for Colchicine Via Screening ELISA a1m mutein with affinity to Colchicine were identified via screening ELISA as described in Example 11.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention. The invention has been described broadly and generically herein. All patents, patent applications, text books and peer-reviewed publications described herein are hereby incorporated by reference in their entirety. Furthermore, where a definition or use of a term in a reference, which is incorporated by reference herein is inconsistent or contrary to the definition of that term provided herein, the definition of that term provided herein applies and the definition of that term in the reference does not apply. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group. Further embodiments of the invention will become apparent from the following claims.

The invention claimed is:

1. A mutein of mature human alpha-1 microglobulin (a1m) (SEQ ID NO: 1) comprising four peptide loops comprising sequence positions 29-48, 63-80, 89-100, and 115-129, respectively, of the linear polypeptide sequence of mature human a1m (SEQ ID NO: 1), wherein at least one amino acid of each of at least two of said four peptide loops has been mutated, wherein said mutein has at least 80% sequence identity to the linear polypeptide sequence of mature human a1m (SEQ ID NO: 1), wherein said mutein binds a target other than retinoic acid or retinol, and wherein said mutein has no detectable binding affinity for retinoic acid or retinol.

2. The mutein of claim 1, wherein at least one amino acid of each of at least three of said four peptide loops has been mutated.

3. The mutein of claim 1, wherein at least one amino acid of each of said four peptide loops has been mutated.

4. The mutein of claim 1, wherein at least one amino acid of each of at least three of the peptide loops corresponding to sequence positions 63-80, 89-100, and 115-129 of the linear polypeptide sequence of mature human a1m (SEQ ID NO: 1) has been mutated.

5. The mutein of claim 1, wherein said mutein comprises at least one mutated amino acid at sequence positions 30, 47, 64, 73, 75, 77, 79, 90, 99, 116, and 128 of the linear polypeptide sequence of mature human a1m (SEQ ID NO: 1).

6. The mutein of claim 1, wherein said mutein comprises at least one mutated amino acid in each of the four loop regions comprising sequence positions 32-46, 66-72, 91-98, and 118-126 of the linear polypeptide sequence of mature human a1m (SEQ ID NO: 1), respectively.

7. The mutein of claim 1, wherein said mutein has no detectable binding affinity for retinoic acid or retinol, wherein the binding affinity is defined by a dissociation constant and is detected using ELISA or using the technique of surface plasmon resonance.

8. The mutein of claim 1, wherein said mutein binds a target other than retinoic acid or retinol, wherein the binding affinity is defined by a dissociation constant and is detected using ELISA or using the technique of surface plasmon resonance.

9. The mutein of claim 1, wherein detectable binding affinity for retinoic acid or retinol is defined by a dissociation constant of at most 100 μM.

10. The mutein of claim 1, wherein the target is Lutetium ($^{177}$Lu) DOTA-TATE or Colchicine.

11. The mutein of claim 10, wherein the mutein has at least 90% sequence identity to an amino acid sequence selected from the group consisting of SEQ ID NOs: 12-19 or a fragment or variant thereof.

12. The mutein of claim 1, wherein the target is a tumor-specific cellular surface molecule.

13. The mutein of claim 1, wherein the mutein is coupled to a compound selected from the group consisting of a protein, an antibody, an enzyme, a radioactive moiety, and a molecule with a defined binding characteristic.

14. The mutein of claim 1, wherein the mutein is conjugated to a label selected from the group consisting of: organic molecules, enzyme labels, radioactive labels, colored labels, fluorescent labels, chromogenic labels, luminescent labels, haptens, digoxigenin, biotin, metal complexes, metals, and colloidal gold.

15. The mutein of claim 1, wherein the mutein is fused at its N-terminus and/or its C-terminus to a fusion partner.

16. The mutein of claim 15, wherein the fusion partner extends the serum half-life of the mutein.

17. The mutein of claim 16, wherein the fusion partner that extends the serum half-life is selected from the group consisting of a polyalkylene glycol molecule, a polyethylene glycol molecule, hydroxyethyl starch, a Fc part of an immunoglobulin, a CH3 domain of an immunoglobulin, a CH4 domain of an immunoglobulin, an albumin binding peptide, and an albumin binding protein.

18. A pharmaceutical composition comprising a mutein as defined in claim 1.

19. A diagnostic or analytical kit comprising a mutein as defined in claim 1.

20. A mutein of claim 1, wherein said mutein has at least 85% sequence identity to the linear polypeptide sequence of mature human a1m (SEQ ID NO: 1).

\* \* \* \* \*

SEQUENCE LISTING

```
<160> NUMBER OF SEQ ID NOS: 66

<210> SEQ ID NO 1
<211> LENGTH: 183
<212> TYPE: PRT
<213> ORGANISM: Homo sapiens
<220> FEATURE:
<221> NAME/KEY: MISC_FEATURE
<222> LOCATION: (1)..(183)
<223> OTHER INFORMATION: wild-type human a1m sequence

<400> SEQUENCE: 1

Gly Pro Val Pro Thr Pro Pro Asp Asn Ile Gln Val Gln Glu Asn Phe
1               5                   10                  15

Asn Ile Ser Arg Ile Tyr Gly Lys Trp Tyr Asn Leu Ala Ile Gly Ser
            20                  25                  30

Thr Ser Pro Trp Leu Lys Lys Ile Met Asp Arg Met Thr Val Ser Thr
        35                  40                  45

Leu Val Leu Gly Glu Gly Ala Thr Glu Ala Glu Ile Ser Met Thr Ser
    50                  55                  60

Thr Arg Trp Arg Lys Gly Val Cys Glu Glu Thr Ser Gly Ala Tyr Glu
65                  70                  75                  80

Lys Thr Asp Thr Asp Gly Lys Phe Leu Tyr His Lys Ser Lys Trp Asn
                85                  90                  95

Ile Thr Met Glu Ser Tyr Val Val His Thr Asn Tyr Asp Glu Tyr Ala
            100                 105                 110

Ile Phe Leu Thr Lys Lys Phe Ser Arg His His Gly Pro Thr Ile Thr
        115                 120                 125

Ala Lys Leu Tyr Gly Arg Ala Pro Gln Leu Arg Glu Thr Leu Leu Gln
    130                 135                 140

Asp Phe Arg Val Val Ala Gln Gly Val Gly Ile Pro Glu Asp Ser Ile
145                 150                 155                 160

Phe Thr Met Ala Asp Arg Gly Glu Cys Val Pro Gly Glu Gln Glu Pro
                165                 170                 175

Glu Pro Ile Leu Ile Pro Arg
            180

<210> SEQ ID NO 2
<211> LENGTH: 78
<212> TYPE: DNA
<213> ORGANISM: Artificial Sequence
<220> FEATURE:
<223> OTHER INFORMATION: Description of Artificial Sequence: Synthetic
      primer for construction of a1m library
<220> FEATURE:
<221> NAME/KEY: modified_base
<222> LOCATION: (19)..(21)
<223> OTHER INFORMATION: a, c, t or g
<220> FEATURE:
<221> NAME/KEY: modified_base
<222> LOCATION: (25)..(30)
<223> OTHER INFORMATION: a, c, t or g
<220> FEATURE:
<221> NAME/KEY: modified_base
<222> LOCATION: (58)..(60)
<223> OTHER INFORMATION: a, c, t or g
```

<400> SEQUENCE: 2
ctggcaattg gtagcaccnn nccgnnnnnn aagaaaatca tggatcgtat gaccgttnnn    60
accctggttc tgggtgaa                                                  78

<210> SEQ ID NO 3
<211> LENGTH: 84
<212> TYPE: DNA
<213> ORGANISM: Artificial Sequence
<220> FEATURE:
<223> OTHER INFORMATION: Description of Artificial Sequence: Synthetic
      primer for construction of a1m library
<220> FEATURE:
<221> NAME/KEY: modified_base
<222> LOCATION: (19)..(21)
<223> OTHER INFORMATION: a, c, t or g
<220> FEATURE:
<221> NAME/KEY: modified_base
<222> LOCATION: (25)..(27)
<223> OTHER INFORMATION: a, c, t or g
<220> FEATURE:
<221> NAME/KEY: modified_base
<222> LOCATION: (52)..(54)
<223> OTHER INFORMATION: a, c, t or g
<220> FEATURE:
<221> NAME/KEY: modified_base
<222> LOCATION: (58)..(60)
<223> OTHER INFORMATION: a, c, t or g
<220> FEATURE:
<221> NAME/KEY: modified_base
<222> LOCATION: (64)..(66)
<223> OTHER INFORMATION: a, c, t or g

<400> SEQUENCE: 3
accgaagcag aaatcagcnn naccnnnacc cgttggcgta aaggtgtttg tnnngaannn    60
agcnnngcct acgaaagacc gata                                           84

<210> SEQ ID NO 4
<211> LENGTH: 116
<212> TYPE: DNA
<213> ORGANISM: Artificial Sequence
<220> FEATURE:
<223> OTHER INFORMATION: Description of Artificial Sequence: Synthetic
      primer for construction of a1m library
<220> FEATURE:
<221> NAME/KEY: modified_base
<222> LOCATION: (19)..(21)
<223> OTHER INFORMATION: a, c, t or g
<220> FEATURE:
<221> NAME/KEY: modified_base
<222> LOCATION: (40)..(42)
<223> OTHER INFORMATION: a, c, t or g
<220> FEATURE:
<221> NAME/KEY: modified_base
<222> LOCATION: (46)..(48)
<223> OTHER INFORMATION: a, c, t or g
<220> FEATURE:
<221> NAME/KEY: modified_base
<222> LOCATION: (84)..(86)
<223> OTHER INFORMATION: a, c, t or g
<220> FEATURE:
<221> NAME/KEY: modified_base
<222> LOCATION: (90)..(92)
<223> OTHER INFORMATION: a, c, t or g
<220> FEATURE:
<221> NAME/KEY: modified_base
<222> LOCATION: (96)..(98)
<223> OTHER INFORMATION: a, c, t or g

<400> SEQUENCE: 4
accgacggta aattcctgnn ncataaaagc aaacataacn nnaccnnnga aagctatgtc    60
gtgcacaccg tcagcatggt ccgnnnattn nngcannnct gtatggtcgt gcacct 116

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Synthetic
      primer for construction of a1m library
<220> FEATURE:
<221> NAME/KEY: modified_base
<222> LOCATION: (19)..(21)
<223> OTHER INFORMATION: a, c, t or g
<220> FEATURE:
<221> NAME/KEY: modified_base
<222> LOCATION: (25)..(27)
<223> OTHER INFORMATION: a, c, t or g

<400> SEQUENCE: 5
gagtacgcca tcttcctgnn naaannnttc agc 33

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence: Synthetic
      primer for construction of a1m library

<400> SEQUENCE: 6
gctgatttct gcttcggtag caccttcacc cagaaccagg gt 42

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence: Synthetic
      primer for construction of a1m library

<400> SEQUENCE: 7
caggaattta ccgtcggtat cggtcttttc gtaggc 36

<210> SEQ ID NO 8
<211> LENGTH: 46
<212> TYPE: DNA
<213> ORGANISM: Artificial Sequence
<220> FEATURE:
<223> OTHER INFORMATION: Description of Artificial Sequence: Synthetic
      primer for construction of a1m library

<400> SEQUENCE: 8
caggaagatg gcgtactcat catagttggt gtgcacgaca tagctt 46

<210> SEQ ID NO 9
<211> LENGTH: 45
<212> TYPE: DNA
<213> ORGANISM: Artificial Sequence
<220> FEATURE:
<223> OTHER INFORMATION: Description of Artificial Sequence: Synthetic
      primer for construction of a1m library

<400> SEQUENCE: 9
atcctgcagc agggtttcac gcagctgagg tgcacgacca tacag 45

<210> SEQ ID NO 10
<211> LENGTH: 49
<212> TYPE: DNA

<210> SEQ ID NO 10
<211> LENGTH: 49
<212> TYPE: DNA
<213> ORGANISM: Artificial Sequence
<220> FEATURE:
<223> OTHER INFORMATION: Description of Artificial Sequence: Synthetic
      primer for construction of a1m library

<400> SEQUENCE: 10
tatctcccag atctatggga aatggtataa tctggcaatt ggtagcacc          49

<210> SEQ ID NO 11
<211> LENGTH: 50
<212> TYPE: DNA
<213> ORGANISM: Artificial Sequence
<220> FEATURE:
<223> OTHER INFORMATION: Description of Artificial Sequence: Synthetic
      primer for construction of a1m library

<400> SEQUENCE: 11
gggatgccaa caccctgggc aacaacacga aaatcctgca gcagggtttc          50

<210> SEQ ID NO 12
<211> LENGTH: 183
<212> TYPE: PRT
<213> ORGANISM: Artificial Sequence
<220> FEATURE:
<223> OTHER INFORMATION: Description of Artificial Sequence: Synthetic
      a1m mutein D1A10 polypeptide

<400> SEQUENCE: 12

Gly Pro Val Pro Thr Pro Pro Asp Asn Ile Gln Val Gln Glu Asn Phe
1               5                   10                  15

Asn Ile Ser Gln Ile Tyr Gly Lys Trp Tyr Asn Leu Ala Ile Gly Ser
            20                  25                  30

Thr Lys Pro Val Lys Lys Lys Ile Met Asp Arg Met Thr Val Ala Thr
        35                  40                  45

Leu Val Leu Gly Glu Gly Ala Thr Glu Ala Glu Ile Ser Met Thr Tyr
    50                  55                  60

Thr Arg Trp Arg Lys Gly Val Cys Lys Glu Phe Ser Glu Ala Tyr Glu
65                  70                  75                  80

Lys Thr Asp Thr Asp Gly Lys Phe Leu Gly His Lys Ser Lys His Asn
                85                  90                  95

Val Thr Trp Glu Ser Tyr Val Val His Thr Asn Tyr Asp Glu Tyr Ala
            100                 105                 110

Ile Phe Leu Tyr Lys His Phe Ser Arg Gln His Gly Pro Ile Ile Met
        115                 120                 125

Ala Ala Leu Tyr Gly Arg Ala Pro Gln Leu Arg Glu Thr Leu Leu Gln
    130                 135                 140

Asp Phe Arg Val Val Ala Gln Gly Val Gly Ile Pro Glu Asp Ser Ile
145                 150                 155                 160

Phe Thr Met Ala Asp Arg Gly Glu Cys Val Pro Gly Glu Gln Glu Pro
                165                 170                 175

Glu Pro Ile Leu Ile Pro Arg
            180

<210> SEQ ID NO 13
<211> LENGTH: 183
<212> TYPE: PRT
<213> ORGANISM: Artificial Sequence
<220> FEATURE:
<223> OTHER INFORMATION: Description of Artificial Sequence: Synthetic
      a1m mutein D1A11 polypeptide

<400> SEQUENCE: 13

```
Gly Pro Val Pro Thr Pro Pro Asp Asn Ile Gln Val Gln Glu Asn Phe
1               5                   10                  15

Asn Ile Ser Gln Ile Tyr Gly Lys Trp Tyr Asn Leu Ala Ile Gly Ser
            20                  25                  30

Thr Ile Pro Glu Arg Lys Lys Ile Met Asp Arg Met Thr Val Gln Thr
        35                  40                  45

Leu Val Leu Gly Glu Gly Ala Thr Glu Ala Glu Ile Ser Ala Thr Ala
    50                  55                  60

Thr Arg Trp Arg Lys Gly Val Cys Glu Glu Pro Ser Asp Ala Tyr Glu
65                  70                  75                  80

Lys Thr Asp Thr Asp Gly Lys Phe Leu Tyr His Lys Ser Lys His Asn
                85                  90                  95

Tyr Thr His Glu Ser Tyr Val Val His Thr Asn Tyr Asp Glu Tyr Ala
            100                 105                 110

Ile Phe Leu Lys Lys Lys Phe Ser Arg Gln His Gly Pro Trp Ile Asn
        115                 120                 125

Ala Trp Leu Tyr Gly Arg Ala Pro Gln Leu Arg Glu Thr Leu Leu Gln
    130                 135                 140

Asp Phe Arg Val Val Ala Gln Gly Val Gly Ile Pro Glu Asp Ser Ile
145                 150                 155                 160

Phe Thr Met Ala Asp Arg Gly Glu Cys Val Pro Gly Glu Gln Glu Pro
                165                 170                 175

Glu Pro Ile Leu Ile Pro Arg
            180

<210> SEQ ID NO 14
<211> LENGTH: 183
<212> TYPE: PRT
<213> ORGANISM: Artificial Sequence
<220> FEATURE:
<223> OTHER INFORMATION: Description of Artificial Sequence: Synthetic
      a1m mutein D1B1 polypeptide

<400> SEQUENCE: 14

Gly Pro Val Pro Thr Pro Pro Asp Asn Ile Gln Val Gln Glu Asn Phe
1               5                   10                  15

Asn Ile Ser Gln Ile Tyr Gly Lys Trp Tyr Asn Leu Ala Ile Gly Ser
            20                  25                  30

Thr Gln Pro Arg Leu Lys Lys Ile Met Asp Arg Met Thr Val His Thr
        35                  40                  45

Leu Val Leu Gly Glu Gly Ala Thr Glu Ala Glu Ile Ser Gly Thr Pro
    50                  55                  60

Thr Arg Trp Arg Lys Gly Val Cys Lys Glu Phe Ser Lys Ala Tyr Glu
65                  70                  75                  80

Lys Thr Asp Thr Asp Gly Lys Phe Leu Lys His Lys Ser Lys His Asn
                85                  90                  95

His Thr Lys Glu Ser Tyr Val Val His Thr Asn Tyr Asp Glu Tyr Ala
            100                 105                 110

Ile Phe Leu Arg Lys Ile Phe Ser Arg Gln His Gly Pro Ser Ile Ile
        115                 120                 125

Ala Tyr Leu Tyr Gly Arg Ala Pro Gln Leu Arg Glu Thr Leu Leu Gln
    130                 135                 140

Asp Phe Arg Val Val Ala Gln Gly Val Gly Ile Pro Glu Asp Ser Ile
145                 150                 155                 160

Phe Thr Met Ala Asp Arg Gly Glu Cys Val Pro Gly Glu Gln Glu Pro
```

165                 170                 175

Glu Pro Ile Leu Ile Pro Arg
            180

<210> SEQ ID NO 15
<211> LENGTH: 183
<212> TYPE: PRT
<213> ORGANISM: Artificial Sequence
<220> FEATURE:
<223> OTHER INFORMATION: Description of Artificial Sequence: Synthetic
      a1m mutein D1E1 polypeptide

<400> SEQUENCE: 15

Gly Pro Val Pro Thr Pro Pro Asp Asn Ile Gln Val Gln Glu Asn Phe
1               5                   10                  15

Asn Ile Ser Gln Ile Tyr Gly Lys Trp Tyr Asn Leu Ala Ile Gly Ser
            20                  25                  30

Thr His Pro Lys Gln Lys Lys Ile Met Asp Arg Met Thr Val Ile Thr
        35                  40                  45

Leu Val Leu Gly Glu Gly Ala Thr Glu Ala Glu Ile Ser Val Thr Glu
    50                  55                  60

Thr Arg Trp Arg Lys Gly Val Cys Trp Glu Phe Ser Arg Ala Tyr Glu
65                  70                  75                  80

Lys Thr Asp Thr Asp Gly Lys Phe Leu Ile His Lys Ser Lys His Asn
                85                  90                  95

Asn Thr Met Glu Ser Tyr Val Val His Thr Asn Tyr Asp Glu Tyr Ala
            100                 105                 110

Ile Phe Leu Thr Lys Met Phe Ser Arg Gln His Gly Pro Trp Ile Met
        115                 120                 125

Ala Glu Leu Tyr Gly Arg Ala Pro Gln Leu Arg Glu Thr Leu Leu Gln
    130                 135                 140

Asp Phe Arg Val Val Ala Gln Gly Val Gly Ile Pro Glu Asp Ser Ile
145                 150                 155                 160

Phe Thr Met Ala Asp Arg Gly Glu Cys Val Pro Gly Glu Gln Glu Pro
                165                 170                 175

Glu Pro Ile Leu Ile Pro Arg
            180

<210> SEQ ID NO 16
<211> LENGTH: 183
<212> TYPE: PRT
<213> ORGANISM: Artificial Sequence
<220> FEATURE:
<223> OTHER INFORMATION: Description of Artificial Sequence: Synthetic
      a1m mutein D1H3 polypeptide

<400> SEQUENCE: 16

Gly Pro Val Pro Thr Pro Pro Asp Asn Ile Gln Val Gln Glu Asn Phe
1               5                   10                  15

Asn Ile Ser Gln Ile Tyr Gly Lys Trp Tyr Asn Leu Ala Ile Gly Ser
            20                  25                  30

Thr Ile Pro Thr Lys Lys Lys Ile Met Asp Arg Met Thr Val Asp Thr
        35                  40                  45

Leu Val Leu Gly Glu Gly Ala Thr Glu Ala Glu Ile Ser Met Thr Gly
    50                  55                  60

Thr Arg Trp Arg Lys Gly Val Cys Ala Glu Trp Gly Tyr Ala Tyr Glu
65                  70                  75                  80

Lys Thr Asp Thr Asp Gly Lys Phe Leu Asn His Lys Ser Lys His Asn

```
                    85                  90                  95
Tyr Thr Met Glu Ser Tyr Val Val His Thr Asn Tyr Asp Glu Tyr Ala
                100                 105                 110

Ile Phe Leu Phe Lys Met Phe Ser Arg Gln His Gly Pro Trp Ile Val
            115                 120                 125

Ala Gln Leu Tyr Gly Arg Ala Pro Gln Leu Arg Glu Thr Leu Leu Gln
        130                 135                 140

Asp Phe Arg Val Val Ala Gln Gly Val Gly Ile Pro Glu Asp Ser Ile
145                 150                 155                 160

Phe Thr Met Ala Asp Arg Gly Glu Cys Val Pro Gly Glu Gln Glu Pro
                165                 170                 175

Glu Pro Ile Leu Ile Pro Arg
            180

<210> SEQ ID NO 17
<211> LENGTH: 183
<212> TYPE: PRT
<213> ORGANISM: Artificial Sequence
<220> FEATURE:
<223> OTHER INFORMATION: Description of Artificial Sequence: Synthetic
      a1m mutein D1H3 polypeptide

<400> SEQUENCE: 17

Gly Pro Val Pro Thr Pro Pro Asp Asn Ile Gln Val Gln Glu Asn Phe
1               5                   10                  15

Asn Ile Ser Gln Ile Tyr Gly Lys Trp Tyr Asn Leu Ala Ile Gly Ser
            20                  25                  30

Thr Phe Pro Trp His Lys Lys Ile Met Asp Arg Met Thr Val Tyr Thr
        35                  40                  45

Leu Val Leu Gly Glu Gly Ala Thr Glu Ala Glu Ile Ser Asn Thr Glu
    50                  55                  60

Thr Arg Trp Arg Lys Gly Val Cys Leu Glu His Ser Arg Ala Tyr Glu
65                  70                  75                  80

Lys Thr Asp Thr Asp Gly Lys Phe Leu Lys His Lys Ser Lys His Asn
                85                  90                  95

Glu Thr Trp Glu Ser Tyr Val Val His Thr Asn Tyr Asp Glu Tyr Ala
                100                 105                 110

Ile Phe Leu Ser Lys Asp Phe Ser Arg Gln His Gly Pro Pro Ile Glu
            115                 120                 125

Ala Met Leu Tyr Gly Arg Ala Pro Gln Leu Arg Glu Thr Leu Leu Gln
        130                 135                 140

Asp Phe Arg Val Val Ala Gln Gly Val Gly Ile Pro Glu Asp Ser Ile
145                 150                 155                 160

Phe Thr Met Ala Asp Arg Gly Glu Cys Val Pro Gly Glu Gln Glu Pro
                165                 170                 175

Glu Pro Ile Leu Ile Pro Arg
            180

<210> SEQ ID NO 18
<211> LENGTH: 182
<212> TYPE: PRT
<213> ORGANISM: Artificial Sequence
<220> FEATURE:
<223> OTHER INFORMATION: Description of Artificial Sequence: Synthetic
      a1m mutein C1A1 polypeptide

<400> SEQUENCE: 18

Gly Pro Val Pro Thr Pro Pro Asp Asn Ile Gln Val Gln Glu Asn Phe
```

```
1               5                   10                  15
Asn Ile Ser Gln Ile Tyr Gly Lys Trp Tyr Asn Leu Ala Ile Gly Ser
            20                  25                  30

Thr Ser Pro His Lys Lys Ile Met Asp Arg Met Thr Val Asp Thr Leu
            35                  40                  45

Val Leu Gly Glu Gly Ala Thr Glu Ala Glu Ile Ser Ala Thr Ile Thr
        50                  55                  60

Arg Trp Arg Lys Gly Val Cys Glu Glu His Ser Tyr Ala Tyr Glu Lys
65                  70                  75                  80

Thr Asp Thr Asp Gly Lys Phe Leu Trp His Lys Ser Lys His Asn Glu
            85                  90                  95

Thr Val Glu Ser Tyr Val Val His Thr Asn Tyr Asp Glu Tyr Ala Ile
            100                 105                 110

Phe Leu Ile Lys Trp Phe Ser Arg Gln His Gly Pro His Ile Glu Ala
            115                 120                 125

Trp Leu Tyr Gly Arg Ala Pro Gln Leu Arg Glu Thr Leu Leu Gln Asp
        130                 135                 140

Phe Arg Val Val Ala Gln Gly Val Gly Ile Pro Glu Asp Ser Ile Phe
145                 150                 155                 160

Thr Met Ala Asp Arg Gly Glu Cys Val Pro Gly Glu Gln Glu Pro Glu
            165                 170                 175

Pro Ile Leu Ile Pro Arg
            180
```

<210> SEQ ID NO 19
<211> LENGTH: 182
<212> TYPE: PRT
<213> ORGANISM: Artificial Sequence
<220> FEATURE:
<223> OTHER INFORMATION: Description of Artificial Sequence: Synthetic
      alm mutein C1D1 polypeptide

<400> SEQUENCE: 19

```
Gly Pro Val Pro Thr Pro Pro Asp Asn Ile Gln Val Gln Glu Asn Phe
1               5                   10                  15

Asn Ile Ser Gln Ile Tyr Gly Lys Trp Tyr Asn Leu Ala Ile Gly Ser
            20                  25                  30

Thr Pro Phe Ser Lys Lys Ile Met Asp Arg Met Thr Val Asp Thr Leu
            35                  40                  45

Val Leu Gly Glu Gly Ala Thr Glu Ala Glu Ile Ser Val Thr Phe Thr
        50                  55                  60

Arg Trp Arg Lys Gly Val Cys Tyr Glu Lys Ser Glu Ala Tyr Glu Lys
65                  70                  75                  80

Thr Asp Thr Asp Gly Lys Phe Leu Leu His Lys Ser Lys His Asn Gln
            85                  90                  95

Thr Ile Glu Ser Tyr Val Val His Thr Asn Tyr Asp Glu Tyr Ala Ile
            100                 105                 110

Phe Leu Ile Lys Glu Phe Ser Arg Gln His Gly Pro Asn Ile Val Ala
            115                 120                 125

Phe Leu Tyr Gly Arg Ala Pro Gln Leu Arg Glu Thr Leu Leu Gln Asp
        130                 135                 140

Phe Arg Val Val Ala Gln Gly Val Gly Ile Pro Glu Asp Ser Ile Phe
145                 150                 155                 160

Thr

Pro Ile Leu Ile Pro Arg
             180

<210> SEQ ID NO 20
<211> LENGTH: 4978
<212> TYPE: DNA
<213> ORGANISM: Artificial Sequence
<220> FEATURE:
<223> OTHER INFORMATION: Description of Artificial Sequence: Synthetic
      plasmid pNGAL 108 polynucleotide

<400> SEQUENCE: 20

```
ccatcgaatg gccagatgat taattcctaa ttttgttga cactctatca ttgatagagt      60
tattttacca ctccctatca gtgatagaga aagtgaaat gaatagttcg acaaaaatct     120
agataacgag gcaaaaaat gaaaagaca gctatcgcga ttgcagtggc tctggctggc     180
ttcgctaccg tagcgcaggc cggccctgtg ccaacgccgc ccgacaatat ccaagtgcag    240
gaaaacttca atatctccca gatctatggg aagtggtaca acctggccat cggttccacc    300
agcccctggc tgaagaagat catggacagg atgacagtga gcacgctggt gctgggagag    360
ggcgctacag aggcggagat cagcatgacc agcactcgtt ggcggaaagg tgtctgtgag    420
gagacgtctg gagcttatga gaaaacagat actgatggga gtttctcta tcacaaatcc    480 aaatggaaca taaccatgga gtcctatgtg gtccacacca actatgatga gtatgccatt    540
ttcctgacca agaaattcag ccgccatcat ggacccacca ttactgccaa gctctacggg    600
cgggcgccgc agctgaggga aactctcctg caggacttca gagtggttgc ccagggtgtt    660
ggcatccctg aggactccat cttcaccatg gctgaccgag tgaatgtgt ccctggggag    720 caggaaccag agcccatctt aatcccgaga gcgcttggc gtcacccgca gttcggtggg    780
gcctagactg ttgaaagttg tttagcaaaa ccccatacag aaaattcatt tactaacgtc    840
tggaaagacg acaaaacttt agatcgttac gctaactatg agggctgtct gtggaatgct    900
acaggcgttg tagtttgtac tggtgacgaa actcagtgtt acggtacatg ggttcctatt    960
gggcttgcta tccctgaaaa tgagggtggt ggctctgagg gtggcggttc tgagggtggc   1020
ggttctgagg gtggcggtac taaacctcct gagtacggtg atacacctat tccgggctat   1080
acttatatca accctctcga cggcacttat ccgcctggta ctgagcaaaa ccccgctaat   1140
cctaatcctt tcttgagga gtctcagcct cttaatactt tcatgtttca gaataatagg   1200
ttccgaaata ggcagggggc attaactgtt tatacgggca ctgttactca aggcactgac   1260
cccgttaaaa cttattacca gtacactcct gtatcatcaa aagccatgta tgacgcttac   1320
tggaacggta aattcagaga ctgcgctttc cattctggct ttaatgagga tccattcgtt   1380
tgtgaatatc aaggccaatc gtctgacctg cctcaacctc ctgtcaatgc tggcggcggc   1440
tctggtggtg gttctggtgg cggctctgag ggtggtggct ctgagggtgg cggttctgag   1500
ggtggcggct ctgagggagg cggttccggt ggtggctctg gttccggtga ttttgattat   1560
gaaaagatgg caaacgctaa taaggggct atgaccgaaa atgccgatga aaacgcgcta   1620
cagtctgacg ctaaaggcaa acttgattct gtcgctactg attacggtgc tgctatcgat   1680
ggtttcattg gtgacgtttc cggccttgct aatggtaatg gtgctactgg tgatttttgct   1740 ggctctaatt cccaaatggc tcaagtcggt gacggtgata attcaccttt aatgaataat   1800
ttccgtcaat atttaccttc cctccctcaa tcggttgaat gtcgcccttt gtctttggc   1860 gctggtaaac catatgaatt ttctattgat tgtgacaaaa taacttatt ccgtggtgtc   1920 tttgcgtttc ttttatatgt tgccaccttt atgtatgtat tttctacgtt tgctaacata   1980
```

```
ctgcgtaata aggagtctta ataagcttga cctgtgaagt gaaaaatggc gcacattgtg    2040
cgacattttt tttgtctgcc gtttaccgct actgcgtcac ggatctccac gcgccctgta    2100
gcggcgcatt aagcgcggcg ggtgtggtgg ttacgcgcag cgtgaccgct acacttgcca    2160 gcgcccuage gcccgctcct ttcgctttct tcccttcctt tctcgccacg ttcgccggct    2220
ttccccgtca agctctaaat cgggggctcc ctttagggtt ccgatttagt gctttacggc    2280
acctcgaccc caaaaaactt gattagggtg atggttcacg tagtgggcca tcgcccugat    2340
agacggtttt tcgccctttg acgttggagt ccacgttctt aatagtgga ctcttgttcc    2400 aaactggaac aacactcaac cctatctcgg tctattcttt tgatttataa gggattttgc    2460
cgatttcggc ctattggtta aaaaatgagc tgatttaaca aaaatttaac gcgaatttta    2520
acaaaatatt aacgcttaca atttcaggtg cacttttcg gggaaatgtg cgcggaaccc    2580
ctatttgttt attttctaa atacattcaa atatgtatcc gctcatgaga caataaccct    2640
gataaatgct tcaataatat tgaaaaagga agagtatgag tattcaacat ttccgtgtcg    2700
cccttattcc cttttttgcg cattttgcc ttcctgtttt tgctcaccca gaaacgctgg    2760
tgaaagtaaa agatgctgaa gatcagttgg gtgcacgagt gggttacatc gaactggatc    2820
tcaacagcgg taagatcctt gagagttttc gccccgaaga acgttttcca atgatgagca    2880
cttttaaagt tctgctatgt ggcgcggtat tatcccgtat tgacgccggg caagagcaac    2940
tcggtcgccg catacactat tctcagaatg acttggttga gtactcacca gtcacagaaa    3000
agcatcttac ggatggcatg acagtaagag aattatgcag tgctgccata accatgagtg    3060
ataacactgc ggccaactta cttctgacaa cgatcggagg accgaaggag ctaaccgctt    3120
ttttgcacaa catgggggat catgtaactc gccttgatcg ttgggaaccg gagctgaatg    3180
aagccatacc aaacgacgag cgtgacacca cgatgcctgt agcaatggca acaacgttgc    3240
gcaaactatt aactggcgaa ctacttactc tagcttcccg gcaacaattg atagactgga    3300
tggaggcgga taaagttgca ggaccacttc tgcgctcggc ccttccggct ggctggttta    3360
ttgctgataa atctggagcc ggtgagcgtg gctctcgcgg tatcattgca gcactggggc    3420
cagatggtaa gccctcccgt atcgtagtta tctacacgac ggggagtcag gcaactatgg    3480
atgaacgaaa tagacagatc gctgagatag gtgcctcact gattaagcat tggtaggaat    3540
taatgatgtc tcgtttagat aaaagtaaag tgattaacag cgcattagag ctgcttaatg    3600
aggtcggaat cgaaggttta acaacccgta aactcgccca gaagctaggt gtagagcagc    3660
ctacattgta ttggcatgta aaaaataagc gggctttgct cgacgcctta gccattgaga    3720
tgttagatag gcaccatact cacttttgcc ctttagaagg ggaaagctgg caagattttt    3780
tacgtaataa cgctaaaagt tttagatgtg ctttactaag tcatcgcgat ggagcaaaag    3840
tacatttagg tacacggcct acagaaaaac agtatgaaac tctcgaaaat caattagcct    3900
ttttatgcca acaaggtttt tcactagaga atgcattata tgcactcagc gcagtggggc    3960
attttacttt aggttgcgta ttggaagatc aagagcatca agtcgctaaa gaagaaaggg    4020
aaacacctac tactgatagt atgccgccat tattacgaca agctatcgaa ttatttgatc    4080
accaaggtgc agagccagcc ttcttattcg gccttgaatt gatcatatgc ggattagaaa    4140
aacaacttaa atgtgaaagt gggtcttaaa agcagcataa ccttttttccg tgatggtaac    4200 ttcactagtt taaaggatc taggtgaaga tccttttttga taatctcatg accaaaatcc    4260
cttaacgtga gttttcgttc cactgagcgt cagacccgt agaaaagatc aaaggatctt    4320
```

```
cttgagatcc tttttttctg cgcgtaatct gctgcttgca aacaaaaaaa ccaccgctac      4380
cagcggtggt ttgtttgccg gatcaagagc taccaactct ttttccgaag gtaactggct      4440
tcagcagagc gcagatacca aatactgtcc ttctagtgta gccgtagtta ggccaccact      4500
tcaagaactc tgtagcaccg cctacatacc tcgctctgct aatcctgtta ccagtggctg      4560
ctgccagtgg cgataagtcg tgtcttaccg ggttggactc aagacgatag ttaccggata      4620
aggcgcagcg gtcgggctga acggggggtt cgtgcacaca gcccagcttg gagcgaacga      4680
cctacaccga actgagatac ctacagcgtg agctatgaga aagcgccacg cttcccgaag      4740
ggagaaaggc ggacaggtat ccggtaagcg gcagggtcgg aacaggagag cgcacgaggg      4800
agcttccagg gggaaacgcc tggtatcttt atagtcctgt cgggtttcgc cacctctgac      4860
ttgagcgtcg atttttgtga tgctcgtcag ggggggcggag cctatggaaa aacgccagca      4920
acgcggcctt tttacggttc ctggccttt tgctggcctt tgctcacatg acccgaca         4978

<210> SEQ ID NO 21
<211> LENGTH: 3760
<212> TYPE: DNA
<213> ORGANISM: Artificial Sequence
<220> FEATURE:
<223> OTHER INFORMATION: Description of Artificial Sequence: Synthetic
      plasmid palm2 polynucleotide

<400> SEQUENCE: 21
ccatcgaatg gccagatgat taattcctaa ttttgttga cactctatca ttgatagagt        60
tattttacca ctccctatca gtgatagaga aagtgaaat gaatagttcg acaaaaatct       120
agataacgag ggcaaaaaat gaaaaagaca gctatcgcga ttgcagtggc actggctggt      180
ttcgctaccg tagcgcaggc cggccctgtg ccaacgccgc ccgacaatat ccaagtgcag      240
gaaaacttca atatctccca gatctatggg aagtggtaca acctgccat cggttccacc       300 agcccctggc tgaagaagat catggacagg atgacagtga gcacgctggt gctgggagag      360
ggcgctacag aggcggagat cagcatgacc agcactcgtt ggcggaaagg tgtctgtgag      420
gagacgtctg gagcttatga gaaaacagat actgatggga gtttctcta tcacaaatcc       480 aaatggaaca taaccatgga gtcctatgtg gtccacacca actatgatga gtatgccatt      540
ttcctgacca agaaattcag ccgccatcat ggacccacca ttactgccaa gctctacggg      600
cgggcgccgc agctgaggga aactctcctg caggacttca gagtggttgc ccagggtgtt      660
ggcatccctg aggactccat cttcaccatg gctgaccgag gtgaatgtgt ccctggggag      720
caggaaccag agcccatctt aatcccgaga agcgcttggt ctcacccgca gttcgaaaaa      780
taataagctt gacctgtgaa gtgaaaaatg gcgcacattg tgcgacattt ttttgtctg      840 ccgtttaccg ctactgcgtc acggatctcc acgcgccctg tagcggcgca ttaagcgcgg      900
cgggtgtggt ggttacgcgc agcgtgaccg ctacacttgc cagcgcccta gcgcccgctc      960
ctttcgcttt cttcccttcc tttctcgcca cgttcgccgg ctttccccgt caagctctaa     1020
atcgggggct ccctttaggg ttccgattta gtgctttacg gcacctcgac cccaaaaaac     1080
ttgattaggg tgatggttca cgtagtgggc catcgccctg atagacggtt tttcgccctt     1140
tgacgttgga gtccacgttc tttaatagtg gactcttgtt ccaaactgga acaacactca     1200
accctatctc ggtctattct tttgatttat aagggatttt gccgatttcg gcctattggt     1260
taaaaaatga gctgatttaa caaaaattta acgcgaattt aacaaaata ttaacgttta      1320 caatttcagg tggcactttt cggggaaatg tgcgcggaac cctatttgt ttattttct        1380
```

```
aaatacattc aaatatgtat ccgctcatga gacaataacc ctgataaatg cttcaataat    1440
attgaaaaag gaagagtatg agtattcaac atttccgtgt cgcccttatt ccctttttg     1500
cggcattttg ccttcctgtt tttgctcacc cagaaacgct ggtgaaagta aaagatgctg    1560
aagatcagtt gggtgcacga gtgggttaca tcgaactgga tctcaacagc ggtaagatcc    1620
ttgagagttt tcgccccgaa gaacgttttc caatgatgag cacttttaaa gttctgctat    1680
gtggcgcggt attatcccgt attgacgccg ggcaagagca actcggtcgc cgcatacact    1740
attctcagaa tgacttggtt gagtactcac cagtcacaga aaagcatctt acggatggca    1800
tgacagtaag agaattatgc agtgctgcca taaccatgag tgataacact gcggccaact    1860
tacttctgac aacgatcgga ggaccgaagg agctaaccgc ttttttgcac aacatggggg    1920
atcatgtaac tcgccttgat cgttgggaac cggagctgaa tgaagccata ccaaacgacg    1980
agcgtgacac cacgatgcct gtagcaatgg caacaacgtt gcgcaaacta ttaactggcg    2040
aactacttac tctagcttcc cggcaacaat tgatagactg gatggaggcg gataaagttg    2100
caggaccact tctgcgctcg gcccttccgg ctggctggtt tattgctgat aaatctggag    2160
ccggtgagcg tggctctcgc ggtatcattg cagcactggg gccagatggt aagccctccc    2220
gtatcgtagt tatctacacg acggggagtc aggcaactat ggatgaacga atagacaga    2280
tcgctgagat aggtgcctca ctgattaagc attggtagga attaatgatg tctcgtttag    2340
ataaaagtaa agtgattaac agcgcattag agctgcttaa tgaggtcgga atcgaaggtt    2400
taacaacccg taaactcgcc cagaagctag gtgtagagca gcctacattg tattggcatg    2460
taaaaaataa gcgggctttg ctcgacgcct tagccattga gatgttagat aggcaccata    2520
ctcactttg cccctttagaa ggggaaagct ggcaagattt tttacgtaat aacgctaaaa    2580
gttttagatg tgctttacta agtcatcgcg atggagcaaa agtacattta ggtacacggc    2640
ctacagaaaa acagtatgaa actctcgaaa atcaattagc cttttatgc caacaaggtt    2700
tttcactaga gaatgcatta tatgcactca gcgcagtggg gcattttact ttaggttgcg    2760
tattggaaga tcaagagcat caagtcgcta aagaagaaag ggaaacacct actactgata    2820
gtatgccgcc attattacga caagctatcg aattatttga tcaccaaggt gcagagccag    2880
ccttcttatt cggccttgaa ttgatcatat gcggattaga aaaacaactt aaatgtgaaa    2940
gtgggtctta aaagcagcat aaccttttc cgtgatggta acttcactag tttaaaagga    3000
tctaggtgaa gatcctttt gataatctca tgaccaaaat cccttaacgt gagttttcgt    3060
tccactgagc gtcagacccc gtagaaaaga tcaaaggatc ttcttgagat cctttttttc    3120
tgcgcgtaat ctgctgcttg caaacaaaaa aaccaccgct accagcggtg gtttgtttgc    3180
cggatcaaga gctaccaact cttttccga aggtaactgg cttcagcaga gcgcagatac    3240
caaatactgt ccttctagtg tagccgtagt taggccacca cttcaagaac tctgtagcac    3300
cgcctacata cctcgctctg ctaatcctgt taccagtggc tgctgccagt ggcgataagt    3360
cgtgtcttac cgggttggac tcaagacgat agttaccgga taaggcgcag cggtcgggct    3420
gaacggggg ttcgtgcaca cagcccagct tggagcgaac gacctacacc gaactgagat    3480
acctacagcg tgagctatga gaaagcgcca cgcttcccga agggagaaag gcggacaggt    3540
atccggtaag cggcagggtc ggaacaggag agcgcacgag ggagcttcca ggggaaacg     3600
cctggtatct ttatagtcct gtcgggtttc gccacctctg acttgagcgt cgatttttgt    3660
gatgctcgtc agggggggcgg agcctatgga aaaacgccag caacgcgcc tttttacggt    3720
tcctggcctt tgctggcct tttgctcaca tgacccgaca                           3760
```

<210> SEQ ID NO 22
<211> LENGTH: 173
<212> TYPE: PRT
<213> ORGANISM: Homo sapiens

<400> SEQUENCE: 22

Ala Ser Pro Ile Ser Thr Ile Gln Pro Lys Ala Asn Phe Asp Ala Gln
1               5                   10                  15

Gln Phe Ala Gly Thr Trp Leu Leu Val Ala Val Gly Ser Ala Ala Arg
            20                  25                  30

Phe Leu Gln Glu Gln Gly His Arg Ala Glu Ala Thr Thr Leu His Val
        35                  40                  45

Ala Pro Gln Gly Thr Ala Met Ala Val Ser Thr Phe Arg Lys Leu Asp
    50                  55                  60

Gly Ile Cys Trp Gln Val Arg Gln Leu Tyr Gly Asp Thr Gly Val Leu
65                  70                  75                  80

Gly Arg Phe Leu Leu Gln Ala Arg Gly Ala Arg Gly Ala Val His Val
                85                  90                  95

Val Val Ala Glu Thr Asp Tyr Gln Ser Phe Ala Val Leu Tyr Leu Glu
            100                 105                 110

Arg Ala Gly Gln Leu Ser Val Lys Leu Tyr Ala Arg Ser Leu Pro Val
        115                 120                 125

Ser Asp Ser Val Leu Ser Gly Phe Glu Gln Arg Val Gln Glu Ala His
    130                 135                 140

Leu Thr Glu Asp Gln Ile Phe Tyr Phe Pro Lys Tyr Gly Phe Cys Glu
145                 150                 155                 160

Ala Ala Asp Gln Phe His Val Leu Asp Glu Val Arg Arg
                165                 170

<210> SEQ ID NO 23
<211> LENGTH: 162
<212> TYPE: PRT
<213> ORGANISM: Homo sapiens

<400> SEQUENCE: 23

Ser Val Gln Pro Asn Phe Gln Gln Asp Lys Phe Leu Gly Arg Trp Phe
1               5                   10                  15

Ser Ala Gly Leu Ala Ser Asn Ser Ser Trp Leu Arg Glu Lys Lys Ala
            20                  25                  30

Ala Leu Ser Met Ala Lys Ser Val Val Ala Pro Ala Thr Asp Gly Gly
        35                  40                  45

Leu Asn Leu Thr Ser Thr Phe Leu Arg Lys Asn Gln Cys Glu Thr Arg
    50                  55                  60

Thr Met Leu Leu Gln Pro Ala Gly Ser Leu Gly Ser Tyr Ser Tyr Arg
65                  70                  75                  80

Ser Pro His Trp Gly Ser Thr Tyr Ser Val Ser Val Val Glu Thr Asp
                85                  90                  95

Tyr Asp Gln Tyr Ala Leu Leu Tyr Ser Gln Gly Ser Lys Gly Pro Gly
            100                 105                 110

Glu Asp Phe Arg Met Ala Thr Leu Tyr Ser Arg Thr Gln Thr Pro Arg
        115                 120                 125

Ala Glu Leu Lys Glu Lys Phe Thr Ala Phe Cys Lys Ala Gln Gly Phe
    130                 135                 140

Thr Glu Asp Thr Ile Val Phe Leu Pro Gln Thr Asp Lys Cys Met Thr
145                 150                 155                 160

Glu Gln

<210> SEQ ID NO 24
<211> LENGTH: 161
<212> TYPE: PRT
<213> ORGANISM: Homo sapiens

<400> SEQUENCE: 24

Thr Ala Gln Ala Glu Val Leu Leu Gln Pro Asp Phe Asn Ala Glu Lys
1               5                   10                  15

Phe Ser Gly Leu Trp Tyr Val Val Ser Met Ala Ser Asp Cys Arg Val
            20                  25                  30

Phe Leu Gly Lys Lys Asp His Leu Ser Met Ser Thr Arg Ala Ile Arg
        35                  40                  45

Pro Thr Glu Glu Gly Gly Leu His Val His Met Glu Phe Pro Gly Ala
    50                  55                  60

Asp Gly Cys Asn Gln Val Asp Ala Glu Tyr Leu Lys Val Gly Ser Glu
65                  70                  75                  80

Gly His Phe Arg Val Pro Ala Leu Gly Tyr Leu Asp Val Arg Ile Val
                85                  90                  95

Asp Thr Asp Tyr Ser Ser Phe Ala Val Leu Tyr Ile Tyr Lys Glu Leu
            100                 105                 110

Glu Gly Ala Leu Ser Thr Met Val Gln Leu Tyr Ser Arg Thr Gln Asp
        115                 120                 125

Val Ser Pro Gln Ala Leu Lys Ser Phe Gln Asp Phe Tyr Pro Thr Leu
    130                 135                 140

Gly Leu Pro Lys Asp Met Met Val Met Leu Pro Gln Ser Asp Ala Cys
145                 150                 155                 160

Asn

<210> SEQ ID NO 25
<211> LENGTH: 181
<212> TYPE: PRT
<213> ORGANISM: Gallus gallus

<400> SEQUENCE: 25

Thr Pro Val Gly Asp Gln Asp Glu Asp Ile Gln Val Gln Glu Asn Phe
1               5                   10                  15

Glu Pro Glu Arg Met Tyr Gly Lys Trp Tyr Asp Val Ala Val Gly Thr
            20                  25                  30

Thr Cys Lys Trp Met Lys Asn Tyr Lys Glu Lys Phe Ser Met Gly Thr
        35                  40                  45

Leu Val Leu Gly Pro Gly Pro Ser Ala Asp Gln Ile Ser Thr Ile Ser
    50                  55                  60

Thr Arg Leu Arg Gln Gly Asp Cys Lys Arg Val Ser Gly Glu Tyr Gln
65                  70                  75                  80

Lys Thr Asp Thr Pro Gly Lys Tyr Thr Tyr Asn Pro Lys Trp Asp
                85                  90                  95

Val Ser Ile Lys Ser Tyr Val Leu Arg Thr Asn Tyr Glu Glu Tyr Ala
            100                 105                 110

Val Ile Leu Met Lys Lys Thr Ser Asn Phe Gly Pro Thr Thr Thr Leu
        115                 120                 125

Lys Leu Tyr Gly Arg Ser Pro Glu Leu Arg Glu Glu Leu Thr Glu Ala
    130                 135                 140

Phe Gln Gln Leu Ala Leu Glu Met Gly Ile Pro Ala Asp Ser Val Phe

```
145                 150                 155                 160
Ile Leu Ala Asn Lys Gly Glu Cys Val Pro Gln Glu Thr Ala Thr Ala
                165                 170                 175

Pro Glu Glu Gln Arg
            180

<210> SEQ ID NO 26
<211> LENGTH: 181
<212> TYPE: PRT
<213> ORGANISM: Meleagris gallopavo

<400> SEQUENCE: 26

Thr Pro Ile Gly Asp Gln Asp Glu Asp Ile Gln Val Gln Glu Asn Phe
1               5                   10                  15

Glu Pro Glu Arg Met Tyr Gly Lys Trp Tyr Asp Val Ala Val Ala Thr
            20                  25                  30

Thr Cys Lys Trp Met Lys Asn Tyr Lys Glu Lys Phe Ser Met Gly Thr
        35                  40                  45

Leu Val Leu Gly Pro Gly Pro Ser Thr Asp Gln Ile Ser Thr Ile Ser
    50                  55                  60

Thr Arg Leu Arg Gln Gly Asp Cys Lys Arg Val Ser Gly Glu Tyr Gln
65                  70                  75                  80

Lys Thr Asp Thr Pro Gly Lys Tyr Thr Tyr Tyr Asn Pro Lys Trp Asp
                85                  90                  95

Val Ser Ile Lys Ser Tyr Val Leu Arg Thr Asn Tyr Glu Glu Tyr Ala
            100                 105                 110

Val Ile Leu Met Lys Lys Thr Ser Asn Phe Gly Pro Thr Thr Thr Leu
        115                 120                 125

Lys Leu Tyr Gly Arg Ser Pro Glu Leu Arg Glu Glu Leu Thr Glu Ala
    130                 135                 140

Phe Gln Gln Leu Ala Leu Glu Met Gly Ile Pro Ala Asp Ser Ile Phe
145                 150                 155                 160

Ile Leu Ala Asn Lys Gly Glu Cys Val Pro Gln Glu Thr Ala Asn Ala
                165                 170                 175

Pro Glu Glu Gln Arg
            180

<210> SEQ ID NO 27
<211> LENGTH: 183
<212> TYPE: PRT
<213> ORGANISM: Pongo abelii

<400> SEQUENCE: 27

Gly Pro Val Pro Thr Pro Pro Asp Asn Ile Gln Val Gln Glu Asn Phe
1               5                   10                  15

Asn Ile Ser Arg Ile Tyr Gly Lys Trp Tyr Asn Leu Ala Ile Gly Ser
            20                  25                  30

Thr Cys Pro Trp Leu Lys Lys Ile Met Asp Arg Met Thr Val Ser Thr
        35                  40                  45

Leu Val Leu Gly Glu Gly Ala Thr Glu Ala Glu Ile Ser Met Thr Ser
    50                  55                  60

Thr Arg Trp Arg Lys Gly Val Cys Glu Glu Thr Ser Gly Ala Tyr Glu
65                  70                  75                  80

Lys Thr Asp Thr Asp Gly Lys Phe Leu Tyr His Lys Ser Lys Trp Asn
                85                  90                  95

Ile Thr Met Glu Ser Tyr Val Val His Thr Asn Tyr Asp Glu Tyr Ala
```

```
                100                 105                 110
Ile Phe Leu Thr Lys Lys Phe Ser Arg Arg His Gly Pro Thr Ile Thr
            115                 120                 125

Ala Lys Leu Tyr Gly Arg Ala Pro Gln Leu Arg Glu Thr Leu Leu Gln
        130                 135                 140

Asp Phe Arg Val Val Ala Gln Gly Val Gly Ile Pro Glu Asp Ser Ile
145                 150                 155                 160

Phe Thr Met Ala Asp Arg Gly Glu Cys Val Pro Gly Glu Gln Glu Pro
                165                 170                 175

Glu Pro Ile Leu Ile Pro Arg
            180

<210> SEQ ID NO 28
<211> LENGTH: 183
<212> TYPE: PRT
<213> ORGANISM: Nomascus leucogenys

<400> SEQUENCE: 28

Ser Cys Val Pro Cys Pro His Pro Gly Leu Thr Val Asp Arg His Leu
1               5                   10                  15

Gly Trp His Arg Ile Tyr Gly Lys Trp Tyr Asn Leu Ala Ile Gly Ser
            20                  25                  30

Thr Cys Pro Trp Leu Lys Lys Ile Met Asp Arg Met Thr Val Ser Thr
        35                  40                  45

Leu Val Leu Arg Glu Gly Ala Thr Glu Ala Glu Ile Ser Met Thr Ser
    50                  55                  60

Thr Arg Trp Arg Lys Gly Val Cys Glu Glu Thr Ser Gly Ala Tyr Glu
65                  70                  75                  80

Lys Thr Asp Thr Asp Gly Lys Phe Leu Tyr His Lys Ser Lys Trp Asn
                85                  90                  95

Ile Thr Met Glu Ser Tyr Val Val His Thr Asn Tyr Asp Glu Tyr Ala
            100                 105                 110

Ile Phe Leu Thr Lys Lys Phe Ser Arg Arg His Gly Pro Thr Ile Thr
        115                 120                 125

Ala Lys Leu Tyr Gly Arg Ala Pro Gln Leu Arg Glu Thr Leu Leu Gln
    130                 135                 140

Asp Phe Arg Val Val Ala Gln Gly Val Gly Ile Pro Glu Asp Ser Ile
145                 150                 155                 160

Phe Ile Met Ala Asp Arg Gly Glu Cys Val Pro Gly Glu Gln Glu Pro
                165                 170                 175

Glu Pro Ile Leu Ile Pro Arg
            180

<210> SEQ ID NO 29
<211> LENGTH: 183
<212> TYPE: PRT
<213> ORGANISM: Callithrix jacchus

<400> SEQUENCE: 29

Gly Pro Val Pro Thr Pro Pro Glu Gly Ile Gln Val Gln Glu Asn Phe
1               5                   10                  15

Asn Leu Ser Arg Ile Tyr Gly Lys Trp Tyr Asn Leu Ala Ile Gly Ser
            20                  25                  30

Thr Cys Pro Trp Leu Lys Lys Ile Met Asp Arg Leu Lys Val Ser Thr
        35                  40                  45

Leu Val Leu Glu Glu Gly Thr Thr Glu Val Glu Ile Asn Met Thr Ser
```

```
                50                  55                  60
Thr Arg Trp Arg Lys Gly Phe Cys Glu Gln Thr Ser Leu Ala Tyr Glu
 65                  70                  75                  80

Lys Thr Asp Thr Asp Gly Lys Phe Leu Tyr His Lys Ser Lys Trp Asn
                 85                  90                  95

Ile Thr Met Glu Ser Tyr Val Val His Thr Asn Tyr Asp Glu Tyr Ala
                100                 105                 110

Ile Phe Leu Thr Lys Lys Phe Ser Arg His His Gly Pro Thr Ile Thr
                115                 120                 125

Ala Gln Leu Tyr Gly Arg Glu Pro Gln Leu Arg Asp Ser Leu Leu Gln
                130                 135                 140

Asp Phe Arg Val Val Ala Gln Gly Val Gly Ile Pro Glu Asp Ser Ile
145                 150                 155                 160

Phe Thr Met Ala Asp Arg Gly Glu Cys Ile Pro Gly Glu Gln Glu Pro
                165                 170                 175

Gln Pro Ile Leu His Pro Arg
                180

<210> SEQ ID NO 30
<211> LENGTH: 183
<212> TYPE: PRT
<213> ORGANISM: Oryctolagus cuniculus

<400> SEQUENCE: 30

Asp Pro Val Pro Thr Leu Pro Asp Asp Ile Gln Val Gln Glu Asn Phe
 1               5                  10                  15

Glu Leu Ser Arg Ile Tyr Gly Lys Trp Tyr Asn Leu Ala Val Gly Ser
                20                  25                  30

Thr Cys Pro Trp Leu Lys Arg Ile Lys Asp Arg Met Ala Val Ser Thr
                35                  40                  45

Leu Val Leu Gly Glu Gly Thr Ser Glu Thr Glu Ile Ser Met Thr Ser
 50                  55                  60

Thr His Trp Arg Arg Gly Val Cys Glu Glu Ile Ser Gly Ala Tyr Glu
 65                  70                  75                  80

Lys Thr Asp Thr Asp Gly Lys Phe Leu Tyr His Lys Ala Lys Trp Asn
                 85                  90                  95

Leu Thr Met Glu Ser Tyr Val Val His Thr Asn Tyr Asp Glu Tyr Ala
                100                 105                 110

Ile Phe Leu Thr Lys Lys Phe Ser Arg Arg His Gly Pro Thr Ile Thr
                115                 120                 125

Ala Lys Leu Tyr Gly Arg Glu Pro Gln Leu Arg Glu Ser Leu Leu Gln
                130                 135                 140

Glu Phe Arg Glu Val Ala Leu Gly Val Gly Ile Pro Glu Asn Ser Ile
145                 150                 155                 160

Phe Thr Met Ile Asp Arg Gly Glu Cys Val Pro Gly Gln Gln Glu Pro
                165                 170                 175

Lys Pro Ala Pro Val Leu Arg
                180

<210> SEQ ID NO 31
<211> LENGTH: 182
<212> TYPE: PRT
<213> ORGANISM: Mus musculus

<400> SEQUENCE: 31

Asp Pro Ala Ser Thr Leu Pro Asp Ile Gln Val Gln Glu Asn Phe Ser
```

```
            1               5                   10                  15
Glu Ser Arg Ile Tyr Gly Lys Trp Tyr Asn Leu Ala Val Gly Ser Thr
            20                  25                  30

Cys Pro Trp Leu Ser Arg Ile Lys Asp Lys Met Ser Val Ser Thr Leu
            35                  40                  45

Val Leu Gln Glu Gly Ala Thr Glu Thr Glu Ile Ser Met Thr Ser Thr
    50                  55                  60

Arg Trp Arg Arg Gly Val Cys Glu Glu Ile Thr Gly Ala Tyr Gln Lys
65                  70                  75                  80

Thr Asp Ile Asp Gly Lys Phe Leu Tyr His Lys Ser Lys Trp Asn Ile
                85                  90                  95

Thr Leu Glu Ser Tyr Val Val His Thr Asn Tyr Asp Glu Tyr Ala Ile
                100                 105                 110

Phe Leu Thr Lys Lys Ser Ser His His His Gly Leu Thr Ile Thr Ala
                115                 120                 125

Lys Leu Tyr Gly Arg Glu Pro Gln Leu Arg Asp Ser Leu Leu Gln Glu
            130                 135                 140

Phe Lys Asp Val Ala Leu Asn Val Gly Ile Ser Glu Asn Ser Ile Ile
145                 150                 155                 160

Phe Met Pro Asp Arg Gly Glu Cys Val Pro Gly Asp Arg Glu Val Glu
                165                 170                 175

Pro Thr Ser Ile Ala Arg
                180

<210> SEQ ID NO 32
<211> LENGTH: 182
<212> TYPE: PRT
<213> ORGANISM: Rattus norvegicus

<400> SEQUENCE: 32

Asp Asn Val Pro Thr Leu Pro Asp Ile Gln Val Gln Glu Asn Phe Asn
1               5                   10                  15

Glu Ala Arg Ile Tyr Gly Lys Trp Phe Asn Leu Ala Val Gly Ser Thr
            20                  25                  30

Cys Pro Trp Leu Arg Arg Ile Lys Asn Lys Met Ser Val Ser Thr Leu
            35                  40                  45

Val Leu Gln Glu Gly Ala Thr Glu Ala Glu Ile Ser Val Thr Ser Thr
    50                  55                  60

Gln Trp Arg Lys Gly Val Cys Glu Glu Ile Ser Gly Val Tyr Gln Lys
65                  70                  75                  80

Thr Asp Ile Asp Gly Lys Phe Leu Tyr His Lys Ser Lys Trp Asn Ala
                85                  90                  95

Thr Leu Glu Ser Tyr Val Val His Thr Asn Tyr Asp Glu Tyr Ala Ile
                100                 105                 110

Phe Leu Thr Lys Lys Phe Ser His Arg His Gly Pro Thr Ile Thr Ala
                115                 120                 125

Lys Leu Tyr Gly Arg Glu Pro Gln Leu Arg Asp Ser Leu Leu Gln Glu
            130                 135                 140

Phe Arg Glu Val Ala Leu Ser Val Gly Ile Pro Glu Asn Ser Ile Val
145                 150                 155                 160

Phe Met Ala Asp Arg Gly Glu Cys Val Pro Gly Asp Arg Glu Val Glu
                165                 170                 175

Ser Thr Ser Phe Ala Arg
                180
```

<210> SEQ ID NO 33
<211> LENGTH: 182
<212> TYPE: PRT
<213> ORGANISM: Meriones unguiculatus

<400> SEQUENCE: 33

```
Asp Asp Ala Ala Thr Leu Pro Asp Ile Gln Val Gln Glu Asn Phe Ile
1               5                   10                  15

Glu Ser Leu Ile Tyr Gly Lys Trp Phe Asn Leu Ala Val Gly Ser Thr
            20                  25                  30

Cys Pro Trp Leu Arg Arg Ile Lys Asp Lys Met Ser Met Ser Thr Leu
        35                  40                  45

Val Leu Gln Glu Gly Ala Thr Glu Ala Glu Ile Ser Met Thr Ser Thr
    50                  55                  60

Arg Trp Arg Arg Gly Val Cys Glu Glu Ile Ser Gly Ala Tyr Glu Lys
65                  70                  75                  80

Thr Asp Ile Asp Gly Lys Phe Leu Tyr His Lys Ser Lys Trp Asn Ile
                85                  90                  95

Thr Leu Glu Thr Tyr Val Val His Thr Asn Tyr Asp Glu Tyr Ala Ile
            100                 105                 110

Phe Leu Thr Lys Lys Phe Ser His Tyr His Gly Pro Thr Ile Thr Leu
        115                 120                 125

Lys Leu Tyr Gly Arg Glu Pro Lys Leu Arg Asp Ser Leu Leu Leu Glu
    130                 135                 140

Phe Arg Glu Val Ala Leu Ser Met Gly Ile Pro Glu Asn Ser Ile Val
145                 150                 155                 160

Phe Met Ala Asp Lys Gly Glu Cys Val Pro Gly Asp Gln Glu Val Lys
                165                 170                 175

Pro Ser Pro His Leu Arg
            180
```

<210> SEQ ID NO 34
<211> LENGTH: 182
<212> TYPE: PRT
<213> ORGANISM: Mesocricetus auratus

<400> SEQUENCE: 34

```
Asp Pro Val Pro Ala Leu Pro Asp Ile Gln Val Gln Glu Asn Phe Asn
1               5                   10                  15

Glu Ser Arg Ile Tyr Gly Lys Trp Phe Asn Leu Ala Val Gly Ser Thr
            20                  25                  30

Cys Pro Trp Leu Ser Arg Ile Lys Asn Lys Met Ser Met Ser Thr Leu
        35                  40                  45

Val Leu Arg Glu Gly Ala Thr Gly Ala Glu Ile Ser Thr Thr Ser Thr
    50                  55                  60

Arg Trp Arg Arg Gly Val Cys Glu Glu Val Ser Gly Thr Tyr Glu Lys
65                  70                  75                  80

Thr Asp Met Asp Gly Lys Phe Leu Tyr His Lys Ser Lys Trp Asn Val
                85                  90                  95

Thr Leu Glu Ser Tyr Val Val His Thr Asn Tyr Asp Glu Tyr Ala Ile
            100                 105                 110

Phe Leu Thr Lys Lys Phe Ser Arg His His Gly Pro Thr Ile Thr Ala
        115                 120                 125

Lys Leu Tyr Gly Arg Glu Pro Gln Leu Arg Asp Ser Leu Leu Gln Glu
    130                 135                 140
```

```
Phe Arg Glu Val Ala Leu Ser Val Gly Ile Pro Glu Asn Ser Ile Val
145                 150                 155                 160

Phe Met Glu Asp Arg Gly Glu Cys Val Pro Gly Asp Leu Glu Gln Lys
                165                 170                 175

Ser Thr Ser Leu Leu Arg
            180

<210> SEQ ID NO 35
<211> LENGTH: 183
<212> TYPE: PRT
<213> ORGANISM: Bos taurus

<400> SEQUENCE: 35

Ser Ser Val Pro Thr Leu Pro Asp Asp Ile Gln Val Gln Glu Asn Phe
1               5                   10                  15

Asp Leu Ser Arg Ile Tyr Gly Lys Trp Phe Asn Val Ala Val Gly Ser
                20                  25                  30

Thr Cys Pro Trp Leu Lys Arg Phe Lys Glu Lys Met Thr Met Ser Thr
            35                  40                  45

Val Val Leu Ile Ala Gly Pro Thr Ser Lys Glu Ile Ser Val Thr Asn
    50                  55                  60

Thr His Arg Arg Lys Gly Val Cys Glu Ser Ile Ser Gly Thr Tyr Glu
65                  70                  75                  80

Lys Thr Ser Ala Asp Gly Lys Phe Leu Tyr His Lys Ala Lys Trp Asn
                85                  90                  95

Ile Thr Met Glu Ser Tyr Val Val His Thr Asn Tyr Asp Glu Tyr Ala
            100                 105                 110

Ile Phe Leu Thr Lys Lys Leu Ser Arg Arg His Gly Pro Thr Ile Thr
        115                 120                 125

Val Lys Leu Tyr Gly Arg Glu Pro Gln Leu Arg Glu Ser Leu Leu Glu
    130                 135                 140

Glu Phe Arg Glu Val Ala Leu Gly Val Gly Ile Pro Glu Asp Ala Ile
145                 150                 155                 160

Phe Thr Met Pro Asp Arg Gly Glu Cys Val Pro Gly Glu Gln Asp Pro
                165                 170                 175

Val Pro Thr Pro Leu Ser Arg
            180

<210> SEQ ID NO 36
<211> LENGTH: 183
<212> TYPE: PRT
<213> ORGANISM: Sus scrofa

<400> SEQUENCE: 36

Ser Pro Val Leu Thr Leu Pro Asn Asp Ile Gln Val Gln Glu Asn Phe
1               5                   10                  15

Asp Leu Ser Arg Ile Tyr Gly Lys Trp Phe His Val Ala Val Gly Ser
                20                  25                  30

Thr Cys Pro Trp Leu Lys Arg Phe Lys Asp Lys Met Thr Met Gly Thr
            35                  40                  45

Leu Met Leu Gly Glu Gly Ala Thr Glu Arg Glu Ile Ser Val Thr Lys
    50                  55                  60

Thr His Arg Arg Lys Gly Ile Cys Glu Val Ile Ser Gly Ala Tyr Glu
65                  70                  75                  80

Lys Thr Ser Thr Asp Gly Lys Phe Leu Tyr His Lys Ser Lys Trp Asn
                85                  90                  95
```

```
Ile Thr Met Glu Ser Tyr Val Val His Thr Asn Tyr Asp Glu Tyr Ala
            100                 105                 110

Ile Phe Leu Thr Lys Lys Phe Ser Arg His Gly Pro Thr Leu Thr
    115                 120                 125

Ala Lys Leu Tyr Gly Arg Glu Pro Gln Leu Arg Glu Ser Leu Leu Glu
        130                 135                 140

Glu Phe Arg Glu Val Ala Leu Gly Val Gly Ile Pro Glu Asp Ser Ile
145                 150                 155                 160

Phe Thr Met Pro Asp Arg Gly Glu Cys Val Pro Gly Glu Gln Glu Pro
                    165                 170                 175

Glu Pro Thr Leu Leu Ser Arg
            180
```

<210> SEQ ID NO 37
<211> LENGTH: 183
<212> TYPE: PRT
<213> ORGANISM: Ailuropoda melanoleuca

<400> SEQUENCE: 37

```
Ser Pro Val Leu Thr Pro Pro Asp Asp Ile Gln Val Gln Glu Asn Phe
1               5                   10                  15

Asp Ile Ser Arg Met Tyr Gly Lys Trp Phe His Val Ala Met Gly Ser
            20                  25                  30

Thr Cys Pro Trp Leu Lys Lys Phe Met Asp Arg Met Ser Met Ser Thr
        35                  40                  45

Leu Val Leu Gly Glu Gly Ala Thr Asp Gly Glu Ile Ser Met Thr Ser
    50                  55                  60

Thr Arg Trp Arg Gly Ala Cys Glu Glu Ile Ser Gly Ala Tyr Glu
65                  70                  75                  80

Lys Thr Ser Thr Asn Gly Lys Phe Leu Tyr His Lys Pro Lys Trp Asn
                85                  90                  95

Met Thr Met Glu Ser Tyr Val Val His Thr Asn Tyr Asp Glu Tyr Ala
            100                 105                 110

Ile Phe Leu Thr Lys Lys Phe Ser Arg His His Gly Pro Thr Ile Thr
        115                 120                 125

Ala Lys Leu Tyr Gly Arg Gln Pro Gln Leu Arg Glu Ser Leu Leu Glu
    130                 135                 140

Glu Phe Arg Glu Val Ala Leu Gly Val Gly Ile Pro Glu Asp Ser Ile
145                 150                 155                 160

Phe Thr Met Ala Asp Lys Gly Glu Cys Val Pro Gly Glu Gln Glu Pro
                    165                 170                 175

Glu Pro Ser Pro His Arg Arg
            180
```

<210> SEQ ID NO 38
<211> LENGTH: 183
<212> TYPE: PRT
<213> ORGANISM: Felis catus

<400> SEQUENCE: 38

```
Ser Pro Val Leu Thr Pro Pro Asp Asp Ile Gln Val Gln Glu Asn Phe
1               5                   10                  15

Asp Ile Ser Arg Ile Tyr Gly Lys Trp Phe His Val Ala Met Gly Ser
            20                  25                  30

Thr Cys Pro Trp Leu Lys Lys Phe Met Asp Arg Met Ser Met Ser Thr
        35                  40                  45
```

Leu Val Leu Gly Glu Gly Ala Lys Asp Lys Glu Ile Ser Met Thr Ser
 50                  55                  60

Thr Arg Trp Arg Arg Gly Thr Cys Glu Glu Ile Ser Gly Ala Tyr Glu
 65                  70                  75                  80

Lys Thr Asp Thr Asp Gly Lys Phe Leu Tyr His Lys Pro Arg Trp Asn
                 85                  90                  95

Ile Thr Met Glu Ser Tyr Val Val His Thr Asn Tyr Asp Glu Tyr Ala
            100                 105                 110

Ile Leu Leu Thr Lys Lys Phe Ser His His Gly Pro Thr Ile Thr
        115                 120                 125

Ala Lys Leu Tyr Gly Arg Gln Pro Gln Leu Arg Glu Ser Leu Leu Glu
130                 135                 140

Glu Phe Arg Glu Val Ala Leu Gly Val Gly Ile Pro Glu Asp Ser Ile
145                 150                 155                 160

Phe Thr Met Ala Asp Lys Gly Glu Cys Val Pro Gly Glu Gln Glu Pro
                165                 170                 175

Glu Pro Ser Pro Leu Thr Arg
            180

<210> SEQ ID NO 39
<211> LENGTH: 183
<212> TYPE: PRT
<213> ORGANISM: Canis familiaris

<400> SEQUENCE: 39

Ser Pro Val Leu Thr Pro Pro Asp Asp Ile Gln Val Gln Glu Asn Phe
 1               5                  10                  15

Asp Val Ser Arg Ile Tyr Gly Lys Trp Phe His Val Ala Val Gly Ser
                20                  25                  30

Thr Cys Pro Trp Leu Lys Lys Phe Met Asp Arg Met Ser Met Ser Thr
            35                  40                  45

Leu Val Leu Gly Glu Gly Pro Thr Asp Arg Glu Leu Ser Met Thr Ser
 50                  55                  60

Thr Arg Trp Arg Arg Gly Thr Cys Glu Glu Ile Ser Gly Thr Tyr Glu
 65                  70                  75                  80

Ile Thr Gly Thr Ser Gly Lys Phe Leu Tyr His Lys Pro Lys Trp Asn
                 85                  90                  95

Leu Thr Met Glu Ser Tyr Val Val His Thr Asn Tyr Asp Glu Tyr Ala
            100                 105                 110

Ile Phe Leu Thr Lys Lys Phe Ser Arg His His Gly Pro Thr Ile Thr
        115                 120                 125

Ala Lys Leu Tyr Gly Arg Gln Pro Gln Leu Arg Glu Ser Leu Leu Glu
130                 135                 140

Glu Phe Arg Glu Val Ala Leu Gly Val Gly Ile Pro Ala Asp Ala Ile
145                 150                 155                 160

Phe Thr Met Ala Asp Lys Gly Glu Cys Val Pro Gly Glu Gln Glu Pro
                165                 170                 175

Glu Pro Ser Pro Tyr Met Arg
            180

<210> SEQ ID NO 40
<211> LENGTH: 183
<212> TYPE: PRT
<213> ORGANISM: Equus caballus

<400> SEQUENCE: 40

```
Ser Pro Val Pro Thr Pro Ala Asp Ile Gln Val Gln Glu Asn Phe
1               5                   10                  15

Asp Leu Ser Arg Ile Tyr Gly Lys Trp Phe Leu Val Ala Met Gly Ser
            20                  25                  30

Thr Cys Pro Trp Leu Lys Lys Ile Lys Asp Arg Met Thr Ile Ser Thr
        35                  40                  45

Leu Val Leu Gly Glu Gly Ala Thr Asp Gly Glu Ile Ser Thr Thr Ser
    50                  55                  60

Thr Arg Trp Arg Lys Gly Val Cys Glu Glu Ile Ser Gly Thr Tyr Glu
65                  70                  75                  80

Lys Thr Asp Thr Lys Gly Lys Phe Arg Tyr His Lys Ser Lys Trp Asn
                85                  90                  95

Leu Ser Ile Glu Ser Tyr Val Val Gln Thr Asn Tyr Asp Glu Tyr Ala
            100                 105                 110

Ile Phe Leu Ser Lys Lys Phe Ser Arg Arg His Gly Pro Thr Ile Thr
            115                 120                 125

Ala Lys Leu Tyr Gly Arg Asp Arg Gln Leu Arg Glu Ser Leu Leu Asp
            130                 135                 140

Thr Phe Arg Glu Val Ala Leu Gly Val Gly Ile Pro Gly Asp Ser Ile
145                 150                 155                 160

Val Thr Leu Ala Asp Arg Gly Glu Cys Val Pro Gly Glu Gln Glu Pro
                165                 170                 175

Glu Pro Met Pro Phe Ser Arg
            180

<210> SEQ ID NO 41
<211> LENGTH: 183
<212> TYPE: PRT
<213> ORGANISM: Myotis lucifugus

<400> SEQUENCE: 41

Asn Pro Val Pro Thr Pro Ala Asn Ile Gln Val Gln Glu Asn Phe
1               5                   10                  15

Asp Val Ser Arg Phe Tyr Gly Lys Trp Phe His Val Ala Ile Gly Ser
            20                  25                  30

Thr Cys Ser Trp Leu Val Arg Phe Lys Asp Arg Leu Thr Val Ser Thr
        35                  40                  45

Leu Leu Leu Arg Glu Gly Glu Thr Glu Arg Gln Ile Ser Thr Thr Ile
    50                  55                  60

Thr Arg Trp Arg Gly Val Cys Glu Glu His Ser Gly Thr Tyr Glu
65                  70                  75                  80

Lys Thr Asp Thr Glu Gly Lys Phe Leu Tyr His Arg Ser Arg Arg Asn
                85                  90                  95

Ile Asn Ile Glu Ser Tyr Val Val His Thr Asn Tyr Asp Glu Tyr Ala
            100                 105                 110

Ile Ile Leu Ser Lys Lys Ser Ser His His Gly Pro Thr Ile Thr
            115                 120                 125

Ala Lys Leu Tyr Gly Arg Gly Pro Gln Leu Arg Glu Ser Leu Leu Gln
            130                 135                 140

Glu Phe Arg Glu Val Ala Leu Gly Val Gly Ile Pro Glu Asp Ala Ile
145                 150                 155                 160

Phe Thr Met Ala Asp Arg Gly Glu Cys Val Pro Gly Glu Gln Glu Pro
                165                 170                 175

Asp Leu Thr Ser Ser Ser Arg
            180
```

<210> SEQ ID NO 42
<211> LENGTH: 183
<212> TYPE: PRT
<213> ORGANISM: Cavia porcellus

<400> SEQUENCE: 42

Asn Pro Val Leu Thr Leu Pro Asp Asp Ile Gln Val Gln Glu Asn Phe
1               5                   10                  15

Asp Glu Ser Arg Met Tyr Gly Lys Trp Tyr Ser Leu Ala Ile Gly Ser
            20                  25                  30

Thr Cys Pro Trp Leu Lys Arg Ile Lys Asp Arg Leu Ser Val Asp Thr
        35                  40                  45

Met Val Leu Gly Lys Gly Ala Thr Glu Ala Gln Met Ser Thr Thr Arg
    50                  55                  60

Thr His Trp Arg Arg Gly Val Cys Glu Arg Thr Ser Gly Phe Tyr Glu
65                  70                  75                  80

Lys Thr Asp Thr Ala Gly Lys Tyr Leu Tyr Ser Asn Pro Lys Trp Asn
                85                  90                  95

Leu Thr Met Glu Ser Tyr Val Val His Thr Asn Tyr Asp Glu Tyr Ala
            100                 105                 110

Thr Val Leu Thr Lys Lys Phe Ser Arg His His Gly Pro Thr Ile Thr
        115                 120                 125

Ala Lys Leu Tyr Gly Arg Glu Pro Gln Leu Arg Asp Ser Leu Leu Gln
    130                 135                 140

Gly Phe Arg Glu Met Ala Leu Ser Val Gly Ile Pro Glu Asp Ser Ile
145                 150                 155                 160

Phe Thr Met Ala Asn Arg Gly Glu Cys Ile Pro Gly Glu Gln Ile Pro
                165                 170                 175

Gln Pro Thr Pro Ala Leu Arg
            180

<210> SEQ ID NO 43
<211> LENGTH: 187
<212> TYPE: PRT
<213> ORGANISM: Monodelphis domestica

<400> SEQUENCE: 43

Gly Asn Pro Val Ser Ile Gln Asp Asp Ile Gln Val Gln Glu Asn Phe
1               5                   10                  15

Asn Leu Ser Arg Ile Phe Gly Lys Trp Tyr Asp Ile Ala Met Ala Ser
            20                  25                  30

Asn Cys Pro Trp Leu Lys Arg Leu Asn Arg Pro Leu Ser Met Gly Thr
        35                  40                  45

Leu Val Leu Gly Gln Gly Gln Thr Asp Gln Glu Ile Ser Thr Ile Arg
    50                  55                  60

Thr Arg Phe Arg Lys Gly Val Cys Glu Gln Val Ser Asp Val His Glu
65                  70                  75                  80

Lys Thr Asp Thr Glu Gly Lys Phe Ser Tyr Tyr Asn Ser Lys Trp Asn
                85                  90                  95

Val Thr Met Glu Tyr Phe Val Val His Thr Asn Tyr Asp Glu Tyr Val
            100                 105                 110

Met Ile Leu Lys His Lys Leu Arg His Ser Gly Pro Ser Thr Thr Val
        115                 120                 125

Thr Leu Tyr Gly Arg Arg Pro Gln Ile Arg Asn Ser Leu Leu Glu Glu
    130                 135                 140

Phe Lys Asp Phe Ala Leu Ser Leu Gly Ile Pro Glu Ser Ser Ile Tyr
145                 150                 155                 160

Phe Lys Leu Asp Lys Gly Glu Cys Val Pro Gly Glu Arg Glu Pro Val
            165                 170                 175

Pro Gln Pro Gln Val Ser Leu Ser Ala Ser Arg
        180                 185

<210> SEQ ID NO 44
<211> LENGTH: 179
<212> TYPE: PRT
<213> ORGANISM: Xenopus tropicalis

<400> SEQUENCE: 44

Ser Ser Pro Val Gln Thr Gln Glu Asp Ile Gln Val Gln Glu Asn Phe
1               5                   10                  15

Asp Leu Gln Lys Ile Tyr Gly Lys Trp Tyr Asp Val Ala Ile Gly Ser
            20                  25                  30

Thr Cys Lys Trp Leu Lys Leu His Lys Asp Lys Leu Asn Met Gly Thr
        35                  40                  45

Leu Glu Leu Ser Glu Gly Glu Ala Asp Gly Glu Val Arg Ile Val Asn
50                  55                  60

Thr Arg Met Arg His Gly Thr Cys Ser Gln Ile Val Gly Ala Tyr Gln
65                  70                  75                  80

Lys Thr Glu Thr Pro Gly Lys Phe Asp Tyr Phe Asn Gln Arg Trp Gly
            85                  90                  95

Thr Thr Ile Gln Asn Tyr Ile Val Phe Thr Asn Tyr Asn Glu Tyr Ala
        100                 105                 110

Ile Met Leu Met Arg Lys Lys Lys Gly Thr Glu Thr Thr Thr Thr Val
    115                 120                 125

Lys Leu Tyr Gly Arg Ser Pro Asp Leu Arg Pro Val Leu Ile Asp Glu
130                 135                 140

Phe Gln Gln Phe Ala Leu Ala Gln Gly Val Pro Glu Asp Ser Ile Phe
145                 150                 155                 160

Thr Leu Thr Asn Ser Gly Glu Cys Ala Pro Gly Asp Ile Glu Val Arg
            165                 170                 175

Pro Arg Arg

<210> SEQ ID NO 45
<211> LENGTH: 179
<212> TYPE: PRT
<213> ORGANISM: Xenopus laevis

<400> SEQUENCE: 45

Cys Ser Pro Ile Gln Pro Glu Asp Asn Ile Gln Ile Gln Glu Asn Phe
1               5                   10                  15

Asp Leu Gln Arg Ile Tyr Gly Lys Trp Tyr Asp Ile Ala Ile Gly Ser
            20                  25                  30

Thr Cys Lys Trp Leu Lys His His Lys Glu Lys Phe Asn Met Gly Thr
        35                  40                  45

Leu Glu Leu Ser Asp Gly Glu Thr Asp Gly Glu Val Arg Ile Val Asn
50                  55                  60

Thr Arg Met Arg His Gly Thr Cys Ser Gln Ile Val Gly Ser Tyr Gln
65                  70                  75                  80

Lys Thr Glu Thr Pro Gly Lys Phe Asp Tyr Phe Asn Ala Arg Trp Gly
            85                  90                  95

```
Thr Thr Ile Gln Asn Tyr Ile Val Phe Thr Asn Tyr Asn Glu Tyr Val
            100                 105                 110

Ile Met Gln Met Arg Lys Lys Lys Gly Ser Glu Thr Thr Thr Thr Val
        115                 120                 125

Lys Leu Tyr Gly Arg Ser Pro Asp Leu Arg Pro Thr Leu Val Asp Glu
    130                 135                 140

Phe Arg Gln Phe Ala Leu Ala Gln Gly Ile Pro Glu Asp Ser Ile Val
145                 150                 155                 160

Met Leu Pro Asn Asn Gly Glu Cys Ser Pro Gly Glu Ile Glu Val Arg
                165                 170                 175

Pro Arg Arg

<210> SEQ ID NO 46
<211> LENGTH: 183
<212> TYPE: PRT
<213> ORGANISM: Ctenopharyngodon idella

<400> SEQUENCE: 46

Ala Gly Pro Leu Pro Asp Glu Pro Val Leu Gln Thr Gln Glu Asn Phe
1               5                   10                  15

Asp Val Thr Arg Phe Met Gly Lys Trp Tyr Asp Ile Ala Met Ala Ser
            20                  25                  30

Thr Cys Pro Trp Leu Lys Arg His Lys Gly Asp Ala Ala Ile Gly Ser
        35                  40                  45

Met Glu Leu Gln Tyr Ser Ala Ser Thr Gln Thr Ile Ser Val Thr Arg
    50                  55                  60

Ile Gly Leu Arg His Gly Thr Cys Lys Ser Ile Ser Gly Glu Tyr Gln
65                  70                  75                  80

Leu Thr Lys Thr Pro Gly Arg Phe His Tyr His Ile Ala Lys Trp Asn
                85                  90                  95

Ala Asp Val Asp Ser Tyr Val Val His Thr Asn Tyr Asp Glu Tyr Ala
            100                 105                 110

Leu Val Val Met Tyr Lys Gln Lys Thr Gly Gly Glu Lys Ser Thr Ser
        115                 120                 125

Val Lys Leu Tyr Gly Arg Thr Met Gln Leu Arg Pro Thr Leu Ile Glu
    130                 135                 140

Glu Phe Lys Thr Leu Val Ala Glu Gln Gly Met Ser Glu Asp Thr Ile
145                 150                 155                 160

Val Ile Lys Lys Asn Lys Gly Glu Cys Val Pro Gly Glu Gln Ala Thr
                165                 170                 175

Pro Glu Pro Gln Ile Gln Arg
            180

<210> SEQ ID NO 47
<211> LENGTH: 183
<212> TYPE: PRT
<213> ORGANISM: Danio rerio

<400> SEQUENCE: 47

Ala Gly Pro Leu Pro Asp Glu Pro Val Leu Gln Thr Gln Glu Asn Phe
1               5                   10                  15

Asn Val Asn Arg Phe Met Gly Lys Trp Tyr Asp Ile Ala Val Ala Ser
            20                  25                  30

Thr Cys Pro Trp Met Lys Arg His Lys Gly Asp Ala Ala Ile Gly Ser
        35                  40                  45

Leu Glu Leu Gln Ser Ser Gly Ser Pro Gln Ser Leu Ser Met Thr Arg
```

```
            50                  55                  60
Ile Gly Leu Arg Arg Gly Thr Cys Lys Ser Ile Ser Gly Glu Tyr Gln
 65                  70                  75                  80

Leu Thr Lys Thr Pro Gly Arg Phe His Tyr His Ser Ala Lys Trp Asn
                 85                  90                  95

Ser Asp Val Asp Ala Tyr Val Val His Thr Asn Tyr Asn Glu Tyr Ala
                100                 105                 110

Leu Val Val Met Leu Lys Gln Lys Pro Gly Gly Glu Lys Ser Thr Ser
            115                 120                 125

Val Lys Leu Tyr Gly Arg Thr Met Glu Leu Arg Pro Thr Leu Ile Glu
        130                 135                 140

Asp Phe Lys Thr Leu Val Ala Glu Gln Gly Met Ser Glu Asp Thr Ile
145                 150                 155                 160

Ile Ile Lys Lys Asn Lys Gly Glu Cys Val Pro Gly Glu Glu Thr Thr
                165                 170                 175

Pro Glu Pro Gln Ile Gln Arg
            180
```

<210> SEQ ID NO 48
<211> LENGTH: 188
<212> TYPE: PRT
<213> ORGANISM: Oncorhynchus mykiss

<400> SEQUENCE: 48

```
Gly Val Pro Leu Leu Pro Glu Pro Leu Phe Pro Thr Gln Glu Asn Phe
 1               5                  10                  15

Asp Leu Thr Lys Phe Met Gly Lys Trp His Asp Ile Ala Val Ala Ser
                20                  25                  30

Thr Trp Pro Trp Met Gln Arg His Lys Gly Asp Ala Ala Ile Gly Ile
            35                  40                  45

Leu Glu Leu Gln Ala Ser Gly Thr Glu Asp Lys Val Ser Met Thr Arg
        50                  55                  60

Ser Met Asn Lys His Gly Thr Cys Gln Gln Ile Ser Gly Asp Tyr Lys
 65                  70                  75                  80

Leu Thr Asp Thr Pro Gly Arg Phe Thr Tyr His Ile Ala Lys Trp Gly
                 85                  90                  95

Ala Asp Val Asp Ala Tyr Val Val Asp Thr Asn Tyr Asp Glu Tyr Ala
                100                 105                 110

Ile Val Met Ile Ser Lys Gln Lys Thr Glu Gly Glu Lys Thr Lys Ser
            115                 120                 125

Ala Lys Leu Tyr Ser Arg Thr Met Glu Leu Ser Pro Ala Ile Leu Glu
        130                 135                 140

Asp Phe Arg Arg Leu Val Arg Glu Gln Gly Met Asp Asp Asn Thr Ile
145                 150                 155                 160

Ile Ile Lys Gln Asn Lys Gly Glu Cys Val Pro Gly Thr Glu Pro Val
                165                 170                 175

Ala Ser Glu Pro Gln Pro Glu Ile Thr Ala Pro Arg
            180                 185
```

<210> SEQ ID NO 49
<211> LENGTH: 188
<212> TYPE: PRT
<213> ORGANISM: Salmo salar

<400> SEQUENCE: 49

Gly Val Pro Val Leu Ala Glu Pro Leu Phe Pro Thr Gln Glu Asn Phe

```
                1               5                  10                  15
        Asp Leu Ser Lys Phe Met Gly Lys Trp His Asp Ile Ala Val Ala Ser
                        20                  25                  30

Thr Cys Pro Trp Ile Gln Arg His Arg Gly Asp Ala Ala Ile Gly Ile
                        35                  40                  45

Leu Glu Leu Gln Ala Gly Asp Thr Glu Gly Lys Val Ser Met Lys Arg
                50                  55                  60

Ser Met Lys Lys His Gly Thr Cys Lys Gln Ile Ser Gly Asp Tyr Glu
        65                  70                  75                  80

Leu Thr Asp Thr Pro Gly Arg Phe Thr Tyr His Val Ala Lys Trp Gly
                        85                  90                  95

Ala Asp Val Asp Ala Tyr Val Val His Thr Asn Tyr Asp Glu Tyr Ala
                        100                 105                 110

Ile Val Met Met Ser Lys Gln Lys Thr Gly Gly Glu Lys Thr Lys Ser
                        115                 120                 125

Ala Lys Leu Tyr Ser Arg Thr Met Glu Leu Arg Thr Thr Ile Leu Asp
                130                 135                 140

Asp Phe Arg Arg Leu Val Arg Glu Gln Gly Met Ala Asp Asp Thr Val
        145                 150                 155                 160

Ile Ile Lys Gln Asn Lys Gly Glu Cys Ile Pro Gly Ala Glu Pro Val
                        165                 170                 175

Ala Ala Glu Ser Gln Ser Glu Ile Thr Ala Pro Arg
                        180                 185

<210> SEQ ID NO 50
<211> LENGTH: 186
<212> TYPE: PRT
<213> ORGANISM: Esox lucius

<400> SEQUENCE: 50

Gly Val Pro Val Leu Thr Asp Pro Leu Tyr Thr Thr Gln Glu Asn Phe
        1               5                   10                  15

Asp Leu Ser Lys Phe Met Gly Lys Trp His Asp Ile Ala Met Ala Ser
                        20                  25                  30

Thr Cys Pro Trp Met Gln Arg His Lys Gly Asp Ala Ala Ile Gly Thr
                        35                  40                  45

Leu Glu Leu Gln Thr Gly Ser Thr Glu Gly Lys Ile Ser Met Thr Arg
                50                  55                  60

Lys Met Lys Lys Leu Gly Thr Cys Lys Gln Ile Ser Gly Glu Tyr Gln
        65                  70                  75                  80

Ile Thr Asp Thr Pro Gly Arg Phe Thr Tyr His Val Ala Lys Trp Gly
                        85                  90                  95

Ala Asp Val Asp Ala Tyr Val Val His Thr Asn Tyr Asp Glu Tyr Ala
                        100                 105                 110

Ile Val Leu Met Ser Lys Gln Lys Thr Gly Gly Glu Lys Thr Lys Ser
                        115                 120                 125

Ala Lys Leu Tyr Ser Arg Thr Met Glu Val Arg Asp Thr Ile Leu Asp
                130                 135                 140

Asp Phe Lys Arg Leu Val Lys Glu Gln Gly Met Ala Asp Asp Thr Val
        145                 150                 155                 160

Val Val Lys Gln Asn Lys Gly Glu Cys Ile Pro Gly Val Glu Thr Val
                        165                 170                 175

Gln Thr Glu Pro Gln Pro Asp Ile Thr Arg
                        180                 185
```

<210> SEQ ID NO 51
<211> LENGTH: 185
<212> TYPE: PRT
<213> ORGANISM: Pleuronectes platessa

<400> SEQUENCE: 51

```
Gly Leu Pro Val Leu Pro Glu Pro Leu Tyr Pro Thr Gln Glu Asn Phe
1               5                   10                  15

Asp Leu Thr Arg Phe Val Gly Thr Trp His Asp Val Ala Leu Thr Ser
            20                  25                  30

Ser Cys Pro His Met Gln Arg Asn Arg Ala Asp Ala Ala Ile Gly Lys
        35                  40                  45

Leu Val Leu Glu Lys Asp Thr Gly Asn Lys Leu Lys Val Thr Arg Thr
    50                  55                  60

Arg Leu Arg His Gly Thr Cys Val Glu Met Ser Gly Glu Tyr Glu Leu
65                  70                  75                  80

Thr Ser Thr Pro Gly Arg Ile Phe Tyr His Ile Asp Arg Trp Asp Ala
                85                  90                  95

Asp Val Asp Ala Tyr Val Val His Thr Asn Tyr Asp Glu Tyr Ala Ile
            100                 105                 110

Ile Ile Met Ser Lys Gln Lys Thr Ser Gly Glu Asn Ser Thr Ser Leu
        115                 120                 125

Lys Leu Tyr Ser Arg Thr Met Ser Val Arg Asp Thr Val Leu Asp Asp
    130                 135                 140

Phe Lys Thr Leu Val Arg His Gln Gly Met Ser Asp Asp Thr Ile Ile
145                 150                 155                 160

Ile Lys Gln Asn Lys Gly Asp Cys Ile Pro Gly Glu Gln Val Glu Glu
                165                 170                 175

Ala Pro Ser Gln Pro Glu Pro Lys Arg
            180                 185
```

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic 6xHis tag

<400> SEQUENCE: 52

```
His His His His His His
1               5
```

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid

```
<400> SEQUENCE: 53

Phe Xaa Xaa Gly Xaa Xaa Cys Xaa Gly
1               5

<210> SEQ ID NO 54
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Thr Cys Pro Phe
1

<210> SEQ ID NO 55
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Leu Cys Pro Gly
1

<210> SEQ ID NO 56
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Phe Cys Pro Gly
1

<210> SEQ ID NO 57
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Val Cys Pro Met
1

<210> SEQ ID NO 58
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Pro Cys Pro Ala
1

<210> SEQ ID NO 59
<211> LENGTH: 183
<212> TYPE: PRT
```

<213> ORGANISM: Homo sapiens

<400> SEQUENCE: 59

```
Gly Pro Val Pro Thr Pro Pro Asp Asn Ile Gln Val Gln Glu Asn Phe
1               5                   10                  15

Asn Ile Ser Arg Ile Tyr Gly Lys Trp Tyr Asn Leu Ala Ile Gly Ser
            20                  25                  30

Thr Cys Pro Trp Leu Lys Lys Ile Met Asp Arg Met Thr Val Ser Thr
        35                  40                  45

Leu Val Leu Gly Glu Gly Ala Thr Glu Ala Glu Ile Ser Met Thr Ser
    50                  55                  60

Thr Arg Trp Arg Lys Gly Val Cys Glu Glu Thr Ser Gly Ala Tyr Glu
65                  70                  75                  80

Lys Thr Asp Thr Asp Gly Lys Phe Leu Tyr His Lys Ser Lys Trp Asn
                85                  90                  95

Ile Thr Met Glu Ser Tyr Val Val His Thr Asn Tyr Asp Glu Tyr Ala
            100                 105                 110

Ile Phe Leu Thr Lys Lys Phe Ser Arg His His Gly Pro Thr Ile Thr
        115                 120                 125

Ala Lys Leu Tyr Gly Arg Ala Pro Gln Leu Arg Glu Thr Leu Leu Gln
    130                 135                 140

Asp Phe Arg Val Val Ala Gln Gly Val Gly Ile Pro Glu Asp Ser Ile
145                 150                 155                 160

Phe Thr Met Ala Asp Arg Gly Glu Cys Val Pro Gly Glu Gln Glu Pro
                165                 170                 175

Glu Pro Ile Leu Ile Pro Arg
            180
```

<210> SEQ ID NO 60
<211> LENGTH: 152
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (19)..(21)
<223> OTHER INFORMATION: a, c, t or g
<220> FEATURE:
<221> NAME/KEY: modified_base
<222> LOCATION: (25)..(27)
<223> OTHER INFORMATION: a, c, t or g
<220> FEATURE:
<221> NAME/KEY: modified_base
<222> LOCATION: (52)..(54)
<223> OTHER INFORMATION: a, c, t or g
<220> FEATURE:
<221> NAME/KEY: modified_base
<222> LOCATION: (58)..(60)
<223> OTHER INFORMATION: a, c, t or g
<220> FEATURE:
<221> NAME/KEY: modified_base
<222> LOCATION: (64)..(66)
<223> OTHER INFORMATION: a, c, t or g
<220> FEATURE:
<221> NAME/KEY: modified_base
<222> LOCATION: (103)..(105)
<223> OTHER INFORMATION: a, c, t or g
<220> FEATURE:
<221> NAME/KEY: modified_base
<222> LOCATION: (124)..(126)
<223> OTHER INFORMATION: a, c, t or g
<220> FEATURE:
<221> NAME/KEY: modified_base
<222> LOCATION: (130)..(132)

<223> OTHER INFORMATION: a, c, t or g

<400> SEQUENCE: 60
accgaagcag aaatcagcnn naccnnnacc cgttggcgta aaggtgtttg tnnngaannn    60
agcnnngcct acgaaaagac cgataccgac ggtaaattcc tgnnncataa aagcaaacat   120
aacnnnaccn nngaaagcta tgtcgtgcac ac                                 152

<210> SEQ ID NO 61
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(21)
<223> OTHER INFORMATION: a, c, t or g
<220> FEATURE:
<221> NAME/KEY: modified_base
<222> LOCATION: (25)..(27)
<223> OTHER INFORMATION: a, c, t or g
<220> FEATURE:
<221> NAME/KEY: modified_base
<222> LOCATION: (49)..(51)
<223> OTHER INFORMATION: a, c, t or g
<220> FEATURE:
<221> NAME/KEY: modified_base
<222> LOCATION: (55)..(57)
<223> OTHER INFORMATION: a, c, t or g
<220> FEATURE:
<221> NAME/KEY: modified_base
<222> LOCATION: (61)..(63)
<223> OTHER INFORMATION: a, c, t or g

<400> SEQUENCE: 61
gagtacgcca tcttcctgnn naaannnttc agccgtcatc atggtccgnn nattnnngca    60
nnnctgtatg gtcgtgcacc t                                              81

<210> SEQ ID NO 62
<211> LENGTH: 582
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(579)

<400> SEQUENCE: 62

```
ggc cct gtg cca acg ccg ccc gac aat atc caa gtg cag gaa aac ttc    48
Gly Pro Val Pro Thr Pro Pro Asp Asn Ile Gln Val Gln Glu Asn Phe
1               5                   10                  15 aat atc tcc cag atc tat ggg aaa tgg tat aat ctg gca att ggt agc    96
Asn Ile Ser Gln Ile Tyr Gly Lys Trp Tyr Asn Leu Ala Ile Gly Ser
            20                  25                  30 acc agc ccg tgg ctg aag aaa atc atg gat cgt atg acc gtt agc acc   144
Thr Ser Pro Trp Leu Lys Lys Ile Met Asp Arg Met Thr Val Ser Thr
        35                  40                  45 ctg gtt ctg ggt gaa ggt gct acc gaa gca gaa atc agc atg acc agc   192
Leu Val Leu Gly Glu Gly Ala Thr Glu Ala Glu Ile Ser Met Thr Ser
    50                  55                  60 acc cgt tgg cgt aaa ggt gtt tgt gaa gaa acc agc ggt gcc tac gaa   240
Thr Arg Trp Arg Lys Gly Val Cys Glu Glu Thr Ser Gly Ala Tyr Glu
65                  70                  75                  80
```

```
aag acc gat acc gac ggt aaa ttc ctg tat cat aaa agc aaa cat aac    288
Lys Thr Asp Thr Asp Gly Lys Phe Leu Tyr His Lys Ser Lys His Asn
                85                  90                  95 atc acc atg gaa agc tat gtc gtg cac acc aac tat gat gag tac gcc    336
Ile Thr Met Glu Ser Tyr Val Val His Thr Asn Tyr Asp Glu Tyr Ala
            100                 105                 110 atc ttc ctg acc aaa aaa ttc agc cgt cat cat ggt ccg acc att acc    384
Ile Phe Leu Thr Lys Lys Phe Ser Arg His His Gly Pro Thr Ile Thr
        115                 120                 125 gca aaa ctg tat ggt cgt gca cct cag ctg cgt gaa acc ctg ctg cag    432
Ala Lys Leu Tyr Gly Arg Ala Pro Gln Leu Arg Glu Thr Leu Leu Gln
    130                 135                 140 gat ttt cgt gtt gtt gcc cag ggt gtt ggc atc cct gag gac tcc atc    480
Asp Phe Arg Val Val Ala Gln Gly Val Gly Ile Pro Glu Asp Ser Ile
145                 150                 155                 160 ttc acc atg gct gac cga ggt gaa tgt gtc cct ggg gag cag gaa cca    528
Phe Thr Met Ala Asp Arg Gly Glu Cys Val Pro Gly Glu Gln Glu Pro
                165                 170                 175 gag ccc atc tta atc ccg aga agc gct tgg tct cac ccg cag ttc gaa    576
Glu Pro Ile Leu Ile Pro Arg Ser Ala Trp Ser His Pro Gln Phe Glu
            180                 185                 190 aaa taa                                                             582
Lys

<210> SEQ ID NO 63
<211> LENGTH: 193
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Gly Pro Val Pro Thr Pro Pro Asp Asn Ile Gln Val Gln Glu Asn Phe
1               5                   10                  15

Asn Ile Ser Gln Ile Tyr Gly Lys Trp Tyr Asn Leu Ala Ile Gly Ser
            20                  25                  30

Thr Ser Pro Trp Leu Lys Lys Ile Met Asp Arg Met Thr Val Ser Thr
        35                  40                  45

Leu Val Leu Gly Glu Gly Ala Thr Glu Ala Glu Ile Ser Met Thr Ser
    50                  55                  60

Thr Arg Trp Arg Lys Gly Val Cys Glu Glu Thr Ser Gly Ala Tyr Glu
65                  70                  75                  80

Lys Thr Asp Thr Asp Gly Lys Phe Leu Tyr His Lys Ser Lys His Asn
                85                  90                  95

Ile Thr Met Glu Ser Tyr Val Val His Thr Asn Tyr Asp Glu Tyr Ala
            100                 105                 110

Ile Phe Leu Thr Lys Lys Phe Ser Arg His His Gly Pro Thr Ile Thr
        115                 120                 125

Ala Lys Leu Tyr Gly Arg Ala Pro Gln Leu Arg Glu Thr Leu Leu Gln
    130                 135                 140

Asp Phe Arg Val Val Ala Gln Gly Val Gly Ile Pro Glu Asp Ser Ile
145                 150                 155                 160

Phe Thr Met Ala Asp Arg Gly Glu Cys Val Pro Gly Glu Gln Glu Pro
                165                 170                 175

Glu Pro Ile Leu Ile Pro Arg Ser Ala Trp Ser His Pro Gln Phe Glu
            180                 185                 190

Lys
```

<210> SEQ ID NO 64
<211> LENGTH: 193
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gly Pro Val Pro Thr Pro Pro Asp Asn Ile Gln Val Gln Glu Asn Phe
1               5                   10                  15

Asn Ile Ser Gln Ile Tyr Gly Lys Trp Tyr Asn Leu Ala Ile Gly Ser
            20                  25                  30

Thr Ser Pro Trp Leu Lys Lys Ile Met Asp Arg Met Thr Val Ser Thr
        35                  40                  45

Leu Val Leu Gly Glu Gly Ala Thr Glu Ala Glu Ile Ser Met Thr Ser
    50                  55                  60

Thr Arg Trp Arg Lys Gly Val Cys Glu Glu Thr Ser Gly Ala Tyr Glu
65                  70                  75                  80

Lys Thr Asp Thr Asp Gly Lys Phe Leu Tyr His Lys Ser Lys His Asn
                85                  90                  95

Ile Thr Met Glu Ser Tyr Val Val His Thr Asn Tyr Asp Glu Tyr Ala
            100                 105                 110

Ile Phe Leu Thr Lys Lys Phe Ser Arg Gln His Gly Pro Thr Ile Thr
        115                 120                 125

Ala Lys Leu Tyr Gly Arg Ala Pro Gln Leu Arg Glu Thr Leu Leu Gln
    130                 135                 140

Asp Phe Arg Val Val Ala Gln Gly Val Gly Ile Pro Glu Asp Ser Ile
145                 150                 155                 160

Phe Thr Met Ala Asp Arg Gly Glu Cys Val Pro Gly Glu Gln Glu Pro
                165                 170                 175

Glu Pro Ile Leu Ile Pro Arg Ser Ala Trp Ser His Pro Gln Phe Glu
            180                 185                 190

Lys

<210> SEQ ID NO 65
<211> LENGTH: 183
<212> TYPE: PRT
<213> ORGANISM: Artificial Sequence
<220> FEATURE:
<223> OTHER INFORMATION: Description of Artificial Sequence: Synthetic
      a1m mutein D1A10
<220> FEATURE:
<221> NAME/KEY: MOD_RES
<222> LOCATION: (20)..(20)
<223> OTHER INFORMATION: Any amino acid
<220> FEATURE:
<221> NAME/KEY: MOD_RES
<222> LOCATION: (34)..(34)
<223> OTHER INFORMATION: Any amino acid
<220> FEATURE:
<221> NAME/KEY: MOD_RES
<222> LOCATION: (36)..(37)
<223> OTHER INFORMATION: Any amino acid
<220> FEATURE:
<221> NAME/KEY: MOD_RES
<222> LOCATION: (47)..(47)
<223> OTHER INFORMATION: Any amino acid
<220> FEATURE:
<221> NAME/KEY: MOD_RES
<222> LOCATION: (62)..(62)
<223> OTHER INFORMATION: Any amino acid
<220> FEATURE:

```
<221> NAME/KEY: MOD_RES
<222> LOCATION: (64)..(64)
<223> OTHER INFORMATION: Any amino acid
<220> FEATURE:
<221> NAME/KEY: MOD_RES
<222> LOCATION: (73)..(73)
<223> OTHER INFORMATION: Any amino acid
<220> FEATURE:
<221> NAME/KEY: MOD_RES
<222> LOCATION: (75)..(75)
<223> OTHER INFORMATION: Any amino acid
<220> FEATURE:
<221> NAME/KEY: MOD_RES
<222> LOCATION: (77)..(77)
<223> OTHER INFORMATION: Any amino acid
<220> FEATURE:
<221> NAME/KEY: MOD_RES
<222> LOCATION: (90)..(90)
<223> OTHER INFORMATION: Any amino acid
<220> FEATURE:
<221> NAME/KEY: MOD_RES
<222> LOCATION: (97)..(97)
<223> OTHER INFORMATION: Any amino acid
<220> FEATURE:
<221> NAME/KEY: MOD_RES
<222> LOCATION: (99)..(99)
<223> OTHER INFORMATION: Any amino acid
<220> FEATURE:
<221> NAME/KEY: MOD_RES
<222> LOCATION: (116)..(116)
<223> OTHER INFORMATION: Any amino acid
<220> FEATURE:
<221> NAME/KEY: MOD_RES
<222> LOCATION: (118)..(118)
<223> OTHER INFORMATION: Any amino acid
<220> FEATURE:
<221> NAME/KEY: MOD_RES
<222> LOCATION: (126)..(126)
<223> OTHER INFORMATION: Any amino acid
<220> FEATURE:
<221> NAME/KEY: MOD_RES
<222> LOCATION: (128)..(128)
<223> OTHER INFORMATION: Any amino acid
<220> FEATURE:
<221> NAME/KEY: MOD_RES
<222> LOCATION: (130)..(130)
<223> OTHER INFORMATION: Any amino acid

<400> SEQUENCE: 65

Gly Pro Val Pro Thr Pro Pro Asp Asn Ile Gln Val Gln Glu Asn Phe
1               5                   10                  15

Asn Ile Ser Xaa Ile Tyr Gly Lys Trp Tyr Asn Leu Ala Ile Gly Ser
            20                  25                  30

Thr Xaa Pro Xaa Xaa Lys Lys Ile Met Asp Arg Met Thr Val Xaa Thr
        35                  40                  45

Leu Val Leu Gly Glu Gly Ala Thr Glu Ala Glu Ile Ser Xaa Thr Xaa
50                  55                  60

Thr Arg Trp Arg Lys Gly Val Cys Xaa Glu Xaa Ser Xaa Ala Tyr Glu
65                  70                  75                  80

Lys Thr Asp Thr Asp Gly Lys Phe Leu Xaa His Lys Ser Lys His Asn
                85                  90                  95

Xaa Thr Xaa Glu Ser Tyr Val Val His Thr Asn Tyr Asp Glu Tyr Ala
            100                 105                 110

Ile Phe Leu Xaa Lys Xaa Phe Ser Arg Gln His Gly Pro Xaa Ile Xaa
            115                 120                 125

Ala Xaa Leu Tyr Gly Arg Ala Pro Gln Leu Arg Glu Thr Leu Leu Gln
        130                 135                 140

Asp Phe Arg Val Val Ala Gln Gly Val Gly Ile Pro Glu Asp Ser Ile
145                 150                 155                 160
```

Phe Thr Met Ala Asp Arg Gly Glu Cys Val Pro Gly Glu Gln Glu Pro
                165                 170                 175

Glu Pro Ile Leu Ile Pro Arg
            180

<210> SEQ ID NO 66
<211> LENGTH: 183
<212> TYPE: PRT
<213> ORGANISM: Artificial Sequence
<220> FEATURE:
<223> OTHER INFORMATION: Description of Artificial Sequence: Synthetic
      a1m mutein D1H3
<220> FEATURE:
<221> NAME/KEY: MOD_RES
<222> LOCATION: (34)..(34)
<223> OTHER INFORMATION: Any amino acid
<220> FEATURE:
<221> NAME/KEY: MOD_RES
<222> LOCATION: (36)..(37)
<223> OTHER INFORMATION: Any amino acid
<220> FEATURE:
<221> NAME/KEY: MOD_RES
<222> LOCATION: (47)..(47)
<223> OTHER INFORMATION: Any amino acid
<220> FEATURE:
<221> NAME/KEY: MOD_RES
<222> LOCATION: (62)..(62)
<223> OTHER INFORMATION: Any amino acid
<220> FEATURE:
<221> NAME/KEY: MOD_RES
<222> LOCATION: (64)..(64)
<223> OTHER INFORMATION: Any amino acid
<220> FEATURE:
<221> NAME/KEY: MOD_RES
<222> LOCATION: (73)..(73)
<223> OTHER INFORMATION: Any amino acid
<220> FEATURE:
<221> NAME/KEY: MOD_RES
<222> LOCATION: (75)..(75)
<223> OTHER INFORMATION: Any amino acid
<220> FEATURE:
<221> NAME/KEY: MOD_RES
<222> LOCATION: (77)..(77)
<223> OTHER INFORMATION: Any amino acid
<220> FEATURE:
<221> NAME/KEY: MOD_RES
<222> LOCATION: (90)..(90)
<223> OTHER INFORMATION: Any amino acid
<220> FEATURE:
<221> NAME/KEY: MOD_RES
<222> LOCATION: (97)..(97)
<223> OTHER INFORMATION: Any amino acid
<220> FEATURE:
<221> NAME/KEY: MOD_RES
<222> LOCATION: (99)..(99)
<223> OTHER INFORMATION: Any amino acid
<220> FEATURE:
<221> NAME/KEY: MOD_RES
<222> LOCATION: (116)..(116)
<223> OTHER INFORMATION: Any amino acid
<220> FEATURE:
<221> NAME/KEY: MOD_RES
<222> LOCATION: (118)..(118)
<223> OTHER INFORMATION: Any amino acid
<220> FEATURE:
<221> NAME/KEY: MOD_RES
<222> LOCATION: (126)..(126)
<223> OTHER INFORMATION: Any amino acid
<220> FEATURE:
<221> NAME/KEY: MOD_RES
<222> LOCATION: (128)..(128)
<223> OTHER INFORMATION: Any amino acid
<220> FEATURE:
<221> NAME/KEY: MOD_RES
<222> LOCATION: (130)..(130)
<223> OTHER INFORMATION: Any amino acid

<400> SEQUENCE: 66

```
Gly Pro Val Pro Thr Pro Pro Asp Asn Ile Gln Val Gln Glu Asn Phe
1               5                   10                  15

Asn Ile Ser Gln Ile Tyr Gly Lys Trp Tyr Asn Leu Ala Ile Gly Ser
            20                  25                  30

Thr Xaa Pro Xaa Xaa Lys Lys Ile Met Asp Arg Met Thr Val Xaa Thr
        35                  40                  45

Leu Val Leu Gly Glu Gly Ala Thr Glu Ala Glu Ile Ser Xaa Thr Xaa
        50                  55                  60

Thr Arg Trp Arg Lys Gly Val Cys Xaa Glu Xaa Ser Xaa Ala Tyr Glu
65                  70                  75                  80

Lys Thr Asp Thr Asp Gly Lys Phe Leu Xaa His Lys Ser Lys His Asn
                85                  90                  95

Xaa Thr Xaa Glu Ser Tyr Val Val His Thr Asn Tyr Asp Glu Tyr Ala
            100                 105                 110

Ile Phe Leu Xaa Lys Xaa Phe Ser Arg Gln His Gly Pro Xaa Ile Xaa
            115                 120                 125

Ala Xaa Leu Tyr Gly Arg Ala Pro Gln Leu Arg Glu Thr Leu Leu Gln
    130                 135                 140

Asp Phe Arg Val Val Ala Gln Gly Val Gly Ile Pro Glu Asp Ser Ile
145                 150                 155                 160

Phe Thr Met Ala Asp Arg Gly Glu Cys Val Pro Gly Glu Gln Glu Pro
                165                 170                 175

Glu Pro Ile Leu Ile Pro Arg
                180
```